United States Patent
Gaon et al.

(10) Patent No.: US 10,380,505 B2
(45) Date of Patent: Aug. 13, 2019

(54) METHODS AND SYSTEMS FOR DYNAMICALLY GENERATING REAL-TIME RECOMMENDATIONS

(71) Applicant: WISDO LTD., Herzliya (IL)

(72) Inventors: Boaz Gaon, Herzliya (IL); Ido Jonathan Engel, Herzliya (IL); Arik Gilon, Herzliya (IL); Arie Gofer, Herzliya (IL)

(73) Assignee: WISDO LTD., Herzliya (IL)

( * ) Notice: Subject to any disclaimer, the term of this patent is extended or adjusted under 35 U.S.C. 154(b) by 50 days.

(21) Appl. No.: 15/600,644

(22) Filed: May 19, 2017

(65) Prior Publication Data

US 2017/0286857 A1     Oct. 5, 2017

Related U.S. Application Data

(63) Continuation of application No. 15/217,878, filed on Jul. 22, 2016, now Pat. No. 9,710,757.

(60) Provisional application No. 62/196,142, filed on Jul. 23, 2015, provisional application No. 62/195,762, filed on Jul. 22, 2015.

(51) Int. Cl.
| | |
|---|---|
| *G06N 99/00* | (2019.01) |
| *G16H 20/70* | (2018.01) |
| *G06F 19/00* | (2018.01) |
| *G06Q 10/10* | (2012.01) |
| *G16H 10/20* | (2018.01) |
| *G16H 50/20* | (2018.01) |

(52) U.S. Cl.
CPC ......... *G06N 99/00* (2013.01); *G06F 19/3456* (2013.01); *G06F 19/3481* (2013.01); *G06Q 10/10* (2013.01); *G16H 10/20* (2018.01); *G16H 20/70* (2018.01); *G16H 50/20* (2018.01)

(58) Field of Classification Search
CPC .................................................... G06N 99/00
See application file for complete search history.

(56) References Cited

U.S. PATENT DOCUMENTS

| | | |
|---|---|---|
| 6,446,095 B1 | 9/2002 | Mukai |
| 8,606,792 B1 | 12/2013 | Jackson et al. |
| 2008/0235590 A1 | 9/2008 | Krantz et al. |

(Continued)

FOREIGN PATENT DOCUMENTS

| | | |
|---|---|---|
| WO | WO2017013494 A2 | 1/2017 |
| WO | WO2017013494 A3 | 3/2017 |

OTHER PUBLICATIONS

J. Bian et al., "Finding the Right Facts in the Crowd: Factoid Question Answering over Social Media", Assoc. Comp. Mach. proc. WWW, Apr. 2008, pp. 467-476.*

(Continued)

*Primary Examiner* — Vincent Gonzales
(74) *Attorney, Agent, or Firm* — Wilson Sonsini Goodrich & Rosati

(57) ABSTRACT

Systems and methods are provided herein for generating personalized timeline-based feeds to a user. A computer-implemented method for generating feeds to a user may be provided. The method may include generating a timeline comprising a plurality of milestones and needs associated with an event, and providing the feeds based on community wisdom. The feeds may be provided for each milestone on the time-line specific to the user, and may be configured to address the user's needs at each milestone.

30 Claims, 29 Drawing Sheets

(56) References Cited

U.S. PATENT DOCUMENTS

| | | |
|---|---|---|
| 2010/0161467 A1 | 6/2010 | Ageenko et al. |
| 2014/0012574 A1 | 1/2014 | Pasupalak et al. |
| 2017/0024656 A1 | 1/2017 | Gilon et al. |

OTHER PUBLICATIONS

Blum et al., Selection of Relevant Features and Examples in Machine Learning, Art. Intell. 1997, 97:245-71.
International search report and written opinion dated Feb. 9, 2017 for PCT Application No. IB-201601148.
Lotosh, et al., CrowdPlanr: Planning Made Easy with Crowd, IEEE Int'l Conf. on Data Engineering, 2013, 1344-47.
Notice of allowance dated Mar. 27, 2017 for U.S. Appl. No. 15/217,878.
Notice of allowance dated Apr. 27, 2017 for U.S. Appl. No. 15/217,878.
Office action dated Nov. 15, 2016 for U.S. Appl. No. 15/217,878.
Russell et al., A Modern Approach, 2nd Ed., 2003, 375-461.
EP16827320.9 Extended Search Report dated Jul. 10, 2018.

\* cited by examiner

FIG. 8 production environment - curation master
2015-07-06_10:16:23 [dd7eadc68f]                                    Logged in as: ( sign out )

◁ Home   ✉ Insight List   ⧉ New Insight

Insight Notes

Owner: [boaz ▾]                Conversation (internal)         Additional Information (internal, not shown)
Stage: [Approved ▾]            [                    ]          From      community page.
☐ Live                         [                    ]          Created   Mon Jul 13 20:55:18 UTC 2015
Created By:                                                    Suggested timing:Beginning of first chemo
Notes updated: Jul 14, 2015 03:42:05
Insight updated: Jul 14, 2015 03:42:00                                                          ⟳ Update

Insight Data

Identifier    BC_014030
Title         Hair Loss - when, what, how to achieve control
Content       Typically hair loss occurs between day 10-14 of your first chemo cycle.
              Before this occurs is the time to decide how you want to handle hair loss
              and covering your head. Cutting your hair short or shaving it off before this
              time will absorb some of the shock of the loss, give you greater control -
              and prevent a clogged drain!
Domain        Treatment
Relevant Time
              [Months|Weeks|D⌢⌢⌢⌢⌢⌢|1 Week|        ]
                            [3 Days|1st Chemo|Hours|Days] [Weeks|Months]
              Optimal: on Milestone.
              Start: 3 Days before Milestone.
              End: 1 Week after Milestone.
Priority      1
Source        Lori

↶                                              ◌ ☆ ⸜

ⓛ Lori
   Hair Loss - when, what, how        [TREATMENT]
   to achieve control

Typically hair loss occurs between day
   10-14 of your first chemo cycle. Before
   this occurs is the time to decide how you
   want to handle hair loss and covering
   your head. Cutting your hair short or
   shaving it off before this time will absorb
   some of the shock of the loss, give you
   greater control - and prevent a clogged
   drain!

FIG. 9

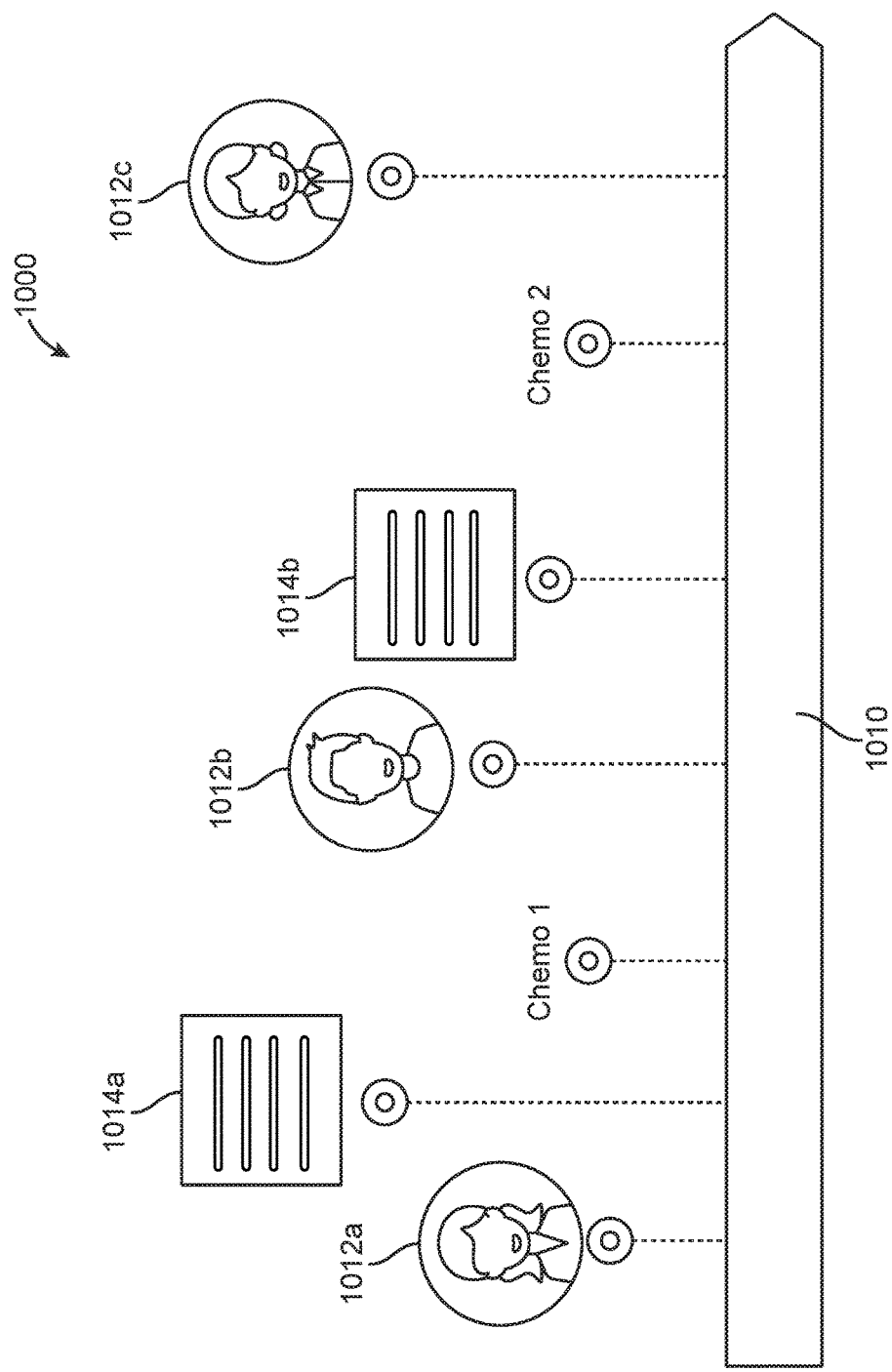

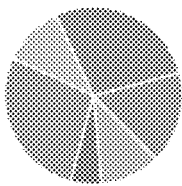
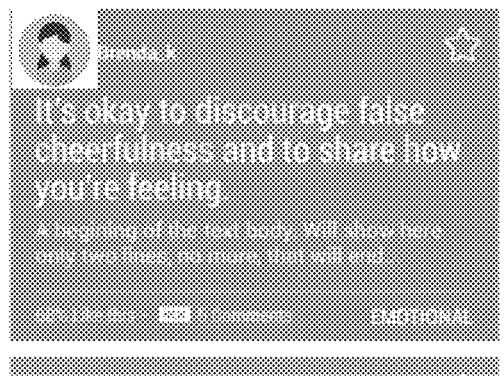
FIG. 23

Wait until you're certain about your diagnosis to tell your children

Oncologist Consultancy                                        KIDS

 Noa                          175 votes  1,722 views

You may want to wait to tell your children until your diagnosis has been confirmed. Having a general idea of your prognosis and treatment course will help you explain the situation and provide reassurance to your children. Cancer treatment can vary considerably in terms of side effects and length of treatment and the more you are able to communicate that a path exists that is meant to lead to recovery - the less anxiety this conversation will create.
For more on how to communicate cancer to children, go here:
- American Cancer Society
- Cancer.net
- MD Anderson

FIG. 26

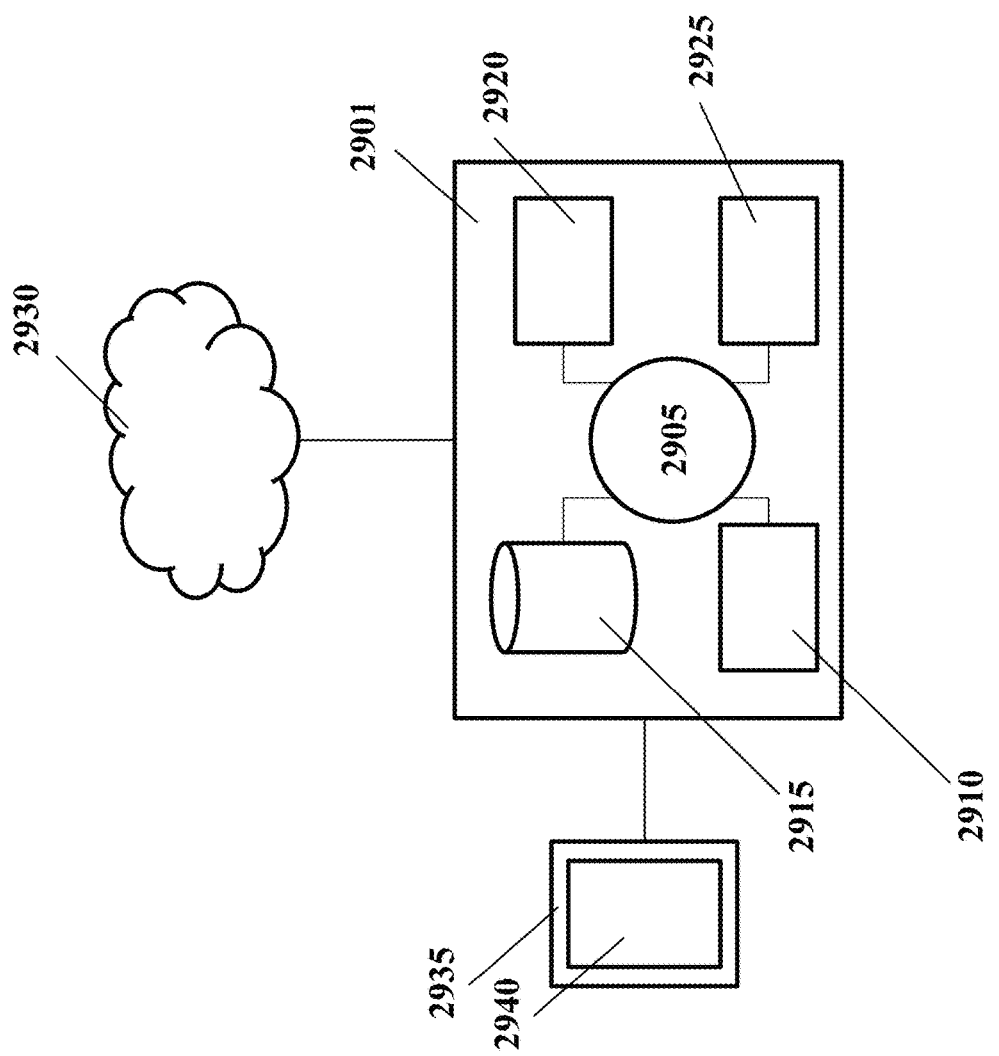

METHODS AND SYSTEMS FOR DYNAMICALLY GENERATING REAL-TIME RECOMMENDATIONS

CROSS-REFERENCE

This application is a continuation application of U.S. application Ser. No. 15/217,878, filed on Jul. 22, 2016, which claims the benefit of U.S. Provisional Application Ser. No. 62/195,762, filed on Jul. 22, 2015 and U.S. Provisional Application Ser. No. 62/196,142, filed on Jul. 23, 2015, which applications are incorporated herein by reference in their entirety.

BACKGROUND

When people experience a significant life transition (SLT), they often turn to one or more of the following sources of information: (1) search engines, (2) social networks, (3) paid professionals, (4) friends and family, (5) content/media, and/or (6) support groups.

This has some shortcomings. For example, none of the information sources above may be capable of providing proactive guidance to people undergoing SLTs. The information obtained through those information sources may not be personalized. In many instances, a substantial part of the information may not even be relevant or applicable to a person. Furthermore, the practical wisdom of knowledgeable individuals may not be easily accessible/available to those in need because it is typically embedded within a plethora of other irrelevant information. In addition, the existing information sources may not be capable of proactively providing people with answers to questions that even they themselves do not know to ask. Nor are the existing information sources capable of generating a map of SLT milestones on a timeline that is relevant and highly personalized to each person. Thus, existing software solutions may not be personalized to match the person's needs. Although paid professionals can provide professional advice (e.g., legal advice or medical advice), they are often unable to address the non-professional aspects (e.g., emotional well-being of the person) during the SLTs.

Thus, there is a need for a software application that captures valuable community wisdom, makes it accessible, and tells users what they need to know, when they need to know it, thus helping them improve their significant life transitions in a step-wise fashion.

SUMMARY

In some instances, a user may be faced with an event such as a significant life transition. During those moments, the user may lack the experience and tools to make informed decisions at an appropriate time, in a quick and efficient manner.

Accordingly, a need exists to identify an event based on input from the user, and to determine a plurality of milestones associated with the event. Another need exists to provide personalized insights to the user to address each milestone. A further need exists to predict the user's next milestones, so that the insights can be further personalized and dynamically provided in real-time to the user.

The insights may be provided depending on the user's needs at each milestone. The milestones may be charted along a timeline of the event for the user. The insights may be crowd-sourced insights provided by a community of people who have experience going through the event. The insights may be further edited, curated and rated by a group of experts before the insights are provided to the user. The insights, milestones, and timeline can help the user to navigate through an event requiring important decision-making. In addition, the insights, milestones, and timeline can help users to improve their decision-making process, and assist them in making informed decisions at any given moment. The event navigation system disclosed herein addresses at least the above needs.

According to some embodiments of the disclosure, a computer-implemented method for predicting a user's needs is provided. The method includes: receiving input data associated with a user; and predicting the user's needs at a plurality of milestones of a significant life transition (SLT) event associated with the input data associated with the user.

The input data may further include data that is directly inputted by the user. In some embodiments, the input data may be a question. Alternatively, the input data may be an online social interaction. In some embodiments, the SLT event may include at least one from the following group of SLT events: (1) being diagnosed with a terminal illness, (2) going to college, (3) getting married, (4) starting a family, (5) starting a business, (6) getting divorced, (7) preparing for retirement, and (8) relocation to a new place. In some embodiments, the user may be about to go through or may be currently going through at least one SLT event.

In some embodiments, the predicting may be performed by a predictive algorithm comprising a natural language processing (NLP) technique. In some embodiments, the method may further comprise: extracting a temporal status of the user based on a plurality of factors, wherein the factors comprise a physical location of the user and the user's online social interactions. The temporal status of the user may correspond to a mental state or a physical state of the user at a defined moment in time. The temporal status of the user may be extracted based on thoughts, feelings, opinions, statements, or comments made by the user and the other users during the online social interactions.

In some embodiments, the predicting may be based on dynamically modified milestones along a timeline of the SLT. The plurality of milestones may correspond to future events associated with the SLT event. The plurality of milestones may occur in series and/or in parallel.

In some embodiments, the method may further include: identifying a community of other users associated with the SLT event, wherein the community of users are: (1) about to experience, (2) currently experiencing, or (3) have experienced one or more of the plurality of milestones. The method may further include: collecting wisdoms of the community of other users, and delivering the wisdoms to the user based on the input data. In some embodiments, the method may further include: customizing user feeds based on the plurality of milestones and the user's needs; and providing the user feeds to the user.

In some embodiments, the method may further include: predicting the user's experience of a future milestone. The method may further include: predicting a time at which the user will experience a future milestone. The method may further include: providing user feeds that are relevant to the future milestone, at the time at which the user will experience a future milestone.

According to some embodiments, a computer-implemented method for matching data, the method is provided. The method includes: receiving a plurality of insights; and matching each of the plurality of insights to one or more milestones, wherein each milestone is associated with a significant life transition (SLT) event. The matching may include analyzing one or more of the following factors comprising a crowd-sourced rating of each insight, a credentials rating of each contributor, or a popularity rating of each insight or contributor.

The method may further include: matching each of the insights that is matched with one or more milestones with one or more preselected topics. The one or more topics may be selected from a group comprising of: work, treatment and symptoms, support services, specialist referral, medical information, kids, insurance and coverage, friends and family, financial advice, emotional, communicating with doctors, or unclassified topics. In some embodiments, the plurality of insights may be provided by a plurality of contributors possessing experience or knowledge relating to the plurality of milestones and needs.

In some embodiments, the factors may further comprise a frequency at which each matched insight appears for the corresponding milestone. The method may further comprise: ranking the matched insights based on their frequencies of appearance.

In some embodiments, the plurality of insights and milestones may be provided on a timeline of the SLT event. In some embodiments, the plurality of insights may be matched dynamically and modified in real-time on the timeline as the event progresses along the timeline. The method may further include: providing the matched insights to a plurality of curators for curation; and receiving the curated insights from the curators. The plurality of curators may be predetermined to possess a predetermined level of experience or knowledge relating to at least one of the SLT events. The plurality of curators may be peer-reviewed. In some embodiments, the plurality of curators may be peer-reviewed based on a credentials rating of each curator, a popularity rating of each curator, or a number of user-followers of each curator. In some embodiments, a score may be assigned to each curated insight by each curator.

According to some further embodiments, a computer-implemented method is provided. The method comprises: delivering feeds associated with one or more milestones of a significant life transition (SLT) event to a user in a time-sensitive, location-dependent, and content appropriate manner, based on information obtained from the user concerning the SLT event. In some embodiments, timing of the delivering of the feeds may be determined using a predictive model to assess future milestones of the SLT event. In some embodiments, a quantity, a type, and/or a source of the feeds may be based upon a determination of the user's profile. In some embodiments, the feeds delivered may be selected based on a location of the user at a time of the delivering of the feeds. In some embodiments, the feeds delivered may be ranked according to a plurality of factors associated with the feeds. The plurality of factors may include the number of times each feed has been viewed, a rating of each feed by a community of users, and a number of comments for each feed.

In some embodiments, the feeds may be based on community wisdom. The community wisdom may comprise knowledge that has been reviewed and approved by a community of people having experience with the corresponding SLT event. In some embodiments, the feeds may be provided for a plurality of milestones on a time-line that is specific to the user's journey through the SLT event, and wherein the plurality of milestones may be associated with the SLT event.

In some embodiments, the feeds may be configured to address the user's needs at each milestone of the user's journey through the SLT event. In some embodiments, the feeds may be dynamically provided for the corresponding milestones on the time-line. In some embodiments, the feeds may be modified in real-time on the timeline as the SLT event progresses along the timeline.

According to some other embodiments, a computer-implemented method for mapping a user's journey through a significant life transition (SLT) event is provided. The method comprises: providing a plurality of milestones associated with each of a plurality of different SLT events thereby creating a plurality of journeys, wherein each milestone is editable either directly or indirectly by a community of users.

In some embodiments, the plurality of milestones may be selectable by the user, to allow the user to observe effects of selecting different milestones on the user's journey. In some embodiments, the milestones may be provided as objects in computer-generated graphical user interfaces. The objects may be movable using a drag-and-drop feature in the computer-generated graphical user interfaces.

In some embodiments, the objects may be interconnected in series and/or in parallel in the computer-generated graphical user interfaces. At least some of the objects may be capable of being expanded into a plurality of different objects. Alternatively, at least some of the objects may be capable of being collapsed into a single object.

In some embodiments, each milestone may be associated with a set of curated feeds or wisdom derived from a community of users. A user's journey may comprise a plurality of different sub journeys depending on which milestone(s) a user selects. In some embodiments, the number of sub journeys that are available to the user may depend at least upon: (1) a number of the milestones, and (2) a number of ways that the milestones can be interconnected.

According to some further embodiments, a computer-implemented method for matching data is provided. The method comprises: filtering a first set of data and a second set of data, wherein the first set of data comprises a plurality of questions relating to a plurality of milestones and needs, and wherein the second set of data comprises a plurality of insights relating to the plurality of milestones and needs; matching the first set of data to the second set of data based on the plurality of milestones and needs; and ranking the matched data based on a plurality of relevance factors.

In some embodiments, the plurality of milestones and needs may be associated with a significant life transition (SLT) event comprising at least one from the following group of SLT events: (1) being diagnosed with a terminal illness, (2) going to college, (3) getting married, (4) starting a family, (5) starting a business, (6) getting divorced, (7) preparing for retirement, and (8) relocation to a new place. The plurality of insights may be provided by a plurality of contributors possessing experience or knowledge relating to the plurality of milestones and needs. In some embodiments, the plurality of questions may be provided by the plurality of contributors. In some embodiments, the plurality of questions may be provided by an information source other than the plurality of contributors. In some embodiments, the plurality of questions may be provided by the plurality of contributors and another information source.

In some embodiments, the method may further comprise: correlating the plurality of questions and insights to the plurality of milestones and needs using a natural language processing (NLP) technique or a machine learning method. In some embodiments, the matched data may be ranked using a relevance ranking technique based on the plurality of relevance factors. In some embodiments, the plurality of relevance factors may comprise a crowd-sourced rating of each insight, a credentials rating of each contributor, or a popularity rating of each insight or contributor.

In some embodiments, matching the first set of data to the second set of data may comprise matching the plurality of questions to the plurality of insights based on the plurality of milestones and needs. In some embodiments, if one or more questions are not matched with the corresponding insights, the method may further comprise: generating requests for insights to the one or more unmatched questions; and sending the requests for insights to the plurality of contributors. In some embodiments, if one or more insights are not matched with the corresponding questions, the method may further comprise: generating questions to the one or more unmatched insights using a natural language processing (NLP) technique or a machine learning method.

It shall be understood that different aspects of the invention can be appreciated individually, collectively, or in combination with each other. Various aspects of the invention described herein may be applied to any of the particular applications set forth below or for any other types of energy monitoring systems and methods.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 illustrates an exemplary insights curation list, in accordance with some embodiments;

FIG. 9 illustrates an exemplary curation window, in accordance with some embodiments;

FIG. 10 illustrates an exemplary timeline window, in accordance with some embodiments;

FIG. 23 illustrates an exemplary chemotherapy milestone, in accordance with some embodiments;

FIG. 26 illustrates an exemplary insight, in accordance with some embodiments;

FIG. 29 shows a computer control system that is programmed or otherwise configured to implement methods provided herein.

DETAILED DESCRIPTION

Figure 1:
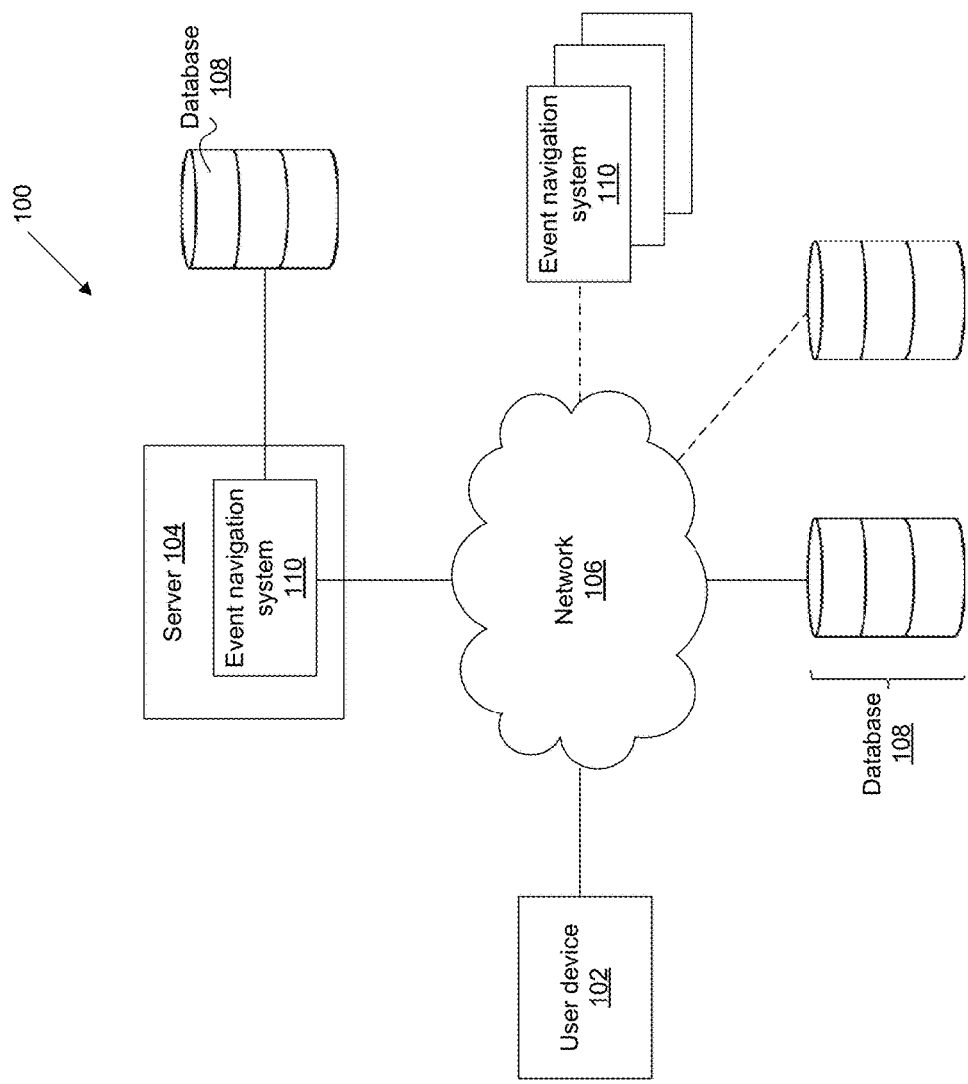
FIG. 1 illustrates an exemplary network layout, in accordance with some embodiments.

Reference will now be made in detail to some exemplary embodiments of the invention, examples of which are illustrated in the accompanying drawings. Wherever possible, the same reference numbers will be used throughout the drawings and disclosure to refer to the same or like parts.

Introduction

In life, people can experience significant life transitions. SLTs can occur in series or in parallel. They can occur as a consequence of a previous or simultaneous SLT. SLTs may be characterized as, or result in, a journey in an individual's life. Such journey can be long or short. They can be simple or complex. A journey can include one or multiple milestones. A SLT can result in other SLTs or journeys (e.g., loss of a partner can lead to depression or other mental illness). Non-limiting examples of SLTs may include starting and/or attending college, getting married, having children, starting a business, getting divorced, retirement, relocation, or being diagnosed with a serious/chronic illness. (See, e.g., FIGS. 3 and 4).

When an SLT occurs, one generally lacks the required experience to make the best decisions, at the right time, quickly and efficiently. Indeed, when one searches the internet for information to help one make the right decisions, one finds the information available to be unstructured, not personalized, not fitting to the specific problem or issue at hand, and/or nor available in a timely manner.

The present disclosure solves this problem, by providing an event navigation system that makes collective community wisdom accessible to a user in need of such advice. The term "user" or "end user" as used herein may refer to individuals who are about to go through, or are currently going through, an event such as a significant life transition. These are individuals who generally need help with navigating the SLT. Wisdom as used herein may refer to time-sensitive, location-dependent, and content appropriate advice on what a person should know regarding a SLT and/or any of its milestones. Wisdom may include insights and advice from other people who have had the same or are experiencing the same SLT. In particular, the system can provide users with information they need to know, when they need to know it, as the users go through different milestones of an SLT. Accordingly, the system can help users to make informed decisions, and help them to optimally navigate through the SLTs by anticipating their needs at different milestones during the journey.

As mentioned above, the system can make collective community wisdom accessible to a user in need of such advice. Wisdom may be derived using any one or more of the methodologies described herein.

Deriving Wisdom

In some instances, wisdom can be derived using the following four-step process, which can be performed in whole or in part by the system.

First, data may be collected. Data may include discrete, objective facts about an event. The discrete, objective facts may be collected from institutions approved by the system or key opinion leaders (KOLs). Examples of KOLs may include doctors, psychiatrists, psychologies, and other professionals known to practice in a certain field or SLT. Other examples of KOLs may include individuals who have a significant number of followers in a certain field or SLT. The institutions can include for example, corporate institutions, non-profit institutions or non-government organizations. Examples of institutions may include the National Institute of Health (NIH), pharmaceutical companies, and other fundraising organizations whose mission is to help individuals with a certain SLT.

Data may also include subjective thoughts, feelings and opinions about an event by other users. Subjective thoughts, feelings and opinions may be collected from forums, blogs, message posts/threads, etc. Data may come in a disorganized, unstructured and unfiltered form, and may contain both useful data as well as irrelevant data. Data may be searched using machines capable of performing keyword searches.

Second, data may be sorted and filtered into information. Data may be filtered by categorizing and condensing the data into information that has added value. For example, irrelevant data may be removed by filtering. Information can be categorized into different topics and domains.

Third, knowledge may be extracted from information. Knowledge may be extracted by comparing, contextualizing, and connecting relevant information. Knowledge may include user's experiences of an event. Knowledge may include users' insights on particular events and milestones. Insights may include advice, comments, opinions, thoughts and/or feelings about particular milestones. Insights may be contributed by an alumnus or SLT alumnus. The alumnus or SLT alumnus may refer to individuals who have experienced or are experiencing a certain SLT. In some instances, the alumnus or SLT alumnus may be experts in a certain SLT.

In some instances, knowledge can be obtained from a KOL editorial community. The members of the community may be encouraged or may provide information about an SLT or a particular milestone of an SLT. The system can cluster insights that are of similar content.

Fourth, wisdom may be derived from knowledge. Wisdom may be derived by curating and editing the knowledge. The knowledge may be reviewed and approved by a curator. A curator may refer to an individual who uses the system to curate, filter, approve/reject, edit, score and/or rank the insights. The system can collect curated knowledge and convert it into wisdom. Wisdom may include the application of knowledge to a specific event and user at a defined point in time.

Disseminating Wisdom

After wisdom has been derived, the wisdom may be disseminated to a user. The system can predict the user's present and future needs by analyzing user input in real-time. Based on those needs, the system can generate a user's SLT timeline comprising a plurality of milestones. The system can map knowledge to the different milestones, based on the user's predicted needs and the user's SLT timeline. The mapped knowledge may collectively constitute wisdom. In a sense, the mapped knowledge is the wisdom of a community of people. The wisdom may include personalized recommendations to the user about a particular event of an SLT—for example, what the user wants to know, needs to know, what are things to consider, what actions to take for that event, and when to take those actions. Accordingly, the system can dispense the wisdom to a user in need in a time-sensitive, location-dependent, content appropriate manner.

Next, various embodiments of the system will be described as follows.

In some embodiments, the system can provide users' needs for proactive community-based guidance. The system can personalize and customize the guidance to each user. The system can be configured to harness the accumulated experiences of other users in the community to offer step-by-step guidance to users who are presently going through the SLTs. The system can also generate optimal routes for navigating the SLTs, that can benefit specific users, at specific times and localities. Accordingly, the system can provide personalized guidance to a user based on the user's timeline, milestones, geographical location, and/or other aspects (e.g. age, ethnicity, gender, genetic disposition, user personality, moods, interests, etc.).

The system may be a dynamic platform for capturing and generating community wisdom, that is capable of proactively informing users and their families on what they need to know—when they need to know it, as they navigate through a life transition. In addition to a highly personalized insights feed, the system can offer a global positioning system (GPS)-like map containing a timeline of various milestones. Users can query the system, and the system can direct the user's question at a targeted set of community contributors who are likely to have insights. The wisdom captured may be a result of a collaborative process done by and for users with a built-in editorial hierarchy. The hierarchy may include passive content consumers and volunteer community curators. The insights may be edited, curated and rated to ensure its quality, before it is provided to the user. The editing and curation collectively constitutes an information filtering process through which community wisdom can be extracted.

The system can draw on the wisdom of communities to several ends: gathering insights, curating the insights, and distributing the insights. The system may distribute the insights via web plugins. Communities have the know-how, motivation and social interactions that the users are looking for. When engaging the communities, the system can implement an editorial hierarchy (contributors/editors). The crowd-sourced community content can allow the users to have personalized tailor-made answers by location, ethnicity, religion and/or other relevant criteria.

The system may utilize machine learning and natural language processing (NLP) technologies as described elsewhere herein. The system can convert and cluster masses of overlapping and possibly contradictory text-based insights into quantifiable, time-based, actionable and parameterized tips. Once entered into the platform, those tips may be matched to specific user profiles at specific stages of each user's unique journey using an exemplary recommendation engine's predictive analytics. Accordingly, the platform is applicable to any SLT, where journey 'alumni' have information to contribute to journey 'newcomers'. As such, the system can capture, curate and personalize the wisdom of communities—to allow users to better navigate through significant life transitions from childhood to seniority.

In some embodiments, the system can calculate the spending needs of SLTs, by receiving community recommendations on how to optimally direct the users' out-of-pocket expenses. Organic community insights can recommend and anticipate the purchase of goods and services that users need, and when they need it. For example, in the case of a SLT such as breast cancer, the system may be able to determine that 30% of all user insights are expense-related, which may be typical of coping with such a life transition. Based on insights from the community, the system may further identify over 180 product/services categories that patients should use, and recommend when to use them. In some instances, revenue may be generated by the system through referrals, native advertising (CPM), and/or content marketing (CPC).

Next, examples of SLTs and how a user can use the system to navigate the SLTs will be described. It is noted that the following examples are merely exemplary, and that the system can be used in numerous other applications involving event navigation and decision-making.

Applications Example 1 (Diagnosis with Cancer)

For example, a person going through a SLT of having been diagnosed with cancer may wonder how to proceed with treatment. A journey to overcome cancer thus begins. The individual can "ask" the community for advice about cancer treatment. Various members of the community may make comments regarding the cancer treatment. The application collects the comments as data and filters out the relevant information. For example, the relevant information may pertain to the specific type and stage of cancer that the person is going through. In addition, the application may collect other relevant information on cancer treatment from reputable sources such as the American Cancer Society.

Next, the application extracts knowledge from information. The knowledge may include the contributors' personal experience or knowledge about the cancer treatment. For example, the knowledge may include their insights on particular events and milestones relating to the cancer treatment.

Next, the knowledge is provided to curators for curation and editing. The curators may have extensive experience or knowledge about cancer treatment, and are qualified by the application to accept, deny, and/or rate the insights. The curators may be KOLs on cancer treatment.

Wisdom is derived from the curated knowledge. The application can apply the wisdom to a particular event and a specific user for a defined point in time. For example, the application can educate the user on the types of cancer treatment, recommend a suitable type of cancer treatment for the user, suggest medical providers that fit the user's budget/needs, provide advice on side effects resulting from the cancer treatment, as well as other non-clinical aspects of the cancer treatment (e.g., impact on family, finances, job, etc.). Accordingly, the individual is then given the "wisdom" of the community through the application.

Applications Example 2 (Making a Career Switch to a Different Field)

A person going through a SLT of looking to make a career switch to a different field may wonder how to prepare himself for the new field, and what it is like to work in the new field. For example, the person may be an engineer who is looking to switch to the field of patent law. A journey of job preparation thus begins. The individual can "ask" the community for advice on how to switch from being an engineer to being a patent agent/lawyer. Various members of the community may make comments regarding their own experience. For example, certain members of the community may be former engineers who have successfully switched to the field of patent law. Alternatively, certain members may be individuals who made the switch to patent law but reverted back to being an engineer. The application collects the comments as data and filters out the relevant information. For example, the relevant information may pertain to the field of engineering that the person is currently is, and the type of patent law that the person intends to practice (e.g., patent prosecution or patent litigation). In addition, the application may collect other relevant information on the field of patent law from reputable sources such as the American Intellectual Property Law Association.

Next, the application extracts knowledge from information. The knowledge may include the contributors' personal experience about their career switch from engineering to patent law. For example, the knowledge may include their insights on particular events and milestones relating to how to prepare for the switch and when to switch to the new field.

Next, the knowledge is provided to curators for curation and editing. The curators may have extensive experience or knowledge about engineering and patent law, and are qualified by the application to accept, deny, and/or rate the insights. The curators may be KOLs on both engineering and patent law. For example, the curators may be in-house counsels of engineering companies, distinguished patent lawyers, etc.

Wisdom is derived from the curated knowledge. The application can apply the wisdom to a particular event and a specific user for a defined point in time. For example, the application can educate the user on what the field of patent law entails, how to make the switch from engineering to patent law, when to make the switch, suggest ways to prepare for and pass the patent bar exam, provide a list of law schools that have reputable patent law programs, as well as other aspects of the career switch (e.g., finances, law school tuition, relocation, etc.). Accordingly, the individual is then given the "wisdom" of the community through the application.

Applications Example 3 (Preparing for Loss of a Loved One)

A person going through a SLT of losing a loved one may wonder about how to brace the family together during those difficult times, how to inform friends and family about the loss, and how to prepare for the funeral. A journey of preparing for the above thus begins. The individual can "ask" the community for advice on how they deal with the loss of their loved ones and matters relating to the funeral. Various members of the community may make comments regarding their own experience. For example, certain members of the community may share their experiences on how they pulled their family together during those difficult times, the funeral preparation, the wrapping up of the deceased loved one's matters, etc. The application collects the comments as data and filters out the relevant information. For example, the relevant information may pertain to the age, gender, and ethnicity of the deceased family member, how the deceased family member passed away, the size of their immediate and extended family, the community in which the deceased family member lived, the legacy/impact that the deceased family member left behind, assets and other matters that the deceased family member left behind, etc. In addition, the application may collect other relevant information on how to prepare for the loss of a loved one, for example advice from friends, family and support groups.

Next, the application extracts knowledge from information. The knowledge may include the contributors' personal experiences about they dealt with the loss of a loved one. For example, the knowledge may include their insights on particular events and milestones relating to the loss of a loved one (e.g., when and which mortuary to go to, when and where to hold the funeral, how to inform family and friends, how they encouraged their family during those difficult times, and matters to attend to after the funeral).

Next, the knowledge is provided to curators for curation and editing. The curators may have extensive experience or knowledge about how to deal with the loss of a loved one, and are qualified by the application to accept, deny, and/or rate the insights. For example, the curators may be family counsels, religious leaders such as rabbi or pastors, lawyers specializing in wills and trusts, etc.

Wisdom is derived from the curated knowledge. The application can apply the wisdom to a particular event and a specific user for a defined point in time. For example, the application can educate the user on the various aspects of managing the loss of a loved one. Accordingly, the individual is then given the "wisdom" of the community through the application.

Next, various embodiments of the invention will be described with reference to the drawings.

FIG. 1 illustrates an exemplary network layout 100 in accordance with some embodiments. In one aspect, network layout 100 may include user device 102, server 104, network 106, database(s) 108, and event navigation system(s) 110. Each of the components 102, 104, 108, and 110 may be operatively connected to one another via network 106 or any type of communication links that allows transmission of data from one component to another.

User device 102 may be, for example, one or more computing devices configured to perform one or more operations consistent with the disclosed embodiments. For example, user device 102 may be a computing device that can display one or more webpages. User device 102 can include, among other things, desktop computers, laptops or notebook computers, mobile devices (e.g., smart phones, cell phones, personal digital assistants (PDAs), and tablets), and wearable devices (e.g., smartwatches). User device 102 can also include any other media content player, for example, a set-top box, a television set, a video game system, or any electronic device capable of providing or rendering data. User device 102 may include known computing components, such as one or more processors, and one or more memory devices storing software instructions executed by the processor(s) and data.

In certain embodiments, one or more users may operate user device 102 to perform one or more operations consistent with disclosed embodiments. Alternatively, a user may operate one or more user devices 102 to perform one or more operations consistent with disclosed embodiments. A user as described herein may refer to an individual, a group of individuals, a support group comprising a group of individuals, a common interests group comprising a group of individuals, etc. The support group may be, for example, a group of people sharing their experiences how dealing with a significant life transition (e.g., diagnosed with a terminal illness, going through a divorce, etc.). The common interests group may be, for example, a group of people who have common goals or interests or a common timeline (e.g., going to college, or upcoming retirement, etc.). A user may be registered or associated with an entity that provides services associated with one or more operations performed by the disclosed embodiments. For example, the user may be a registered user of an entity (e.g., a company, an organization, an individual, etc.) that provides one or more of servers 104, database(s) 108, and/or event navigation system(s) 110 to perform operations for assisting the user in navigating through events happening in the user's life, the operations being consistent with certain disclosed embodiments. The events may be related to significant life transitions (SLTs), as described below.

User device 102 may be configured to receive input from one or more users. A user may provide may provide an input to user device 102 using an input device, for example, a keyboard, a mouse, a touch-screen panel, voice recognition and/or dictation software, or any combination of the above. The user input may include questions, comments, or statements made by one or more users. Different users may provide different input, and the input may relate to any subject matter. For example, a user may be going through a significant life transition (SLT), such as going to college, getting married, having children, starting a business, getting divorced, retirement, relocation, or diagnosed with a terminal illness, among others. In those instances, the user's input may be indicative of the user's thoughts, feelings, moods, opinions, general questions regarding any of the above-mentioned SLTs, and/or specific questions regarding certain topics within a SLT.

In some embodiments, a plurality of user devices 102 may be provided. One or more users may be associated with each user device 102. Alternatively, one or more devices 102 may be associated with each user. The disclosed embodiments are not limited to any specific relationships or affiliations between user(s) of device 102 and an entity, person(s), or entities providing server 104, database(s) 108, and event navigation system(s) 110.

Server 104 may be one or more server computers configured to perform one or more operations consistent with disclosed embodiments. In one aspect, server 104 may be implemented as a single computer, through which user device 102 is able to communicate with other components of network layout 100 illustrated in FIG. 1. In some embodiments, user device 102 may communicate with server 104 through network 106. In other embodiments, server 104 may communicate on behalf of user device 102 with event navigation system(s) 110 or database(s) 108 through network 106. In some embodiments, server 104 may embody the functionality of one or more of event navigation system(s) 110. In some embodiments, event navigation system(s) 110 may be implemented inside and/or outside of server 104. For example, event navigation system(s) 110 may be software and/or hardware components included with server 104 or remote from server 104.

In some embodiments, user device 102 may be directly connected to server 104 through a separate link (not shown in FIG. 1). In certain embodiments, server 104 may be configured to operate as a front-end device configured to provide access to one or more event navigation system(s) 110 consistent with certain disclosed embodiments. Server 104 may, in some embodiments, utilize event navigation system(s) 110 to process user input from user device 102 in order to determine the user's milestones and needs, and to provide personalized answers and/or recommendations to the user based on those milestones and needs. Server 104 may be configured to search, retrieve, and analyze data and information stored in database(s) 108. The data and information may include questions, answers, comments, and insights relating to different SLTs, milestones and/or the user's needs. While FIG. 1 illustrates server 104 as a single server, in some embodiments, multiple devices may implement the functionality associated with server 104.

Server 104 may include a web server, an enterprise server, or any other type of computer server, and can be computer programmed to accept requests (e.g., HTTP, or other protocols that can initiate data transmission) from a computing device (e.g., user device 102) and to serve the computing device with requested data. In addition, server 104 can be a broadcasting facility, such as free-to-air, cable, satellite, and other broadcasting facility, for distributing data. Server 104 may also be a server in a data network (e.g., a cloud computing network).

Server 104 may include known computing components, such as one or more processors, one or more memory devices storing software instructions executed by the processor(s), and data. Server 104 can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers.

While FIG. 1 illustrates server 104 as a single server, in some embodiments, multiple devices may implement the functionality associated with server.

Network 106 may be a network that is configured to provide communication between various components of network layout 100 depicted in FIG. 1. Network 106 may be implemented, in some embodiments, as one or more networks that connect devices and/or components in network layout 100 for allowing communication between them. For example, as one of ordinary skill in the art will recognize, network 106 may be implemented as the Internet, a wireless network, a wired network, a local area network (LAN), a Wide Area Network (WANs), Bluetooth, Near Field Communication (NFC), or any other type of network that provides communications between one or more components of network layout 100. In some embodiments, network 106 may be implemented using cell and/or pager networks, satellite, licensed radio, or a combination of licensed and unlicensed radio. Network 106 may be wireless, wired, or a combination thereof.

Event navigation system(s) 110 may be implemented as one or more computers storing instructions that, when executed by processor(s), process user input from user device 102 in order to determine the user's milestones and needs, and to provide personalized answers and/or recommendations to the user based on those milestones and needs. Event navigation system(s) 110 may search, retrieve, and analyze data and information stored in database(s) 108. The data and information may include questions, comments, and insights relating to different SLTs, milestones and/or the user's needs. In some embodiments, server 104 may be the computer in which event navigation system(s) 110 are implemented.

However, in some embodiments, at least some of event navigation system(s) 110 may be implemented on separate computers. For example, user device 102 may send a user input to server 104, and server 104 may connect to event navigation system(s) 110 over network 106 to retrieve, filter, and analyze data from database(s) 108. In other embodiments, event navigation system(s) 110 may represent software that, when executed by processor(s), perform processes for determining the user's needs, and providing personalized answers and/or recommendations to the user based on those needs.

For example, server 104 may access and execute event navigation system(s) 110 to perform one or more processes consistent with the disclosed embodiments. In certain configurations, event navigation system(s) 110 may be software stored in memory accessible by server 104 (e.g., in memory local to server 104 or remote memory accessible over a communication link, such as network 106). Thus, in certain aspects, event navigation system(s) 110 may be implemented as one or more computers, as software stored on a memory device accessible by server 104, or a combination thereof. For example, one event navigation system(s) 110 may be a computer executing one or more matching techniques, and another event navigation system(s) 110 may be software that, when executed by server 104, performs one or more event navigation techniques.

The event navigation system(s) 110 can assist a user in navigating events happening in the user's life. As previously described, such events may be related to significant life transitions (SLTs), for example, going to college, getting married, having children, starting a business, getting divorced, retirement, relocation, or diagnosed with a terminal illness, among others. Event navigation system(s) 110 may be configured to perform event navigation for the user using a plurality of ways. For example, one of event navigation system(s) 110 may store and/or execute software that performs an algorithm for processing user input, identifying an event from the user input, and determining relevant milestone(s) and need(s) associated with the event. Another of event navigation system(s) 110 may store and/or execute software that performs an algorithm for defining and classifying a plurality of topics relating to those milestone(s) and need(s). Another of event navigation system(s) 110 may store and/or execute software that performs an algorithm for searching and extracting questions stored in one of database(s) 108 relating to those topics/milestone(s). Another of event navigation system(s) 110 may store and/or execute software that performs an algorithm for searching and extracting insights and comments stored in one of database(s) 108 relating to those topics or milestone(s). Another of event navigation system(s) 110 may store and/or execute software that performs an algorithm for filtering the questions and insights, and matching the filtered questions/insights to the user's needs/milestones. Another of event navigation system(s) 110 may store and/or execute software that performs an algorithm for sorting the matched insights/questions, and providing personalized recommendations to the user based on the user's milestones, timeline and needs. The disclosed embodiments may be configured to implement event navigation system(s) 110 such that a variety of algorithms may be performed for performing one or more event navigation techniques. Although a plurality of event navigation system(s) 110 have been described for performing the above algorithms, it should be noted that some or all of the algorithms may be performed using a single event navigation system 110, consistent with disclosed embodiments.

User device 102, server 104, and event navigation system(s) 110 may be connected or interconnected to one or more database(s) 108. Database(s) 108 may be one or more memory devices configured to store data. Additionally, database(s) 108 may also, in some embodiments, be implemented as a computer system with a storage device. In one aspect, database(s) 108 may be used by components of network layout 100 to perform one or more operations consistent with the disclosed embodiments.

In one embodiment, database(s) 108 may comprise storage containing a variety of data sets consistent with disclosed embodiments. For example, database(s) 108 may include, for example, data from the internet. The data may include lists of questions and answers relating to SLTs that may be obtained from reputable/reliable websites, or the like. For example, if a SLT relates to cancer, the questions and answers may be obtained from a reputable website operated by the American Cancer Society. In some embodiments, database(s) 108 may include crowd-sourced data comprising comments and insights relating to SLTs obtained from internet forums and social media websites. The Internet forums and social media websites may include personal and/or group blogs, Facebook™, Twitter™, Reddit™, etc. Additionally, in some embodiments, database(s) 108 may include crowd-sourced data comprising comments and insights relating to SLTs, whereby those comments and insights are directly input by one or more contributors into the event navigation system(s) 110. The crowd-sourced data may contain up-to-date or current information on SLTs, how to handle SLTs, milestones in each SLT, etc. The crowd-sourced data may be provided by other users or contributors who have experience with those SLTs. For example, those users or contributors may be currently undergoing a SLT, about to complete a SLT, or completed a SLT. It is noted that those users or contributors may be at different phases within a SLT.

In certain embodiments, one or more database(s) 108 may be co-located with server 104, may be co-located with one another on network 106, or may be located separately from other devices (signified by the dashed line connecting one of database(s) 108). One of ordinary skill will recognize that the disclosed embodiments are not limited to the configuration and/or arrangement of database(s) 108.

Any of user device 102, server 104, database(s) 108, or event navigation system(s) 110 may, in some embodiments, be implemented as a computer system. Additionally, while network 106 is shown in FIG. 1 as a "central" point for communications between components of system 100, the disclosed embodiments are not so limited. For example, one or more components of network layout 100 may be interconnected in a variety of ways, and may in some embodiments be directly connected to, co-located with, or remote from one another, as one of ordinary skill will appreciate. Additionally, while some disclosed embodiments may be implemented on server 104, the disclosed embodiments are not so limited. For instance, in some embodiments, other devices (such as event navigation system(s) 110 and/or database(s) 108) may be configured to perform one or more of the processes and functionalities consistent with the disclosed embodiments, including embodiments described with respect to server 104.

Although particular computing devices are illustrated and networks described, it is to be appreciated and understood that other computing devices and networks can be utilized without departing from the spirit and scope of the embodiments described herein. In addition, one or more components of network layout 100 may be interconnected in a variety of ways, and may in some embodiments be directly connected to, co-located with, or remote from one another, as one of ordinary skill will appreciate.

Figure 2:
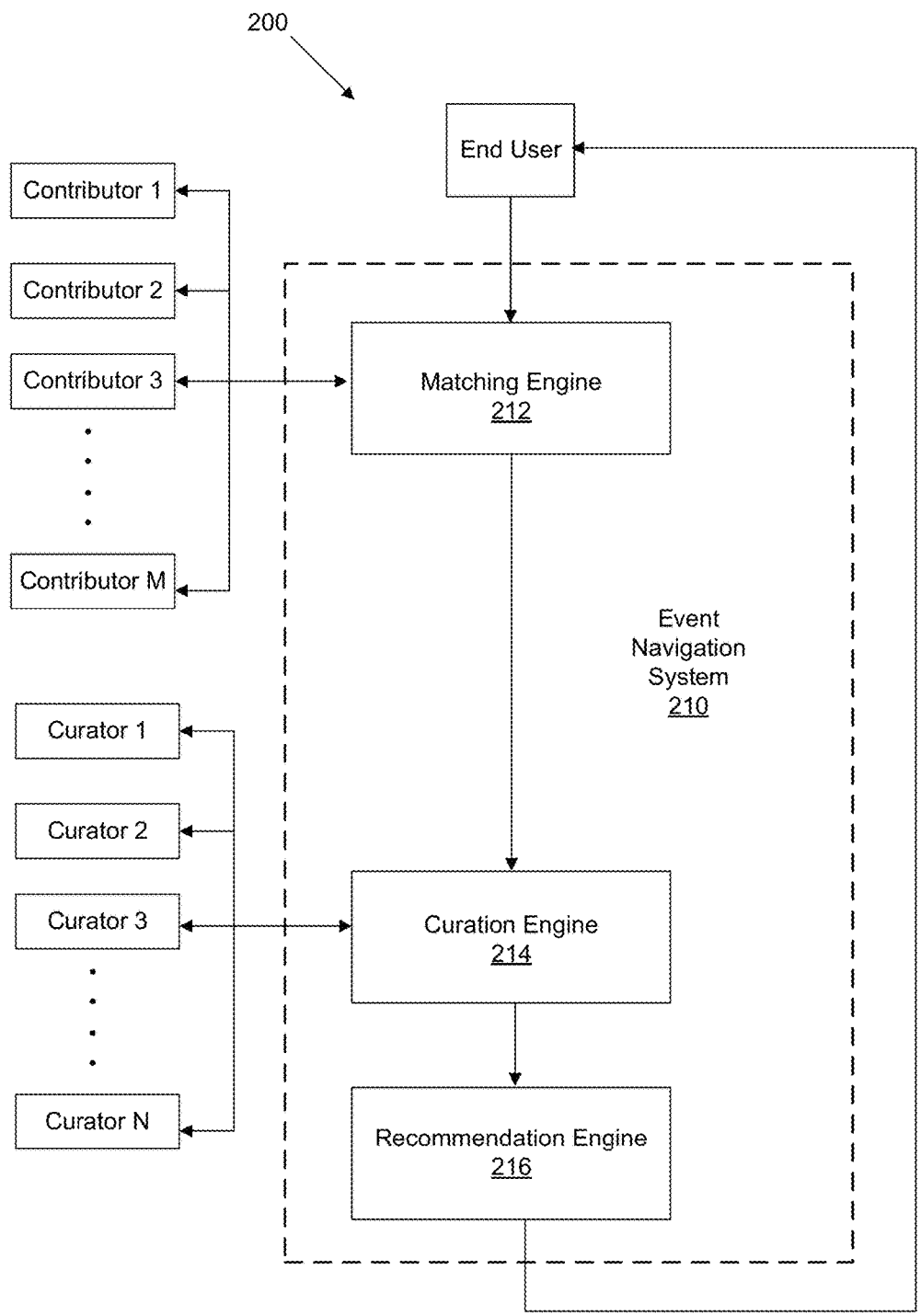
FIG. 2 illustrates components in an exemplary event navigation system, in accordance with some embodiments.

FIG. 2 illustrates exemplary components in event navigation system(s) 110 in accordance with some embodiments. As previously described, event navigation system(s) 110 may be implemented both inside and/or outside of server 104. For example, event navigation system(s) 110 may be software and/or hardware components included with server 104, or remote from server 104.

Referring to FIG. 2, an event navigation system 210 may include a matching engine 212, a curation engine 214, and a recommendation engine 216. One or more of the matching engine, curation engine, and recommendation engine may include natural language processing (NLP) clustering and/or machine learning capabilities, as described elsewhere herein.

The matching engine may be configured to receive a query from an end user. The user query may be provided to the matching engine using one or more user devices. In some instances, the user query may be provided in plural, and may comprise a plurality of user queries. The user query may include questions, comments, or statements made by one or more users. Different users may provide different queries, and the queries may relate to any subject matter. For example, a user may be going through a significant life transition (SLT), such as going to college, getting married, having children, starting a business, getting divorced, retirement, relocation, or diagnosed with a terminal illness, among others. In those instances, the user query may be indicative of the user's thoughts, feelings, moods, opinions, comments, worries, general questions regarding any of the above-mentioned SLTs, and/or specific questions regarding certain topics or milestones within a SLT. Any type or form of user query may be contemplated. The user query may include text, emoticons, pictures, photographs, videos, audio files, etc. The matching engine may be further configured to receive an insight from a contributor. A contributor may be a person who has experience with a SLT, has gone through a SLT, or who is currently going through a SLT. The SLT may include going to college, getting married, having children, starting a business, getting divorced, retirement, relocation, or diagnosed with a terminal illness, among others.

The insight may relate to the contributor's personal experience navigating one or more milestones of a SLT. The contributor's insight may be provided to the matching engine using one or more user devices. In some instances, there may be a plurality of contributors. For example, there may be M contributors, as shown in FIG. 2, where M may be an integer greater than 1. Each contributor may provide an insight to the matching engine. Different contributors may have different insights, and the insights may relate to different milestones or events in the SLT. The insights may be indicative of the contributors' experiences regarding the different milestones. For example, in a case whereby the SLT is a terminal illness, contributor 1 may share an insight relating to types of medical treatment, contributor 2 may share an insight relating to costs of medical treatment, contributor 3 may share an insight relating to emotional support and well-being, etc. Any type or form of contributor insight may be contemplated. The contributor insight may include text, emoticons, pictures, photographs, videos, audio files, etc.

In some embodiments, end users may add questions about subjects they are interested in. The subjects may relate to SLTs, milestones in the SLTs, events, etc. The matching engine may be configured to receive questions from the end users. The matching engine may employ NLP and machine learning methods to (1) categorize the questions into different subjects, (2) tag the questions, (3) find similar questions or existing answers to those questions, and/or (4) match questions to other users or contributors who may be able to answer those questions. The matching engine may be configured to take into account factors such as user/contributor quality ranking and relevancy. User/contributor quality ranking can indicate a user or contributor's level of involvement in contributing answers and/or insights to a community. The community may include a plurality of users who are currently undergoing a particular SLT. User quality ranking can also indicate a ranking of a user or contributor's previous answers. To determine relevancy, the matching engine may determine whether a user or contributor had experienced the relevant step, and/or whether the user or contributor can be considered to be an expert in a particular subject.

In some embodiments, the matching engine may be configured to categorize insights automatically to one or several domains or milestones using, for example, NLP methods and/or machine learning methods for multiclass and multi-label text categorization. For example, labeled insights may be represented as vectors using bag of words, n-gram or word2vec models and input into a machine learning algorithm such as Support Vector Machine, NB-SVM or ensemble of classifiers. The trained model is then used to classify new insights. Texts are normally preprocessed at the beginning of the process to remove stop words, perform stemming and other standard preprocessing procedures. The dimension of the representation may be reduced using feature selection methods such as greedy forward selection, scoring procedures (Chi2, mutual information, etc.) and other approaches. In some cases, insights may be used to extract aggregated knowledge such as "Top 10 issues/questions about a SLT or a topic", "card packs" that combines several insights about a specific subject, etc. Various NLP methods may be used to this end. In some cases, multiclass or multinomial classification can be used to classify insights into two or more classes (e.g., different milestones, different SLTs, etc.).

In some cases, a multi-label classification problem may arise when an insight is classified into two or more classes, or when multiple insights are classified for a single class. Problem transformation methods and/or algorithm adaptation methods can be implemented by the matching engine to solve the multi-label classification problem. For example, problem transformation methods can be used transform the multi-label problem into a set of binary classification problems, which can then be handled using single-class classifiers. Algorithm adaptation methods can adapt the algorithms to directly perform multi-label classification. In other words, instead of converting the multi-label classification problem to a simpler problem, the algorithm adaptation methods can be configured to address the problem in its full form.

In some cases, a user may not know what questions to ask or how to deal with a SLT. For example, when a user has been diagnosed with a terminal illness, the user may be at a loss because such SLTs typically involve numerous milestones. The milestones may be spread out temporally on a timeline during the course of the SLT. For example, in the case of cancer, there are many well-defined characteristics and stages. Accordingly, the treatment courses for different types/stages of cancer may have well-defined protocols with clear milestones. For example, for stage 2B breast cancer, a possible treatment course may include: (1) surgery, followed by (2) chemotherapy, and followed by (3) long term hormone therapy, depending on genetic characteristics of the tumor. The treatment course may be classified as a milestone that is a medical/treatment event. A milestone may further comprise a plurality of milestones. For example, each step in the cancer treatment course (surgery, chemotherapy, and long term hormone therapy) may be further classified as a milestone or an event occurring at different points in time during the SLT.

A medical/treatment event may be generally described as a clinical event. In addition to clinical events, a user's journey during a SLT (in the case of a terminal illness) may be intermixed with non-clinical events. The non-clinical events may be as meaningful (or sometimes even more meaningful) to the user compared to the clinical events. The non-clinical events may also be classified as milestones. In the case of cancer, the non-clinical events (milestones) may include the user announcing to his family about the disease, informing his employer, selecting a caregiver, shaving his hair prior to chemotherapy, selecting a wig, etc. Unlike the clinical events which typically occur in stages on a preset schedule, the non-clinical events may be even more difficult for the user to navigate. A user may not fully appreciate the nuances and emotional aspects of those non-clinical events, for example, when may be an appropriate time to announce the news to his family or employer, how to deliver the news to them, how to respond to their initial reactions, how to behave around them moving forward, how to promote positive feelings and encouragement, how to strengthen one's will to overcome the disease, etc. In many cases, a user may not even realize the presence or importance of those non-clinical events until it dawns upon them. Accordingly, a user's journey during the SLT may be built around those milestones (both clinical and non-clinical), the timing of those milestones, and the way the user anticipates, prepares, and experiences those milestones. Although users undergoing a same SLT may share some similar milestones, the users may also have other milestones that are unique to each of them. As a result, a user may often be unable to find answers on the internet, to questions relating to all of his milestones. In some instances, as mentioned above, a user may not even realize those milestones exist or what are the right questions to ask. In the case of a terminal illness, there is a need to methodically identify the non-clinical milestones of the user's journey and establish their relationships with the clinical milestones, so as to better assist the user in navigating through the SLT.

The matching engine can methodically identify the non-clinical milestones of the user's journey and establish their relationships with the clinical milestones, by analyzing the user query and contributors' insights using natural language processing (NLP) clustering. By analyzing the query and insights, the matching engine can extract one or more events from the query and insights, and identify the SLT to which those events relate. The matching engine may be used to derive meaning from human or natural language input. In some instances, the matching engine may be configured to derive meaning from pictures, photographs, or videos provided within the user query.

NLP clustering may be based on machine learning, for example statistical machine learning. The statistical machine learning may be based on statistical inference. The matching engine may be configured to automatically identify SLTs and milestones from the user query and contributors' insights. In some embodiments, the matching engine may be configured to learn new metrics associated with SLTs and milestones, by analyzing large corpora of real-world input stored in one or more databases. In some cases, the new metrics may be new milestones that are generated from existing milestones (for example, new forms of treatment in the case of a terminal illness, newly-introduced college entrance exams in the case of going to college, etc.). The matching engine may include statistical models capable of making soft, probabilistic decisions that are based on attaching real-valued weights to each SLT and milestone. The statistical models may be robust to unfamiliar input (e.g. containing words or structures that have not been seen before) and to erroneous input (e.g. with misspelled words or words accidentally omitted).

The matching engine can be configured to generate a timeline of milestones and events in the SLT for the user based on the contributors' insights. The matching engine may be further configured to match the events or needs (determined from the user query) to the timeline of milestones and events. The matching may be performed using NLP clustering or machine learning.

In some embodiments, the matching engine may further analyze a user's previous query in addition to the present query. The previous query may also be indicative of the user's thoughts, feelings, moods, opinions, comments, worries, general questions regarding any of the above-mentioned SLTs, and/or specific questions regarding certain topics or milestones within a SLT. By analyzing the previous query and the present query, the matching engine can establish to a higher probability that the user is undergoing the identified SLT. By extrapolating data from the user's previous and present queries, the matching engine can establish past milestones, determine present milestones, and generate future milestones on the user's timeline for the SLT.

In some embodiments, the event navigation system may include a model that can be used to predict one or more next steps or milestones for a user. The model can be trained using data indicative of the journeys for a plurality of users. Alternatively, the model can be trained using data that is collected as a plurality of users navigate through a same journey or different journeys. The model may be built on machine learning methods such as probabilistic graphical models, temporal sequence analysis, and/or methods incorporating network analysis and graph theory, as described below.

A probabilistic graphical model may use a graph-based representation as a foundation for encoding a complete distribution of various users' journey data over a multi-dimensional space. The probabilistic graphical model may include a graph that is a compact or factorized representation of a set of independences that hold in a specific distribution. Two branches of graphical representations of distributions are commonly used, namely, Bayesian networks and Markov networks. Both families/networks may encompass the properties of factorization and independences, but differ in the set of independences that each can encode, as well as the factorization of the distribution that each induces.

A temporal sequence analysis may be a time series analysis. Such analysis may include methods for analyzing time series data in order to extract meaningful statistics and other characteristics of various users' journey data. Time series forecasting may include the use of the model to predict future values based on previously observed values. In some instances, time series analysis may include the comparison of values of a single time series or multiple dependent time series at different points in time.

Network theory is the study of graphs as a representation of either symmetric relations or, more generally, of asymmetric relations between discrete objects. The objects may correspond to a plurality of users, SLTs, milestones, events, etc. Network theory is a part of graph theory. In other words, the network can be defined as a graph in which nodes and/or edges have different attributes.

Network analysis may include, for example, (1) social network analysis and (2) link analysis. Social network analysis examines the structure of relationships between social entities. These entities are often persons (e.g., users and contributors), but may also be groups, organizations, nation states, web sites, or scholarly publications. Link analysis is a subset of network analysis, and explores associations between different objects. An example may be examining the SLT journeys, milestones, and events of different users during a given timeframe. Link analysis can provide the crucial relationships and associations between many objects of different types that are not apparent from isolated pieces of information. Computer-assisted or fully automatic computer-based link analysis can be performed by the matching engine to determine the relationships between different objects to be analyzed. Links can also be derived from similarity of time behavior in both nodes. Examples may include SLT communities where the links between a plurality of users are determined for example, by the similarity of the SLTs for the plurality of users.

In some embodiments, the matching engine may be configured to implement NLP methods such as named entity recognition to identify commercial entities within user generated content. Examples of entities may include companies, products, services etc.

In some embodiments, the matching engine may be configured to add one or more milestones to a SLT journey for a user, based on suggestions from other users. The suggestions may include one or more suggested milestones. In some instances, a list of suggested milestones may include repeating milestones with identical or similar names. Such methods may include a combination of lexical matching, syntactic parsing trees and relevant ontologies as well as words embedding. Words embedding are vector representation of texts, computed from unlabeled data. Those vectors represent terms in a semantic space. A similarity in that space indicates a sematic similarity between two steps, which we can use to decide that two suggested steps are the same but use different phrasing. NLP and machine learning methods may be used to determine which milestones are unique within the list of suggested milestones. In some cases, voting methods may be used to determine which of the suggested milestones are of value to a community of users. For example, the matching engine may be configured to receive votes from the users on a plurality of suggested milestones, and rank and/or filter the suggested milestones based on the number of votes received.

In one aspect, natural language processing may be performed on a series of words of the explicit declaration to extract one or more key features. The record may be generated to include the extracted key feature(s). The extracted key feature(s) may be used to generate the recommendation rule corresponding to the explicit declaration. The natural language processing may extract key features from series of words and/or converted non-verbal declaration by one or more of generating a parse tree, performing word sense disambiguation, performing named-entity recognition, performing natural language understanding, etc. Key features such as SLTs (e.g., cancer, divorce), person-related words, time-related words, words expressing affinities, and/or context-related words may be extracted therefrom.

In some embodiments, the matching engine may be further configured to retrieve data stored in a database (e.g., database(s) 108). The data may include lists of questions and answers relating to SLTs that are obtained from reputable/reliable websites, or the like. For example, if a SLT relates to cancer, the matching engine may retrieve questions and answers from a reputable website, such as a website operated by the American Cancer Society.

In some embodiments, the data may include crowdsourced data comprising comments and insights relating to SLTs obtained from internet forums and social media websites. The internet forums and social media websites may include personal and/or group blogs, Facebook™, Twitter™, Reddit™, etc. In those embodiments, the matching engine may be configured to retrieve and filter comments and insights from internet forums and social media websites.

In some embodiments, the matching engine may be configured to collect new SLT content from a key opinion leader (KOL) community. The KOL editorial community may comprise bloggers, forums, non-governmental organizations (NGOs), institutions, and/or corporations. In the case of healthcare SLTs, KOLs may refer to influential physicians who are hired by pharmaceutical companies to speak about new therapies to other physicians. Examples of cancer KOLs include top bloggers (e.g. 'booby and the beast'), NGOs (e.g., Imerman Angels), forums (e.g., Facebook groups such as the Young Survivor Coalition), companies (e.g., Treatment Diaries), etc.

In some embodiments, the matching engine may be configured to match the questions and insights to the milestones. A timeline with different milestones may be generated specific to the user's needs. Each milestone on the user's timeline may include questions and insights addressing those questions.

Next, the matching engine 212 may send the matched data to the curation engine 214 for curation and rating. As mentioned above, the matched data may comprise questions and insights that are matched to each milestone.

The curation engine may be configured to determine the frequency at which different insights/questions appear at each milestone. For example, a milestone may have a plurality of questions and related insights. However, the questions may be accessed at different frequencies in the databases. For example, certain questions may be accessed more frequently than other questions. Similarly, some questions may have a large number of insights whereas other questions have fewer insights. Subsequently, the matching engine can filter the matched data based on the frequency at which they appear or are accessed.

After the matched data has been filtered, the curation engine may be configured to provide a preselected set of data to at least one curator for editing, curation and rating. A curator may correspond to an alum, or a person who has extensive knowledge and experience with a SLT. For example, a curator may be someone who has excellent credentials in the relevant field (e.g., a renowned oncologist if the SLT relates to cancer). In some embodiments, a curator may be someone who is highly rated by the community of contributors, for example based on the number of 'likes' and/or positive reviews for the curator (i.e., good peer reviews). Accordingly, the curator may be someone who is qualified to rate the questions/insights for accuracy and relevancy.

The preselected set of data may correspond to questions that are accessed most frequently (e.g., the twenty most-frequently accessed questions for that milestone) and insights that appear most frequently (e.g., the twenty most-frequently appearing insights) for the above questions. Any value for the access frequency may be contemplated. In the example of FIG. 2, the curation engine may provide the preselected set of data to a plurality of N curators, whereby N may be any integer greater than one. The N number of curators may be less than the M number of contributors. For example, in some instances, the curators may constitute about 1% of a community, and the contributors may constitute about 9% of the community, with the users making up the remaining 90% of the community. It should be noted that the embodiments are not limited to the above percentages, and that any proportion of the curators to contributors to users may be contemplated. Each curator may be assigned to evaluate, edit, rate or score the questions-insights for each milestone.

The curation engine may be configured to receive the ratings/scores from the plurality of curators. The curation engine may then filter the data by comparing their ratings/scores to a predetermined threshold. Data having ratings/scores above the predetermined threshold may be provided by the curation engine to the recommendation engine. The data having ratings/scores above the predetermined threshold may be collectively referred to as community wisdom.

The recommendation engine may be configured to map the community wisdom to the milestones on the user's timeline, so as provide personalized recommendations to the user for each milestone. The recommendation engine may be capable of predicting the user's needs based on the user query, as previously described. In some embodiments, the recommendation engine can predict the user's needs based on: (1) the user's profile, (2) information obtained directly or indirectly from the user, (3) user's action (or inaction) regarding certain matters, and/or (4) user's interaction with other users. The recommendation engine can provide personalized recommendations to the user, by analyzing the milestones and events that other similar users have gone and the insights that those users provided. The recommendation engine can determine similarity based on parameters including the users' age, ethnicity, geographical location, type of SLT and milestones, income, personality, spending habits, etc.

In some embodiments, the recommendation engine can dynamically provide personalized recommendations to the user in real-time. The personalized recommendations may also be provided at a predetermined frequency, e.g., every hour, 12 hours, 24 hours, 2 days, 4 days, etc. Alternatively, the personalized recommendations may be provided on a pseudo-random order. In some instances, the recommendation engine can provide a personalized recommendation each time it receives a user query, or when there are new insights and/or milestones.

In some embodiments, in addition to providing a user with the information that the user seeks and will most likely consume, the recommendation engine can further provide personalized recommendations to influence the user's needs.

When the SLT is cancer, the user's needs and challenges may vary each day. For example, the things that the user needs on the day of chemotherapy will likely be different from the things that the user needs the next day or three days later. The user's journey may also change because the disease may change its course (for example, the user's body may have varying responses to chemotherapy treatment). The user's mood may also change frequently and erratically due to anxiety, pain, depression, etc. Furthermore, the user's journey may be influenced by other personal non-clinical events.

The recommendation engine can be configured to take into account the dynamic nature of the user's journey and various context points. For example, the recommendation engine can parametrize the user's behavior and body response characteristics at different timeframes (e.g., 2 days before chemotherapy, 1 hour after chemotherapy, 2 days after chemotherapy, etc.). For example, the user may share a message with other users to indicate that he is feeling pain at the hospital during the chemotherapy. In some embodiments, the recommendation engine can be configured to: (1) locate which point of the journey that the user is at, (2) extract temporal status from the user's location, social interaction, and mood/thoughts (e.g. the user's feelings at a particular moment), (3) determine the user's potential needs based on the above, and (4) provide personalized recommendations based on those potential needs. Accordingly, in some embodiments, the recommendation engine may be capable of sentiment analysis, so as to more accurately construe and predict the user's needs.

In some embodiments, the recommendation engine can generate one or more graphical user interfaces (GUIs) comprising timelines, milestones, and insights/recommendations. Any number of timelines, milestones and insights/recommendations may be contemplated. The GUIs may be rendered on a display screen on a user device. A GUI is a type of interface that allows users to interact with electronic devices through graphical icons and visual indicators such as secondary notation, in addition to text-based interfaces, typed command labels or text navigation. The actions in a GUI are usually performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be displayed on a user device (e.g., user device 102 of FIG. 1). Examples of such GUIs are illustrated in FIGS. 3 through 24, and FIGS. 26 through 28, as described elsewhere herein.

A computer-implemented method for assisting a plurality of users in navigating one or more life events may be provided in accordance with various embodiments of the invention. The one or more life events include at least one of the following: diagnosis with a terminal illness, death, marriage, divorce, or retirement. The method can be implemented using the event navigation system(s) described elsewhere herein. The method may comprise providing interactive media to a plurality of computing devices associated with the plurality of users. The interactive media may be provided via an event navigation portal that is designed to aid the plurality of users in navigating the one or more life events. The interactive media may comprise a set of visual objects associated with the one or more life events. The set of visual objects may be displayed to the users on graphical displays of the computing devices.

The method may also include receiving input data from the computing devices when the users interact with the set of visual objects in the event navigation portal; and analyzing the input data derived from the users' interaction with the set of visual objects to: (1) determine the life event(s) that each user is currently experiencing, has experienced, or is likely to experience, (2) predict one or more steps relating to the life event(s) for each user, wherein each step further comprises information to aid the user in navigating said step, and (3) map the step(s) relating to the life event(s) for each user on a timeline, wherein the timeline and the step(s) are included in the set of visual objects and displayed to the users on the graphical displays of the computing devices.

It should be noted that the term "life events" as used herein may be referred to interchangeably as significant life transitions (SLTs). Similarly, the term "steps" as used herein may be referred to interchangeably as milestones.

In some embodiments, the input data may comprise questions, answers, comments, and/or insights in the form of text, audio, video, and/or photographs that are (1) provided by the plurality of users and (2) associated with the one or more life events. The input data may also be obtained from a social media or a social networking website visited by the plurality of users. In some embodiments, the input data may be analyzed using a natural language processing (NLP) algorithm, as described elsewhere herein. In some embodiments, the input data may further comprise information indicative of the physical locations of the plurality of users. The physical locations of the users are extracted from the input data, as described elsewhere herein. The information indicative of the physical locations of the users may be dynamically updated in real-time as the users move between different places.

In some embodiments, the users may interact with the set of visual objects on the graphical displays using at least one of the following input devices: a mouse, a keyboard, a touchscreen monitor, a voice recognition software, or a virtual reality and/or augmented reality headset. In some embodiments, the timeline and the step(s) may be configured to be manipulated on the graphical displays by the users. The manipulation of the timeline and the step(s) by the users may comprise at least one of the following: (1) modifying the timeline to display a desired time period, (2) increasing or decreasing a duration of the timeline, (3) modifying the location of each step along the timeline, (4) displaying the information included within each step, (5) modifying the information displayed within each step, (6) overlaying a plurality of timelines for the plurality of users onto a common timeline, or (7) linking different timelines for different life events.

In some embodiments, the method may further comprise: generating a predictive model by applying machine learning to the input data received from the plurality of users. The predictive model may be used to predict the one or more steps relating to the life event(s) for each user. The predictive model may be configured to predict each user's needs at each step along the timeline. The information in each step may be customized for each user depending on the user's predicted needs.

In some embodiments, the predictive model may be configured to extract temporal status of the users based on the users' interactions within the event navigation portal. The temporal status of the users may correspond to mental states or physical states of the users at a given moment in time. The temporal status of the users may be extracted based on thoughts, feelings, opinions, statements, and/or comments made by the users in the interactions within the event navigation portal.

In some embodiments, two or more of the steps relating to the life event(s) may be mapped in chronological order on the timeline for each user. In some cases, two or more of the steps may occur at a same point in time along the timeline for each user. Alternatively, two or more of the steps may occur at different points in time along the timeline for each user. In some embodiments, the step(s) and the information in each step may be updated dynamically on the timeline as the users experience the life event(s).

In some embodiments, the information in each step may comprise insights or comments that are provided by one or more users about the corresponding step. The method may further comprise: filtering one or more user insights from the input data, and matching the one or more user insights to the one or more steps. The matching may be based on at least one of the following: (1) a crowd-sourced rating of each user insight, (2) a credentials rating of a user associated with a user insight, (3) a popularity rating of each user insight, or (4) a popularity rating of a user associated with the corresponding user insight. In some embodiments, the matching may be based on a plurality of predefined topics associated with the life event(s). In some embodiments, the method may further comprise: determining a frequency at which each user insight is matched to the corresponding step, and ranking the matched user insights based on their frequencies.

In some embodiments, the method may further comprise: displaying a plurality of different possible journeys to the users on the graphical displays of the computing devices. The plurality of different possible journeys may be generated through different combinations of the steps on the timeline, as described elsewhere herein. In some embodiments, the plurality of different journeys and steps may be selectable by the users, to allow the users to observe the effects of selecting different journeys and/or steps for the life event(s). The plurality of different journeys and steps may be included in the set of visual objects that are displayed on the graphical displays of the computing devices.

In some embodiments, the plurality of different journeys and steps may be configured to be spatially manipulated by the users on the graphical displays of the computing devices using drag-and-drop functions. In some embodiments, at least some of the journeys and/or steps may be configured to be (1) expanded into a plurality of sub journeys and/or sub-steps, or (2) collapsed into a main journey and/or main step. In some cases, the timeline may further comprise a graphical plot indicative of a significance level of each step on the timeline to each user.

In some embodiments, the users' interactions with the set of visual objects may comprise the users entering alphanumeric text, image data, and/or audio data via one or more of the visual objects on the graphical displays. In some embodiments, the set of visual objects may be provided on the graphical displays in a plurality of different colors, shapes, dimensions, and/or sizes. The timeline and step(s) for different users may be displayed in different visual coding schemes.

According to another aspect of the invention, a system for implementing an event navigation portal that is designed to aid a plurality of users in navigating one or more life events may be provided. The system may comprise: a server in communication with a plurality of computing devices associated with a plurality of users. The server may comprise a memory for storing interactive media and a first set of software instructions, and one or more processors configured to execute the first set of software instructions to provide the interactive media via the event navigation portal to the plurality of computing devices associated with the plurality of users. The interactive media may comprise a set of visual objects associated with the one or more life events. The set of visual objects may be displayed to the users on graphical displays of the computing devices. The processor(s) may also be configured to execute the first set of software instructions to: receive input data from the computing devices when the users interact with the set of visual objects in the event navigation portal; and analyze the input data derived from the users' interaction with the set of visual objects to: (1) determine the life event(s) that each user is currently experiencing, has experienced, or is likely to experience, (2) predict one or more steps relating to the life event(s) for each user, wherein each step further comprises information to aid the user in navigating said step, and (3) map the step(s) relating to the life event(s) for each user on a timeline, wherein the timeline and the step(s) are included in the set of visual objects.

In some embodiments, the plurality of computing devices may comprise a memory for storing a second set of software instructions, and one or more processors configured to execute the second set of software instructions to: receive the interactive media from the server; display the set of visual objects visually on the graphical displays of the computing devices to the users; generate the input data when the users interact with the set of visual objects in the event navigation portal; transmit the input data to the server for analysis of the input data; receive the analyzed input data comprising the timeline and the step(s); and display the timeline and the step(s) on the graphical displays of the computing devices to the users.

In some embodiments, a tangible computer readable medium storing instructions that, when executed by one or more servers, causes the one or more servers to perform a computer-implemented method for assisting a plurality of users in navigating one or more life events may be provided. The method may comprise: providing interactive media to a plurality of computing devices associated with the plurality of users. The interactive media may be provided via an event navigation portal that is designed to aid the plurality of users in navigating the one or more life events. The interactive media may comprise a set of visual objects associated with the one or more life events. The set of visual objects may be displayed to the users on graphical displays of the computing devices. The method may also comprise receiving input data from the computing devices when the users interact with the set of visual objects in the event navigation portal; and analyzing the input data derived from the users' interaction with the set of visual objects to: (1) determine the life event(s) that each user is currently experiencing, has experienced, or is likely to experience, (2) predict one or more steps relating to the life event(s) for each user, wherein each step further comprises information to aid the user in navigating said step, and (3) map the step(s) relating to the life event(s) for each user on a timeline, wherein the timeline and the step(s) are included in the set of visual objects and displayed to the users on the graphical displays of the computing devices.

The event navigation system can generate one or more windows depicting a virtual environment (e.g., an event navigation portal) that is designed to aid users in navigating one or more life events. The interactive media may be provided in the one or more windows. The windows may be graphical user interfaces (GUIs) that are rendered on a display screen of a user device or on an output device. A GUI is a type of interface that allows users to interact with electronic devices through graphical icons and visual indicators such as secondary notation, in addition to text-based interfaces, typed command labels or text navigation. The actions in a GUI may be performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be displayed on the user devices. One or more the embodiments described in the following figures may be implemented in GUIs.

Figure 3:
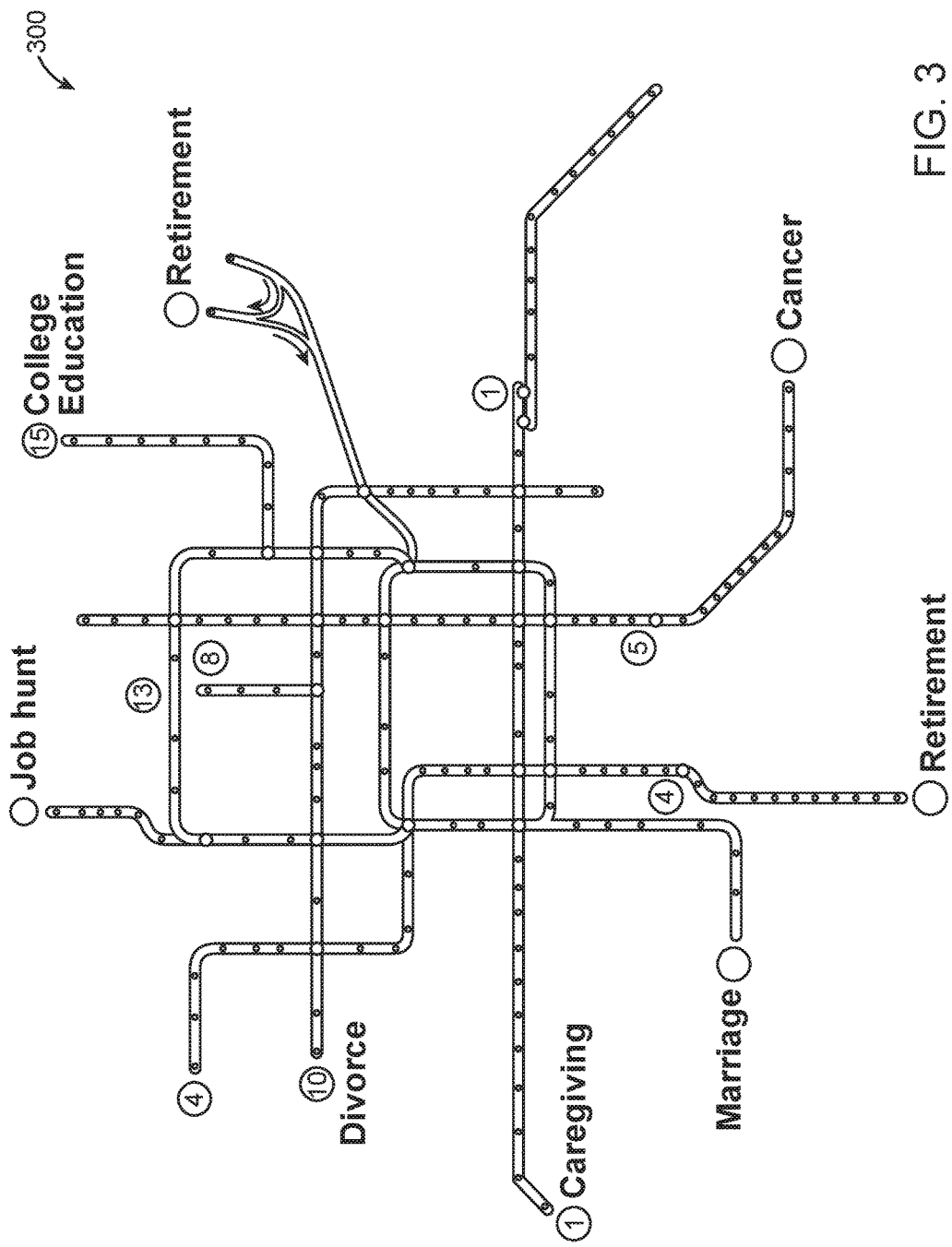
FIG. 3 illustrates an exemplary SLT map, in accordance with some embodiments.

FIG. 3 illustrates an exemplary SLT map 300 in accordance with some embodiments. Map 300 may include a plurality of SLTs such as college education, job hunt, marriage, divorce, retirement, a terminal illness (e.g., cancer), and/or caregiving. Each SLT may be represented by a timeline of a different color. For example, caregiving may be represented by a red timeline, and cancer may be represented by a purple timeline. It is noted that any type of visual scheme comprising different shapes, colors, icons, etc. can be used to illustrate the SLTs. In some cases, the SLT timelines may be interconnected to one another. For example, job hunt may be preceded by college education, and divorce may be preceded by marriage. A user may experience some or all of these SLTs at different stages of their lives. In some instances, more than one SLT may occur during a same stage of the user's life (e.g., terminal illness occurring during retirement).

Figure 4:
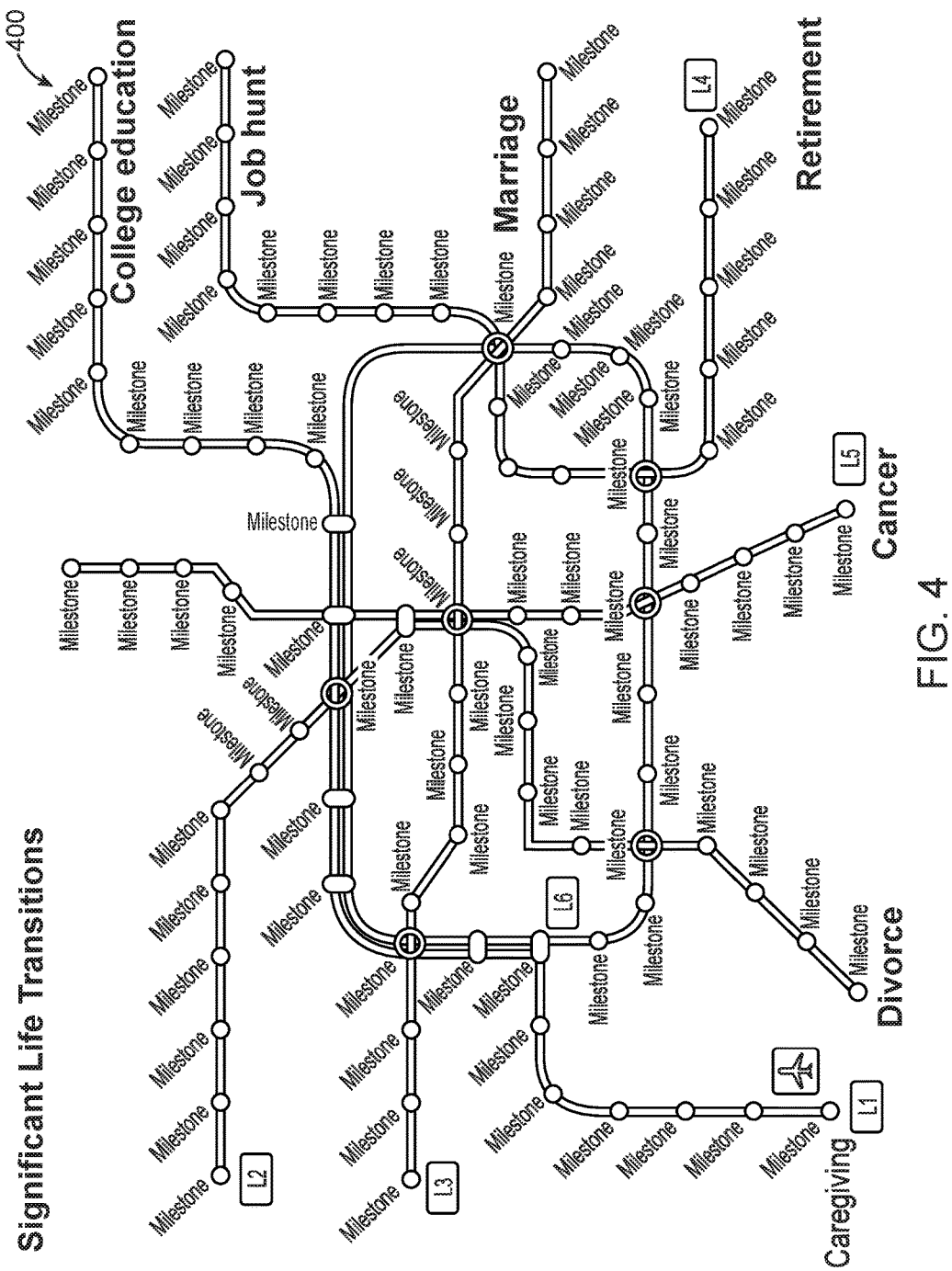
FIG. 4 illustrates an exemplary SLT map, in accordance with some further embodiments.

FIG. 4 illustrates an exemplary SLT map 400 in accordance with some further embodiments. The SLT map 400 of FIG. 4 may be similar to the SLT map 300 of FIG. 3. In the example of FIG. 4, the SLTs may further comprise a plurality of milestones. The milestones may be denoted by a plurality of white circles disposed along the SLT lines.

The SLT maps 300 and 400 may be manipulated by a user in different ways. For example, a user may focus in or out of the map, focus on a particular SLT, scroll to the left/right/ top/bottom of the window to see additional SLTs or timelines, and/or select a particular milestone on a SLT. Accordingly, a user can find out more information about different SLTs, the different milestones within each SLT, and personalized community wisdom for each milestone. In some instances, if the user is currently undergoing a SLT, or will go through a SLT in the near future, the recommendation engine can deliver personalized recommendations to the user based on the user's needs, milestones, and SLT timeline.

Figure 5:
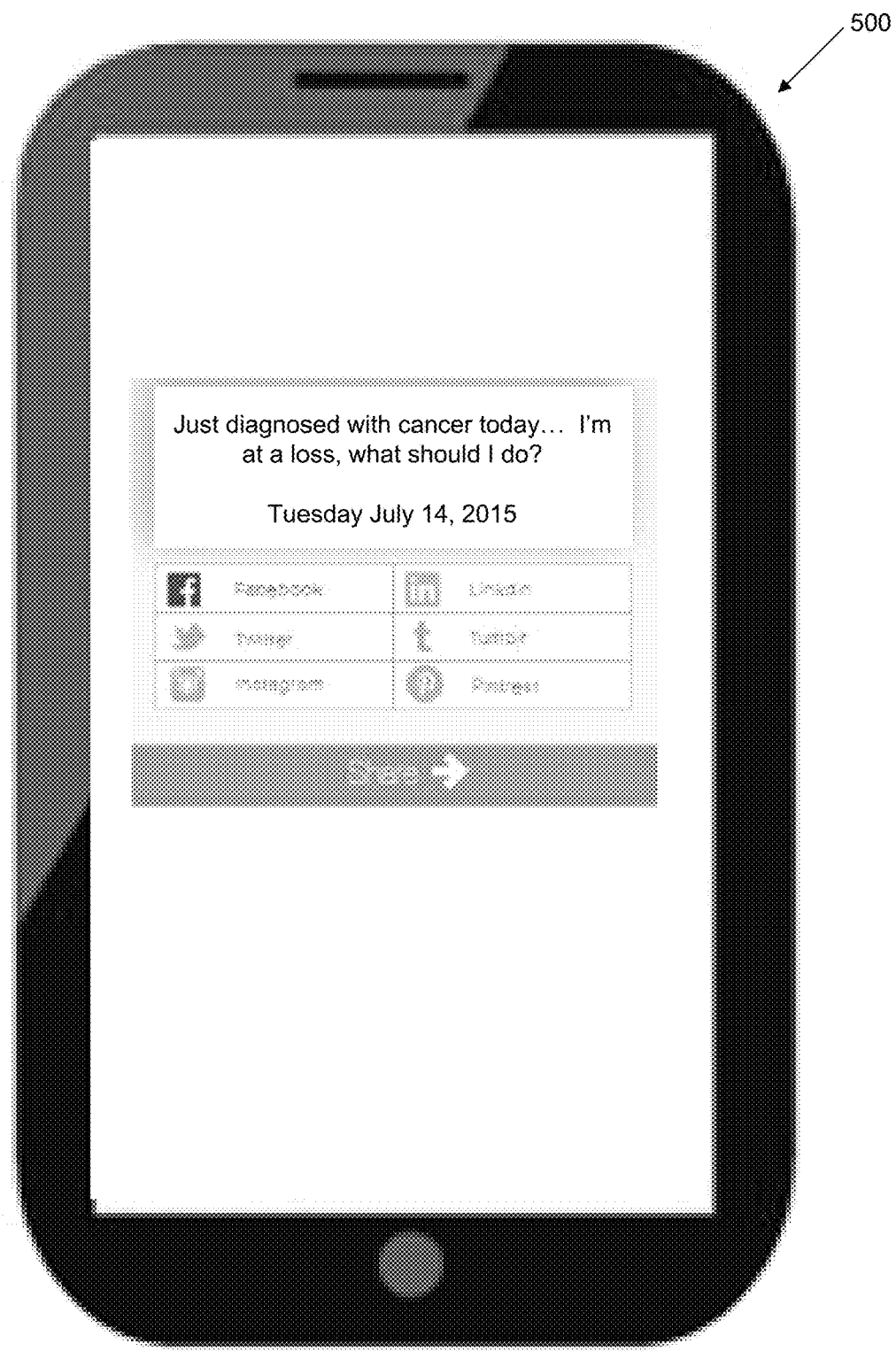
FIG. 5 illustrates an exemplary user query, in accordance with some embodiments.

FIG. 5 illustrates an exemplary user query 500 in accordance with some embodiments. In the example of FIG. 5, the user query may be a text message posted on Tuesday Jul. 14, 2015 containing the following: "Just diagnosed with cancer today . . . . I'm at a lost, what should I do?" A user may input the user query by typing the text message on a user device, and share the message with other users (e.g., his network of contacts in one or more selected social media). Window 500 may include links to social media such as such as Facebook™, Twitter™, Instagram™, LinkedIn™, Tumblr™, or Pinterest™. In some instances, when the user selects the Share button, the text message may be sent from the user device to the matching engine for natural language processing. Based on the contents in the text message, the matching engine may determine that the user is recently diagnosed with cancer, and that she is at a loss as how to handle the SLT.

Figure 6:
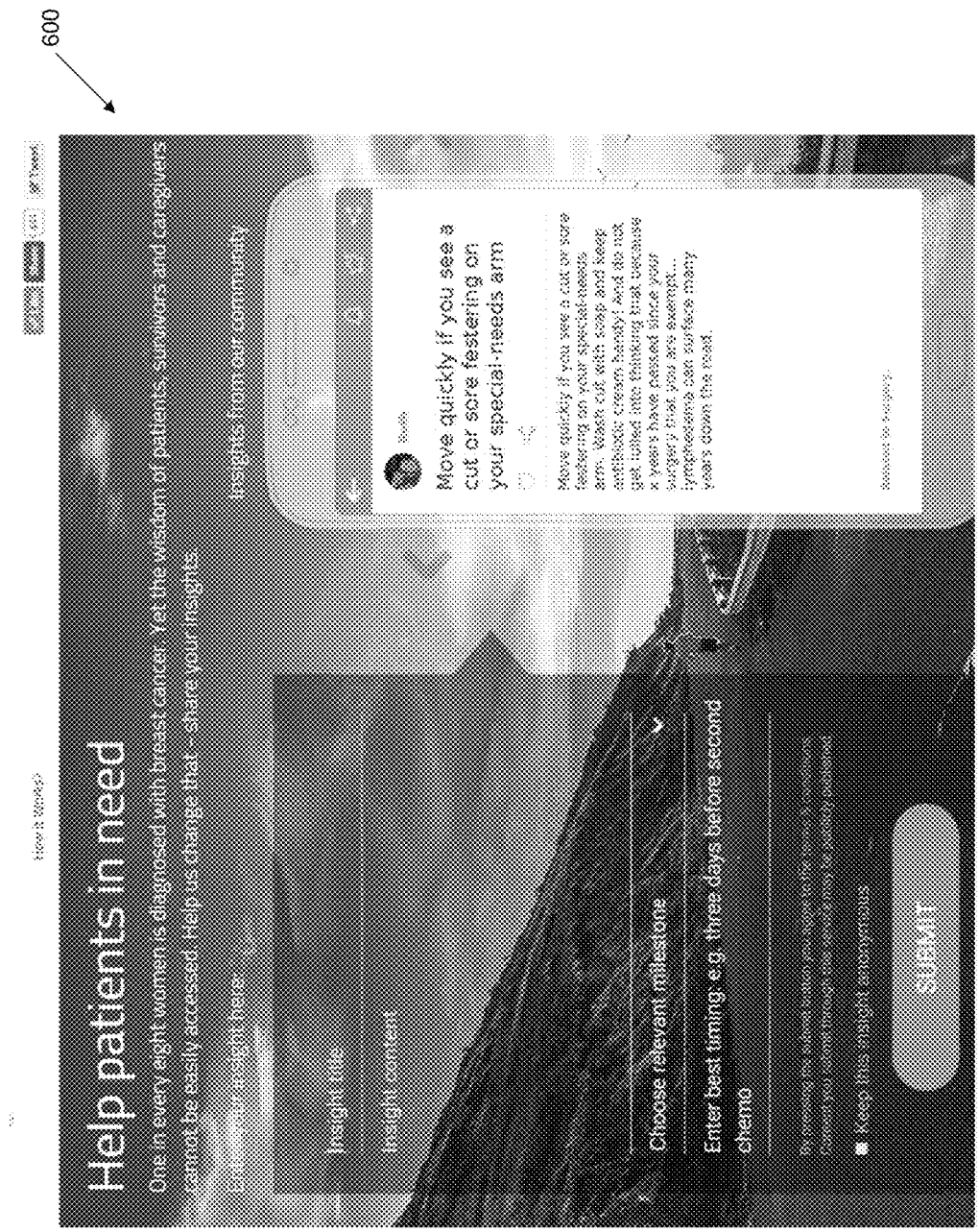
FIG. 6 illustrates an exemplary contributor insight window, in accordance with some embodiments.

After the matching engine has determined the SLT that the user is going through, the matching engine may obtain insights from one or more contributors regarding the SLT (specific milestones within the SLT). FIG. 6 illustrates an exemplary contributor insight window 600 in accordance with some embodiments. In the example of FIG. 6, the contributor insight window 600 may be generated by the matching engine and sent to one or more contributors soliciting for insights, as indicated by the "Help patients in need" title at the top of window 600. In some instances, window 600 may include a message to contributors to request their insights. When the SLT is diagnosis with breast cancer, an example of such message may be: "One in every eight woman is diagnosed with breast cancer. Yet the wisdom of patients, survivors and caregivers cannot be easily accessed. Help us change that—share your insights." Window 600 may include an insight input box, in which a user can provide an insight title, provide insight content, choose a relevant milestone, and submit the insight. In the example of FIG. 6, the contributor may select the 'best timing' (or most appropriate timing) at which the insight applies. In some instances, the 'best timing' may correspond to the relevant milestone. In some instances, the contributor may define a new milestone for an insight if the milestone has yet to be defined. Contributors can also add and/or suggest new milestones that do not have any insights. Contributors can also add/suggest new topics (domains) for milestones. Any type of milestones, insights, topics, and timing may be contemplated. Accordingly, different contributors can share their experiences and insights pertaining to that milestone. In some cases, a contributor may add his insight on a particular topic or insights provided by other contributors (community of contributors). After the contributor has provided her insight and selected the input button, the insight may be matched to the milestone and then sent to the matching engine.

The matching engine may be configured to receive a plurality of insights relating to a topic or milestone. For example, as shown in FIG. 6, the insights provided by the community may be collectively titled ("Move quickly if you see a cut or sore festering on your special-needs arm"), with the following insights content (" . . . Wash cut with soap and keep antibiotic cream handy! . . . ").

Figure 7:
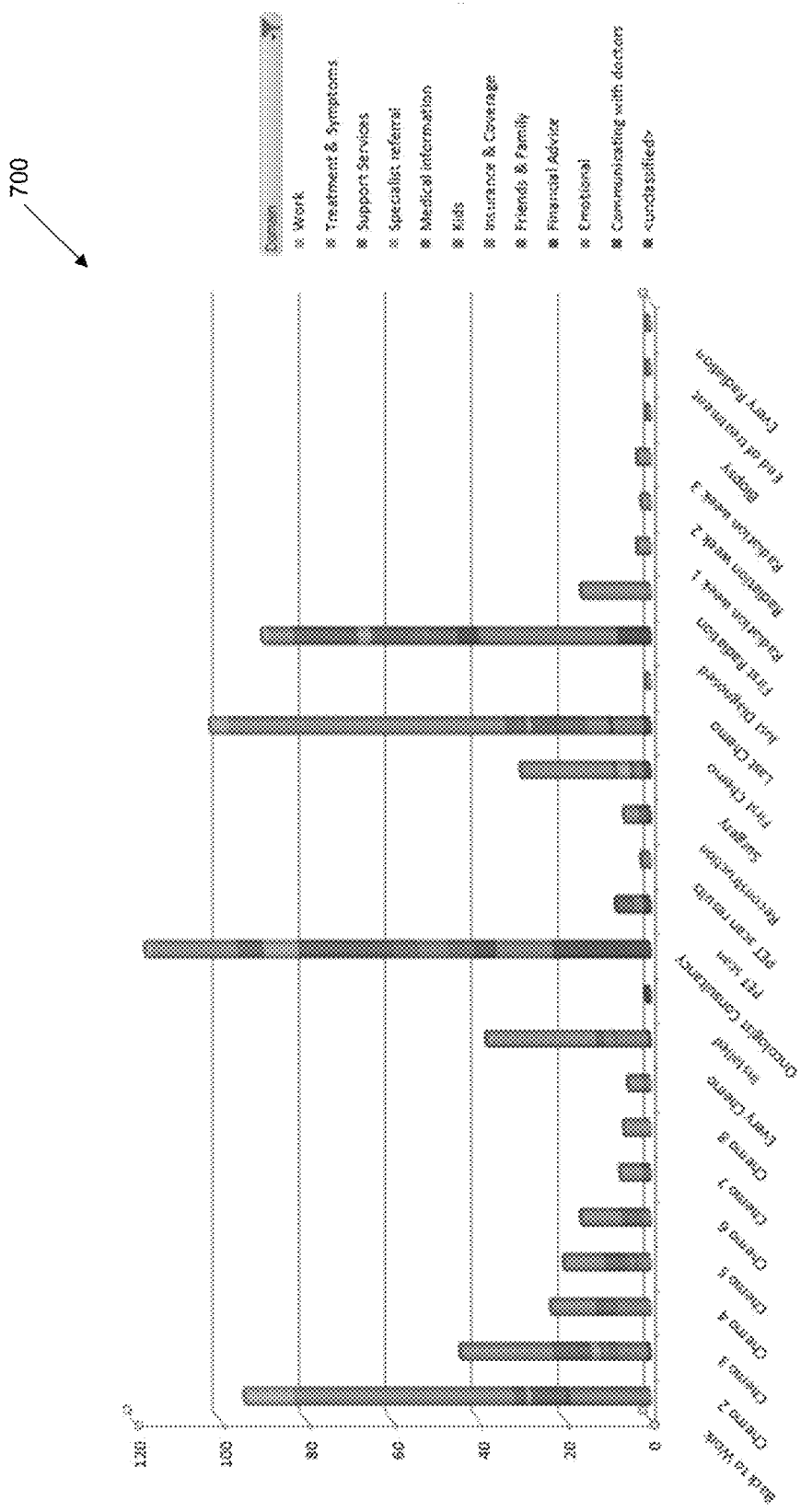
FIG. 7 illustrates an exemplary contributor insights chart, in accordance with some embodiments.

The matching engine may be further configured to filter the insights according to milestones and topics, and to determine the frequencies at which the topics appear within each milestone. As shown in FIG. 7, insights on different topics/domains may appear at different frequencies for individual milestones.

FIG. 7 illustrates an exemplary contributor insights chart 700 in accordance with some embodiments after the matching engine has classified the insights by topics and milestones. As shown in FIG. 7, the milestones "back to work," "oncologist consultancy," "first chemo," and "just diagnosed" have substantially higher number of insights compared to other milestones. Each milestone may include a plurality of insights relating to a variety of topics such as work, treatment and symptoms, support services, specialist referral, medical information, kids, insurance and coverage, friends and family, financial advice, emotional, and communicating with doctors. The topics may be generally classified as clinical or non-clinical. The clinical topics/insights may be related to treatment and symptoms, specialist referral, medical information, and communicating with doctors. Conversely, the non-clinical topics/insights may be related to work, support services, kids, insurance and coverage, friends and family, financial advice, and emotional well-being. As previously mentioned, the insights typically appear at different frequencies within each milestone. For example, at the 'First Chemo' milestone, clinical insights relating to treatment and symptoms may occur with the highest frequency. In contrast, at the 'Just Diagnosed' milestone, non-clinical insights relating to the user's emotional well-being may occur with the highest frequency.

In some instances, there may be insights that cannot be classified into any of the above insights. In those instances, the matching engine may attempt to generate new categories for those insights based on natural language processing, and/or by requesting input from the KOL editorial community (e.g., contributors and SLT alumni). In some instances, there may be SLTs that lack information (e.g., a rare type of disease). Accordingly, the matching engine can attempt to generate milestones and collect insights from contributors relating to those rare SLTs, in order to build the database for those SLTs.

The curation engine may be configured to receive the plurality of insights/milestones from the matching engine, and send the insights/milestones to a curator for editing, curation, scoring and approval. As previously mentioned, a curator may correspond to an alum, or a person who has extensive knowledge and experience with a SLT. For example, a curator may be one who has excellent credentials in the relevant field (e.g., a renowned oncologist if the SLT relates to cancer). In some embodiments, a curator may be one who is highly rated by the community of contributors, for example based on the number of 'likes' and/or positive reviews for the curator. Accordingly, the curator may be someone who is qualified to rate the insights/milestones for accuracy and relevancy. Some curators may be contributors. Likewise, some contributors may be curators. In some embodiments, certain individuals may serve as both contributors and curators.

Figure 8:
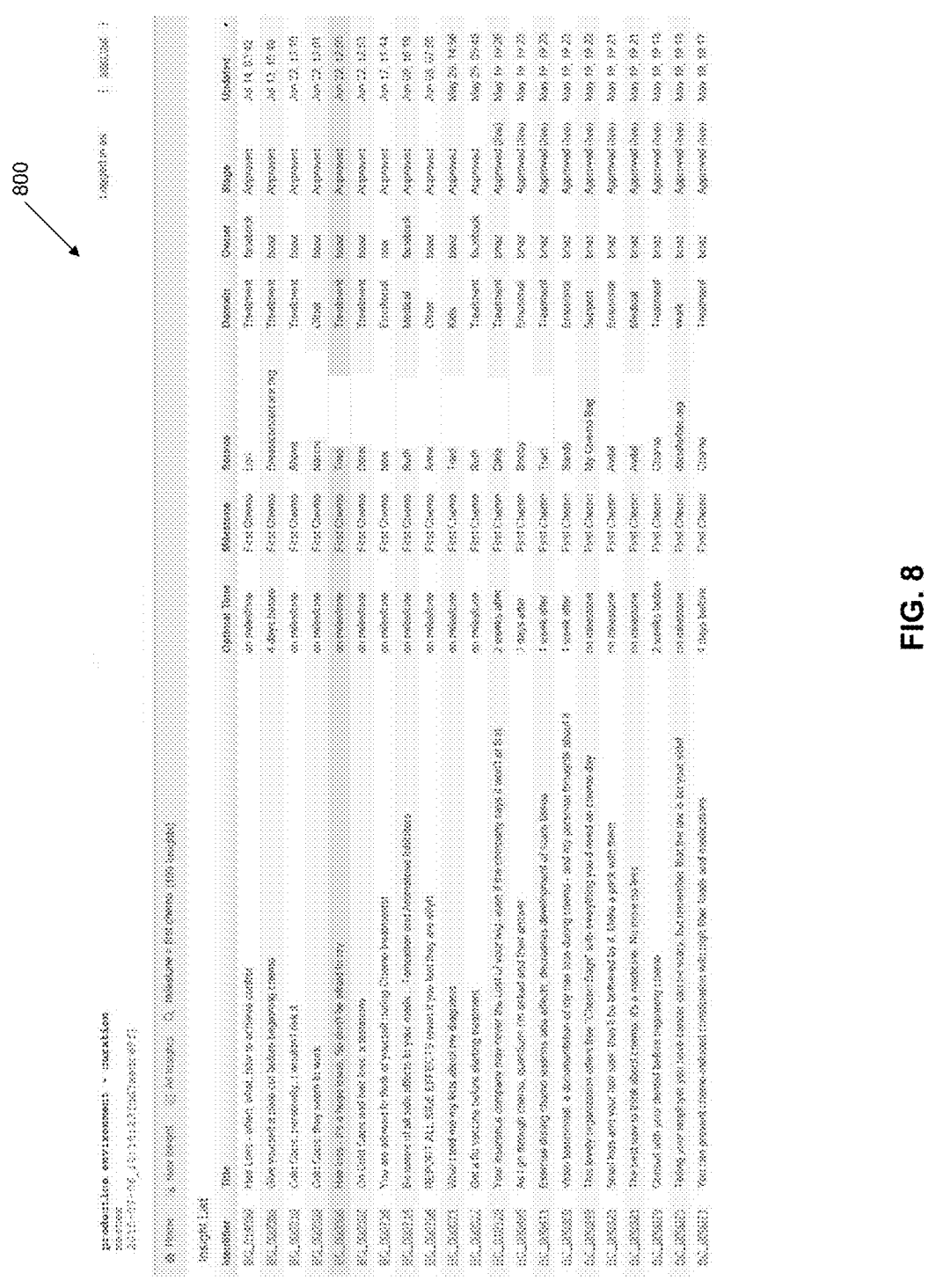

As mentioned above, the contributors may contribute different insights to different questions/events/milestones, and the list of insights may be curated. FIG. 8 illustrates an exemplary insights curation list 800 in accordance with some embodiments. As shown in FIG. 8, a plurality of contributors may have contributed different insights for a terminal illness (breast cancer) SLT. The insights may relate to a wide array of topics, for example, hair loss, chemotherapy, cold caps, medications and their side effects, foods, exercise, questions, and personal experiences (e.g., what a contributor told her children about her diagnosis), etc. Each insight has an identifier, a title, a milestone, an optimal time relative to the milestone, a source, a domain, an owner, a stage, and a date on which the insight is updated. The identifier may be a unique identifier for the insight. The title may contain text that briefly describes the nature of the insight. The milestone may be the relevant milestone (e.g., 'first chemo') to which the insight applies. The optimal time may refer to a recommended timeframe at which the insight applies (e.g., 4 days before milestone, 2 weeks before milestone, etc.). The source may indicate the name of the insight contributor. The domain may refer to the topic to which the insight relates (e.g., treatment, emotional well-being, etc.). The owner may refer to the curator who is rating the insight. The stage may indicate whether the insight has been approved by the curator. The updated column contains the dates on which the insights were updated or approved by the curator. In one example, when a curator selects the insight titled "Hair loss—It's a huge issue. So don't be afraid to cry", window 900 of FIG. 9 may be generated.

FIG. 9 illustrates an exemplary curation window 900 in accordance with some embodiments. Referring to FIG. 9, the insight may relate to hair loss, and may be submitted by a contributor named Lori. The insight may recommend starting a hair loss treatment 3 days before a milestone and ending 1 week after the milestone. The contributor may give a priority level of 1 to the insight. In some cases, a priority level of 1 may indicate that the insight be given high priority. A curator, e.g. a KOL or an editor, may decide whether to approve the insight. In the example of FIG. 9, a curator having a user identity 'boaz' may decide whether to approve the insight. In some instances, the curator may be able to start a private conversation with the contributor regarding the insight, for example, to verify certain aspects and/or to confirm the accuracy of the insight.

In some instances, the curator may rate or assign a score to the contributor's insight. The score may be indicative of a quality of the insight. For example, if the curator agrees with and thinks the insight is highly accurate and relevant for a patient at that particular milestone, the curator may then assign a high score to the insight. Conversely, if the curator thinks there are pieces of information missing from the insight or believes the insight does not adequately address that particular topic/milestone, the curator may then assign a low score to the insight. Therefore, a group of curators may serve as editors of the community to verify the accuracy and relevancy of the insights provided by the contributors. Using the above-described curation process, knowledge from the contributors (in the form of insights) may be filtered into community wisdom by the curators.

The community wisdom may be subsequently personalized for the user depending on the user's needs, the milestone that the user is presently at, and the milestone(s) that the user may face in the future. The community wisdom may be provided as message feeds (e.g., cards containing insights) to the user in a time-sensitive, location-dependent, and content appropriate manner. Feeds may contain visual pieces of relevant content/information for a particular SLT or milestone.

The recommendation engine may be configured to display the milestones and insights on a timeline in a chronological order. In some instances, the recommendation engine may be further configured to display where a plurality of users are located on the timeline. FIG. 10 illustrates an exemplary timeline window 1000 in accordance with some embodiments. Window 1000 may be indicative of a timeline of a SLT, whereby a plurality of different users, feeds, and milestones are provided along the timeline. In other words, window 1000 may represent a map of users and milestones along the timeline. In some instances, window 1000 may be generated by selecting one or more the SLTs (or milestones) depicted in FIG. 3 or 4.

Referring to FIG. 10, a timeline 1010 is depicted. The timeline may be associated with a SLT. The chronology order of the timeline may extend from left to right. A plurality of users 1012a, 1012b, and 1012c, a plurality of milestones (e.g., Chemo 1 and Chemo 2), and a plurality of insights 1014a and 1014b may be depicted at different points along the timeline. The insights may correspond to message feeds (feeds) posted by different users. Users can tag, bookmark, forward, comment, delete, or 'like' a feed. As shown in FIG. 10, user 1012*a* has yet to go through milestone Chemo 1, user 1012*b* has already gone through milestone Chemo 1 but has yet to go through milestone Chemo 2, and user 1012*c* has already gone through both milestones Chemo 1 and Chemo 2. Thus, user 1012*c* is furthest along the SLT journey (possibly the most experienced), whereas user 1012*a* may have just embarked on the SLT journey (possibly the least experienced). Insight 1014*a* may contain recommendations and advice on what a user should do before the first milestone Chemo 1. Insight 1014*b* may contain recommendations and advice on what a user should do after the first milestone Chemo 1, and/or before the second milestone Chemo 2. In the example of FIG. 10, insight 1014*a* may contain insights contributed by users 1012*b* and/or 1012*c*, and insight 1014*b* may contain insights contributed by user 1012*c*. User 1012*a* may initially use insight 1014*a* to prepare for milestone Chemo 1, and later use insight 1014*b* to prepare for milestone Chemo 2. Likewise, user 1012*b* may use insight 1014*b* to prepare for milestone Chemo 2. Users 1012*a*, 1012*b*, and 1012*c* can anticipate what the milestones on the SLT journey are, by looking at the timeline and comparing their present positions relative to the milestones.

Figure 11:
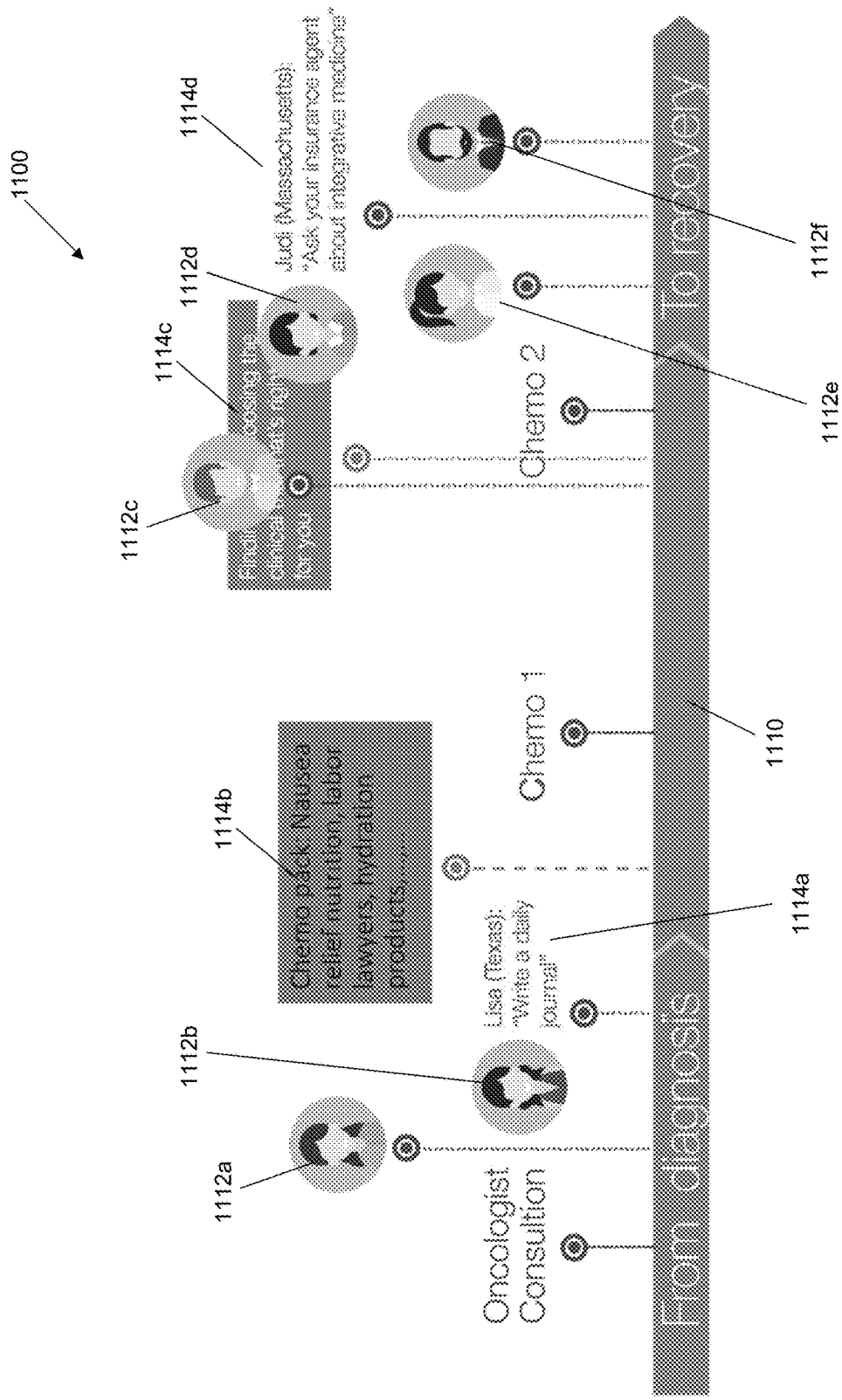
FIG. 11 illustrates another exemplary timeline window, in accordance with some embodiments.

FIG. 11 illustrates another exemplary timeline window 1100 in accordance with some embodiments. Window 1100 may also be indicative of a timeline of a SLT, whereby a plurality of different users, feeds, and milestones are provided along the timeline. In other words, window 1100 may represent a map of users and milestones along the timeline. In some instances, window 1100 may be generated by selecting one or more the SLTs (or milestones) depicted in FIG. 3 or 4.

Referring to FIG. 11, a timeline 1110 is depicted. The chronology of the timeline may extend from left (from diagnosis) to the right (to recovery). A plurality of users 1112*a*, 1112*b*, 1112*c*, 1112*d*, 1112*e*, and 1112*f*, a plurality of milestones (e.g., Oncologist consultation, Chemo 1, and Chemo 2), and a plurality of insights 1114*a*, 1114*b*, 1114*c*, and 1114*d* may be depicted at different points along the timeline. The insights may correspond to message feeds (feeds) posted by different users. Users can tag, bookmark, forward, comment, delete, or 'like' a feed. As shown in FIG. 11, all users 1112 have already gone through the milestone Oncologist consultation. Users 1112*a* and 1112*b* have yet to go through milestone Chemo 1, user 1112*c* has already gone through milestone Chemo 1 but has yet to go through milestone Chemo 2, and users 1112*d*, 1112*e*, and 1112*f* have already gone through both milestones Chemo 1 and Chemo 2. As shown in FIG. 11, user 1112*f* is furthest along the SLT journey (possibly the most experienced), whereas user 1112*a* may have just embarked on the SLT journey (possibly the least experienced). Insights 11114*a* and 1114*b* may contain recommendations and advice on what a user should do before the first milestone Chemo 1. Insight 1114*a* may be a non-clinical insight ("Write a daily journal") provided by user 1112*b* (e.g., Lisa from Texas), and may aid in improving a user's emotional well-being. Insight 1114*b* may be directed to various things (e.g., chemotherapy, nausea relief nutrition, labor lawyers, hydration products, etc.) that a user should keep in mind at that point on the timeline. Insight 1114*c* may be directed to helping a user to find and choose a clinical trial that is optimal for the user. Insight 1114*d* may be provided by user 1112*d* (e.g., Judi from Massachusetts), and may include advice to users to ask their insurance agent whether their insurance covers integrative medicine. Insight 1114*b* may contain insights contributed by users 1112*c*, 1112*d*, 1112*e*, and/or 1112*f*. Insight 1114*c* may contain insights contributed by users 1112*d*, 1112*e*, and/or 1112*f*. Insight 1114*b* may contain recommendations and advice on what a user should do before milestone Chemo 1, and insight 1114*b* may contain recommendations and advice on what a user should do before milestone Chemo 2. Accordingly, users 1112*a*, 1112*b*, 1112*c*, 1112*d*, 1112*e*, and 1112*f* can anticipate what are the milestones on the SLT journey, by looking at the timeline and comparing their present positions relative to the milestones. The users can also connect with another to inquire about each other's experiences and for community support. For example, user 1112*a* can select the icon associated with user 1112*f* in window 1100 to connect with him to learn more about his experience going through the different milestones. Similarly, user 1112*e* can select the icon associated with user 1112*b* in window 1100 to connect and share her experience going through the different milestones. Accordingly, a user can leverage the collective wisdom of the community through exemplary window 1100.

In some embodiments, the exemplary system may generate a crowd-sourced map of the plurality of users, whereby the map may include different milestones and the probability/likelihood that a particular user is going to experience a milestone. For example, the system may calculate that users A and B are more likely to go through milestone X next, whereas users C and D are more likely to go through milestone Y next, based on the characteristics of each user and where each user is located along the timeline/journey. X and Y may be different milestones, with Y occurring at a later point in time than X.

Figure 12:
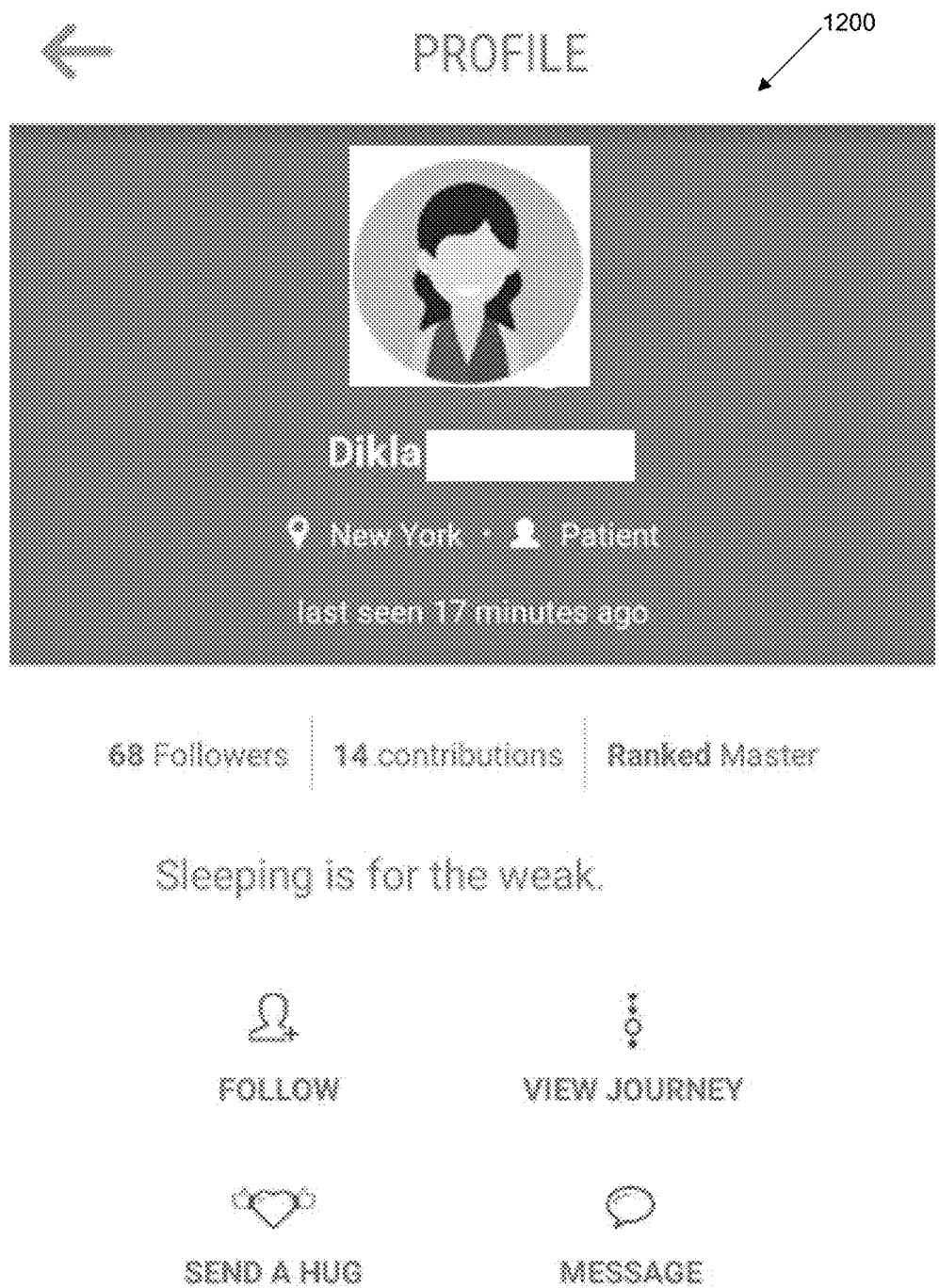
FIG. 12 illustrates an exemplary user profile window, in accordance with some embodiments.

FIG. 12 illustrates an exemplary user profile window 1200 in accordance with some embodiments. Referring to FIG. 12, window 1200 may be associated with a user named Dikla. The user may be a cancer patient living in New York. The user may have any number of followers (e.g. other users following her posts and SLT journey). In some embodiments, the user may also be a contributor. In the example of FIG. 12, the user Dikla may have 68 followers and made 14 insight contributions. The user may be awarded a rank based on her number of followers and/or number of insight contributions. In the example of FIG. 12, the user may be awarded a rank of Master. The user may have posted a motto on her profile window (e.g. "Sleeping is for the weak"). Window 1200 may also include active buttons that other users can select to: (1) follow the user, (2) view the user's SLT journey, (3) send a virtual hug to the user, and/or (4) send a message to the user.

Figure 13:
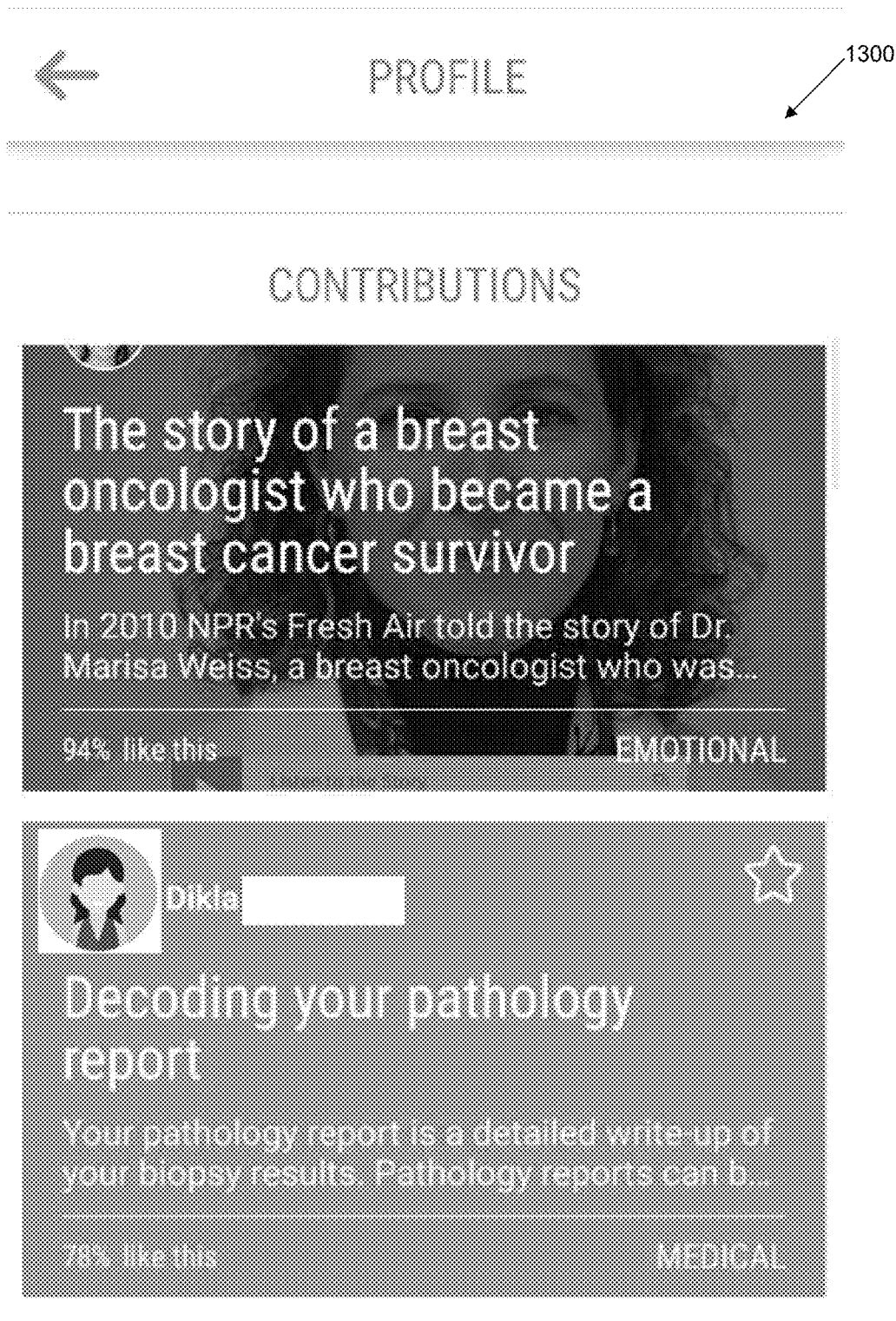
FIG. 13 illustrates an exemplary user profile contributions window, in accordance with some embodiments.

FIG. 13 illustrates an exemplary user profile contributions window 1300 in accordance with some embodiments. Referring to FIG. 13, window 1300 may contain links to insights that are contributed by user Dikla of FIG. 12. The insights may include an emotional insight titled "The story of a breast oncologist who became a breast cancer survivor" and a medical insight titled "Decoding your pathology report." A few lines from each insight may be displayed to generate other users' interest. As shown in FIG. 13, 94% of users who read the emotional insight liked it (i.e., gave the emotional insight a like rating), whereas 78% of users who read the medical insight liked it (i.e., gave the medical insight a like rating). A user may browse through the insights by scrolling up/down window 1300, and select insights that are of interest to her. When a user selects an insight, the full text of the insight may be displayed.

Figure 14:
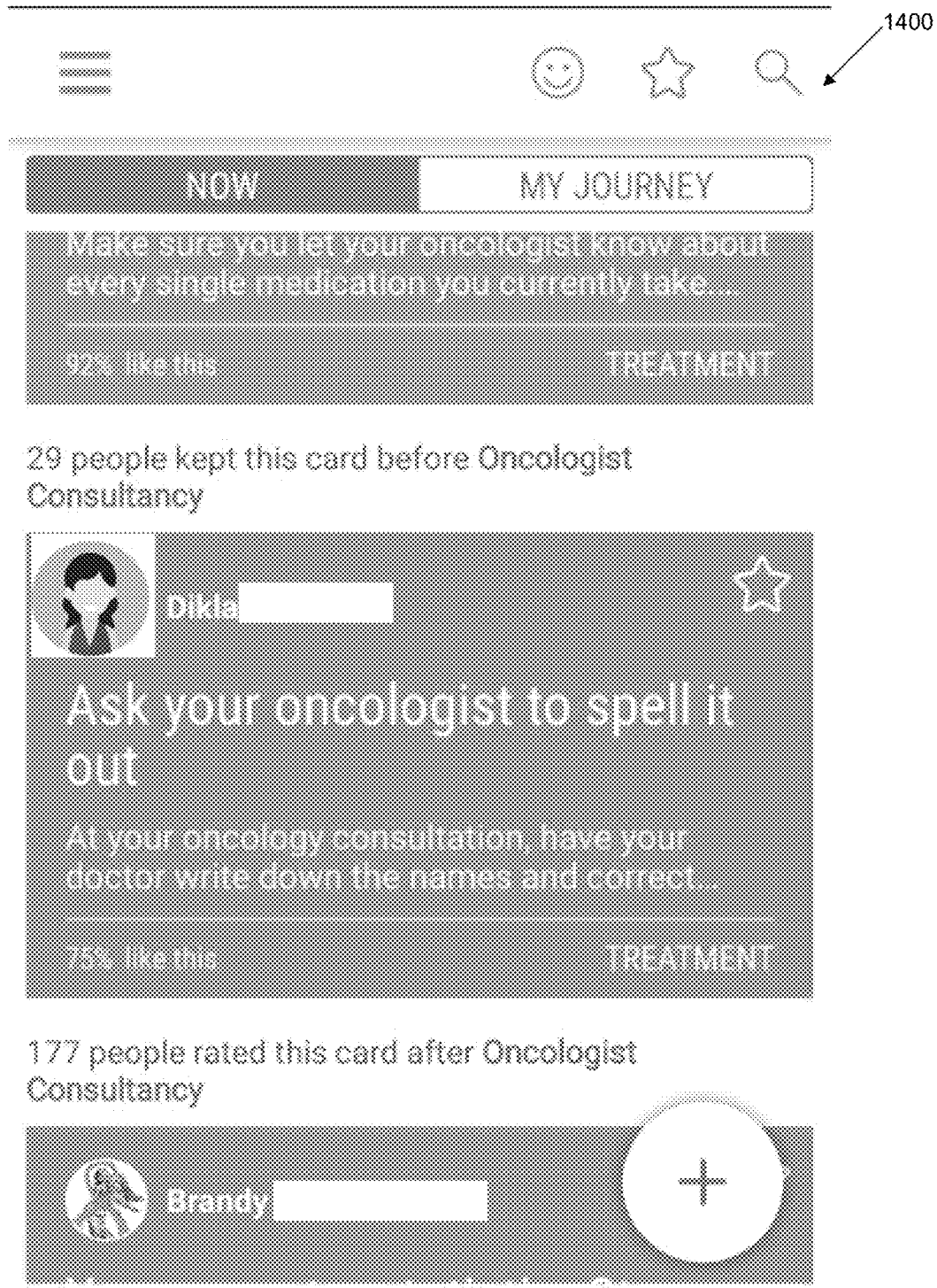
FIG. 14 illustrates an exemplary insights window, in accordance with some embodiments.

FIG. 14 illustrates an exemplary insights window 1400 in accordance with some embodiments. Referring to FIG. 14, window 1400 may include a list of insights for a user at the present milestone. Each insight may be provided as a card (e.g., a reminder card to the user). The cards may constitute feeds. The system can provide the relevant/appropriate feeds to a user based on which milestone the user is currently located (i.e., which part of the SLT journey the user is currently at). As shown in FIG. 14, the Now button is highlighted, which indicates that the cards/insights apply to the present milestone or timeframe. The cards may include a first card ("Make sure you let your oncologist know about every single medication you currently take . . . ") and a second card ("At your oncologist consultation, have your doctor write down the names and correct . . . "). The second card may contain an insight contributed by user Dikla. Although both the first and second cards relate to treatment, it is noted that the cards can also relate to different topics (e.g., emotional, family, work, etc.) in other embodiments. In the example of FIG. 14, 92% of users who read the first card liked it (i.e., gave the first card a like rating), whereas 75% of users who read the second card liked it (i.e., gave the second card a like rating). In addition, 29 people kept the first card before their oncologist consultancy milestone, and 177 people rated the second card after their oncologist consultancy milestone.

Figure 15:
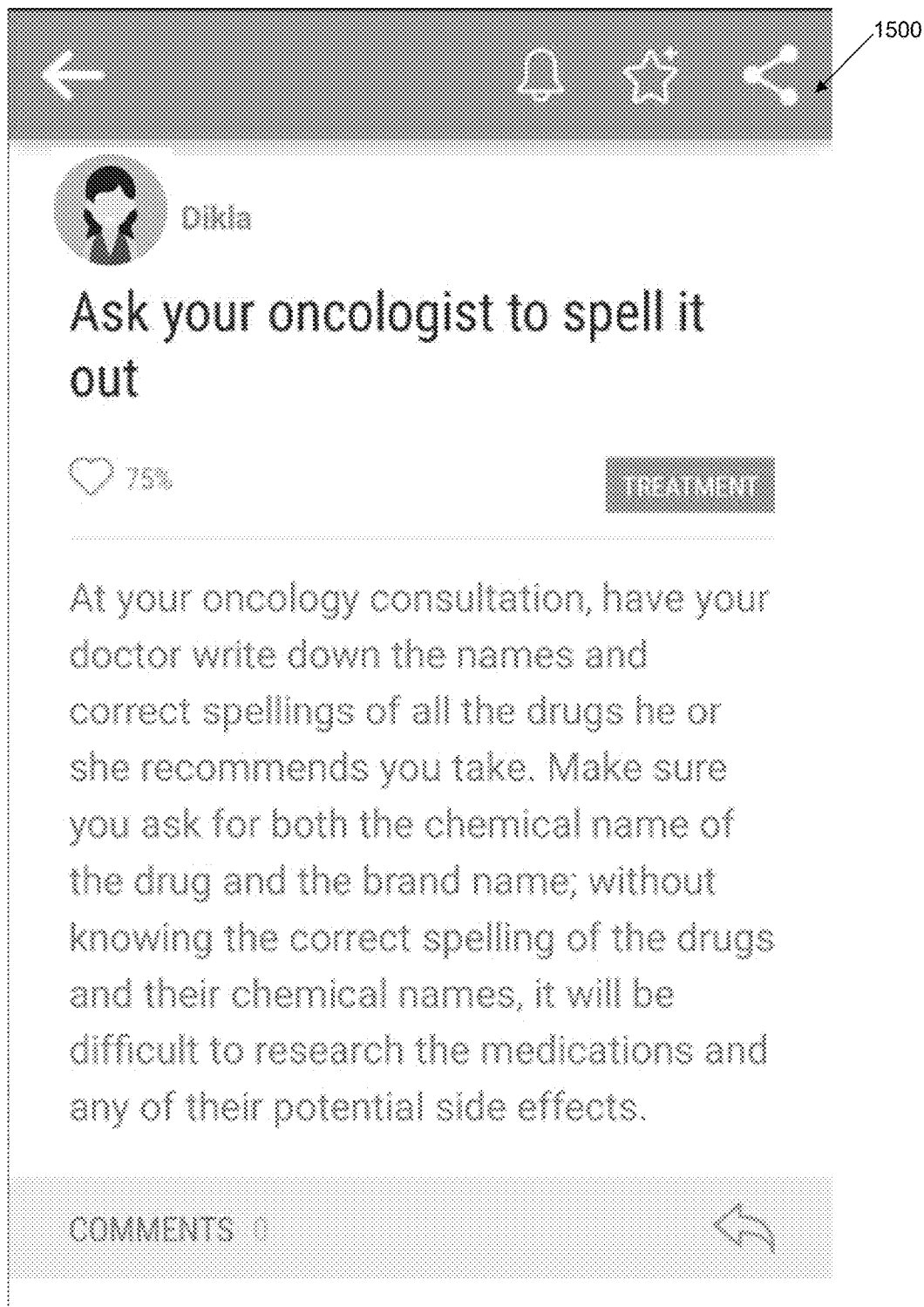
FIG. 15 illustrates an exemplary insight, in accordance with some embodiments.

When a user selects the second card titled "Ask your oncologist to spell it out", the full text of the second card may be displayed, as shown by window 1500 of FIG. 15. The second card reminds the user to ask the doctor to write down the names and spellings of the prescribed drugs during the oncology consultation, so that the user can research the medications and any potential side effects of the medications.

Figure 16:
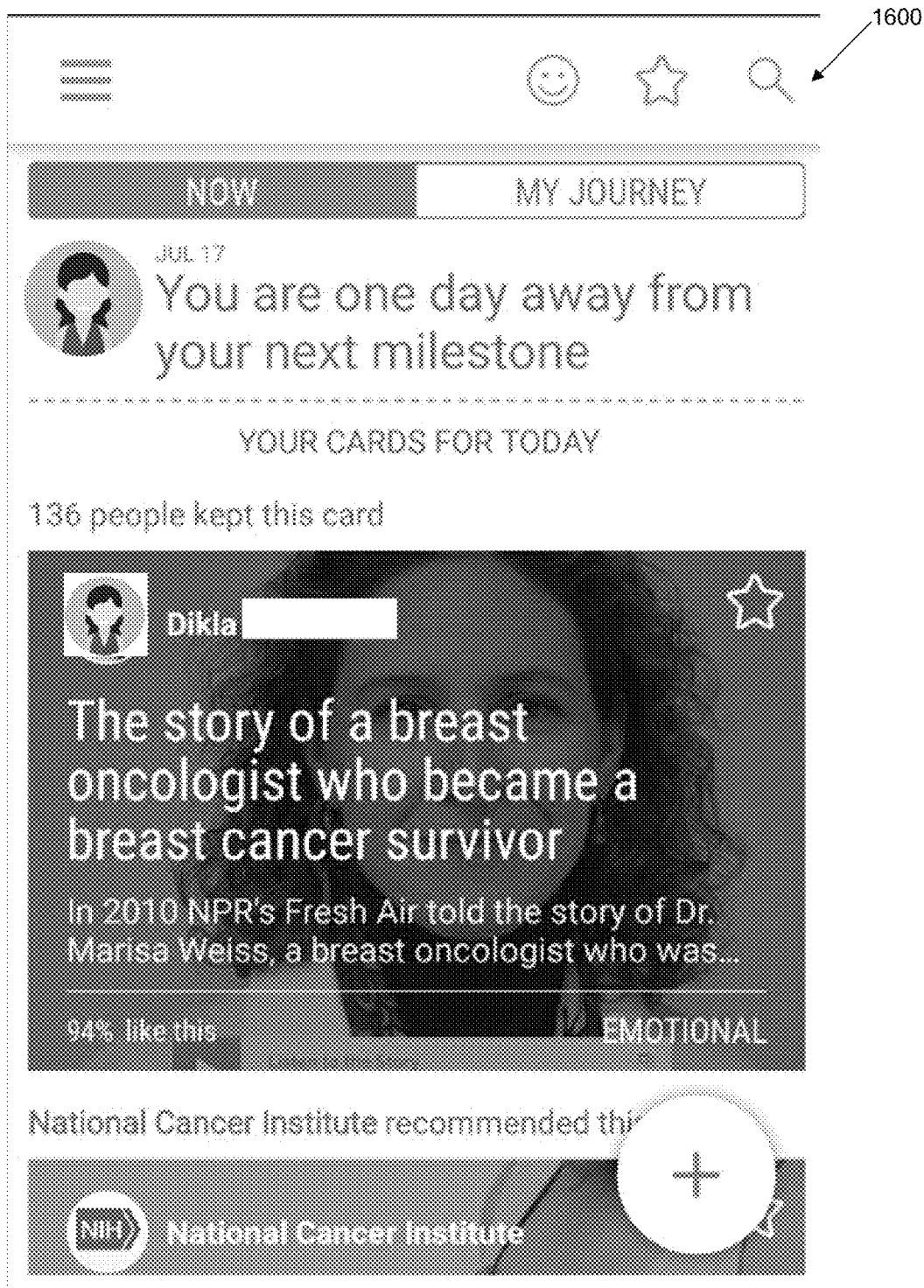
FIG. 16 illustrates another exemplary insights window, in accordance with some embodiments.

FIG. 16 illustrates another exemplary insights window 1600 in accordance with some embodiments. Referring to FIG. 16, window 1600 may include a list of insights for a user on that day (today). Each insight may be provided as a card. As shown in FIG. 16, the Now button is highlighted, which indicates that the cards/insights apply to the present milestone or timeframe. The cards may include a first card ("The story of a breast oncologist who became a breast cancer survivor") and a second card containing an insight contributed by the National Cancer Institute. As shown in FIG. 16, 94% of users who read the first card liked it (i.e., gave the first card a like rating), and 136 users (people) may have kept the first card by bookmarking it. Window 1600 may further include the current date (July 17) and a reminder to the user that her next milestone is one day away. Thus, window 1600 can be used to remind the user of her next milestone, so that she may take the necessary steps to prepare for that milestone.

Figure 17:
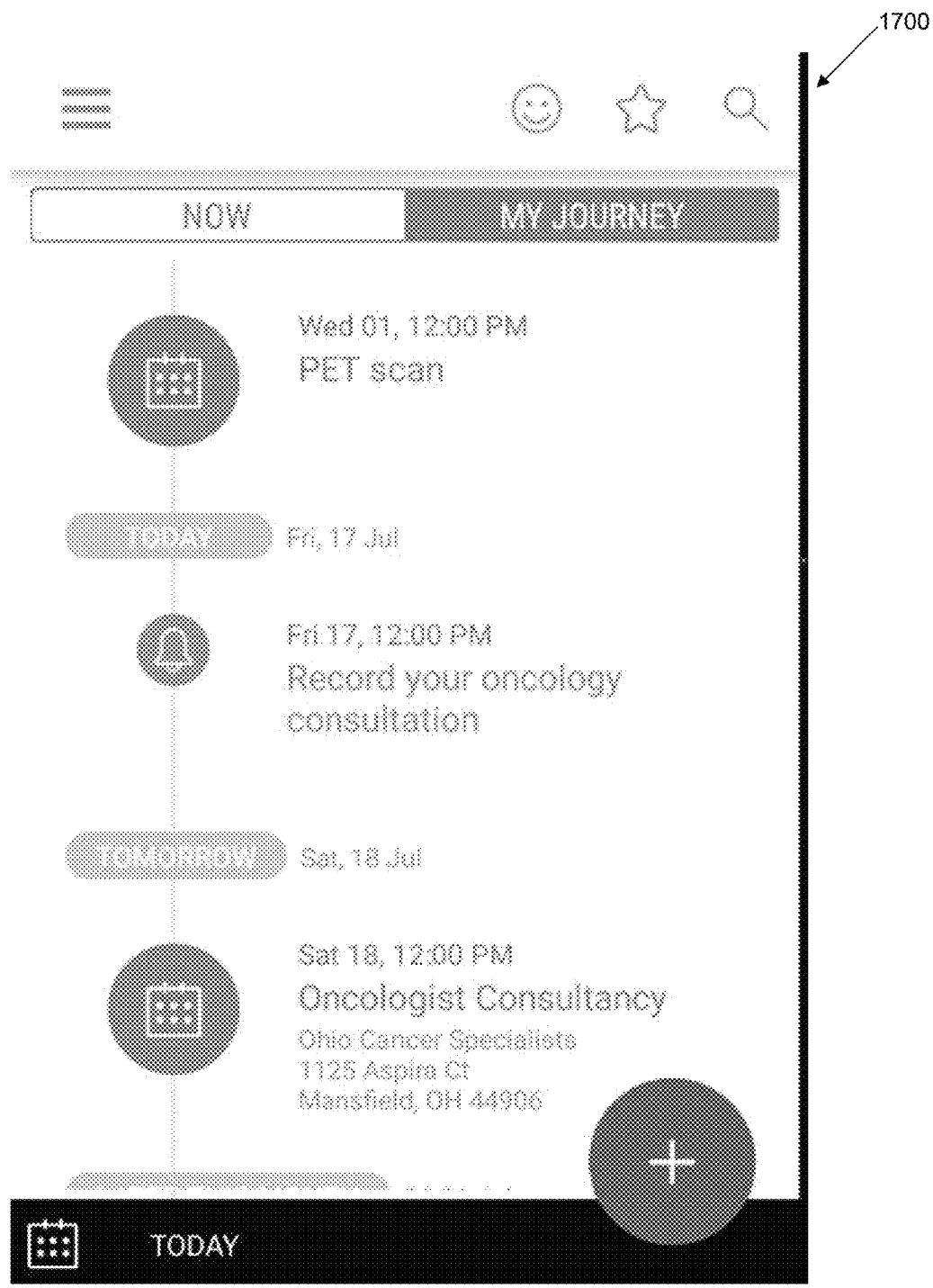
FIG. 17 illustrates an exemplary timeline window, in accordance with some embodiments.

In the embodiments of FIGS. 14 and 16, the Now button is highlighted, which indicates that the cards/insights apply to the present milestone or timeframe. When a user selects the My Journey button, window 1700 of FIG. 17 may be generated. Window 1700 may include a timeline of the user's SLT journey, and milestones/insights at different points on the timeline. The system can anticipate/predict the user's milestones and timeline based on input from the user, and by comparing the user to other similar users who have gone through similar milestones. Window 1700 may be a personalized timeline for the user's journey. As shown in FIG. 17, the timeline may include the previous milestone (PET scan) occurring on Wednesday July 1, the current insight/milestone (Record your oncology consultation) for today Friday July 17, and the next milestone (Oncologist consultancy) taking place tomorrow Saturday July 18. A user may scroll up/down window 1700 to learn about the different milestones/insights along her SLT journey. Accordingly, window 1700 may serve as a timeline calendar of events/milestones/insights/reminders for the user's SLT journey.

In some embodiments, a user can view his/her own personalized SLT journeys (e.g., as shown in FIG. 17), as well as other other users' SLT journeys, by selecting the corresponding user icons illustrated in, for example, FIGS. 10, 11, and 23. Accordingly, a user can compare his/her own SLT journey with others' SLT journeys, so as to anticipate milestones and navigate his/her own SLT journey.

Figure 18:
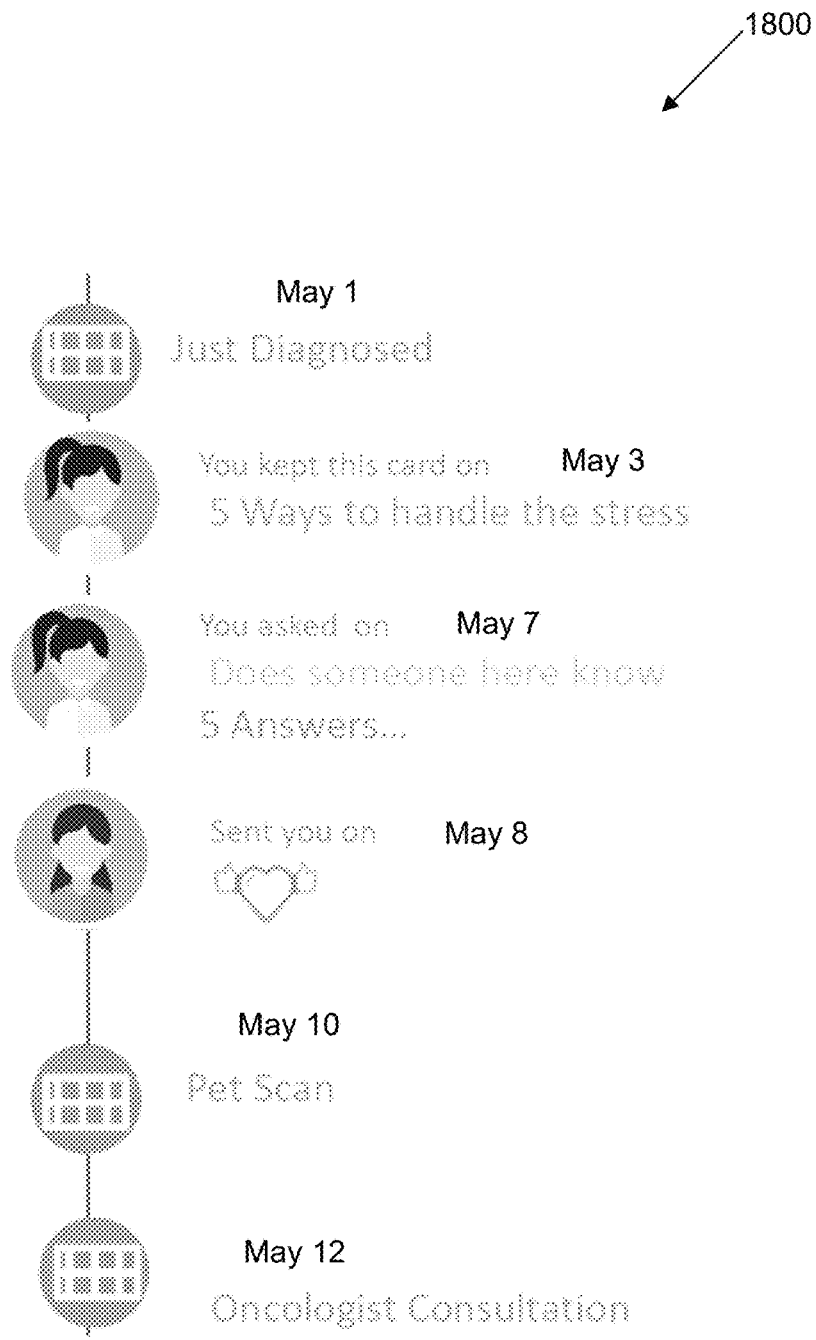
FIG. 18 illustrates another exemplary timeline window, in accordance with some embodiments.

FIG. 18 illustrates another exemplary timeline window 1800 in accordance with some embodiments. Window 1800 includes a timeline of milestones and insights for a user going through a SLT. In the example of FIG. 18, the user may be diagnosed with cancer on May 1. On May 3, the user read and kept a card containing an insight titled "5 ways to handle the stress." On May 7, the user posted a question asking "Does someone here know about . . . ?" and received 5 answers/insights from other users/contributors. On May 8, the user received a virtual hug (see, e.g., FIG. 12) from another user. The user's next milestone is a pet scan on May 10, and the following milestone is an oncologist consultation on May 12.

In some instances, the user may not have any milestone defined beyond the oncologist consultancy milestone on May 12. In those instances, when the user tries to scroll down the window below the oncologist consultancy milestone, window 1900 of FIG. 19 may be generated. Window 1900 illustrates other milestones that the user may probably face. In some embodiments, the other milestones may be depicted as floating in space. The other milestones may include radiation, chemo, surgery, hormone therapy, reconstruction, telling the user's family, genetic tests, recovery, telling the user's employer, end of treatment, back to work, and/or periodic checkup. The other milestones may include clinical milestones and non-clinical milestones. A circular ring may denote an expandable clinical milestone, a square ring may denote an expandable non-clinical milestone, and a circle may denote a single clinical milestone. Each milestone may include a first indicator and a second indicator. The first indicator may indicate the number of people who have gone through or are going through the corresponding milestone. The second indicator may indicate the number of insights for the corresponding milestone.

Figure 19:
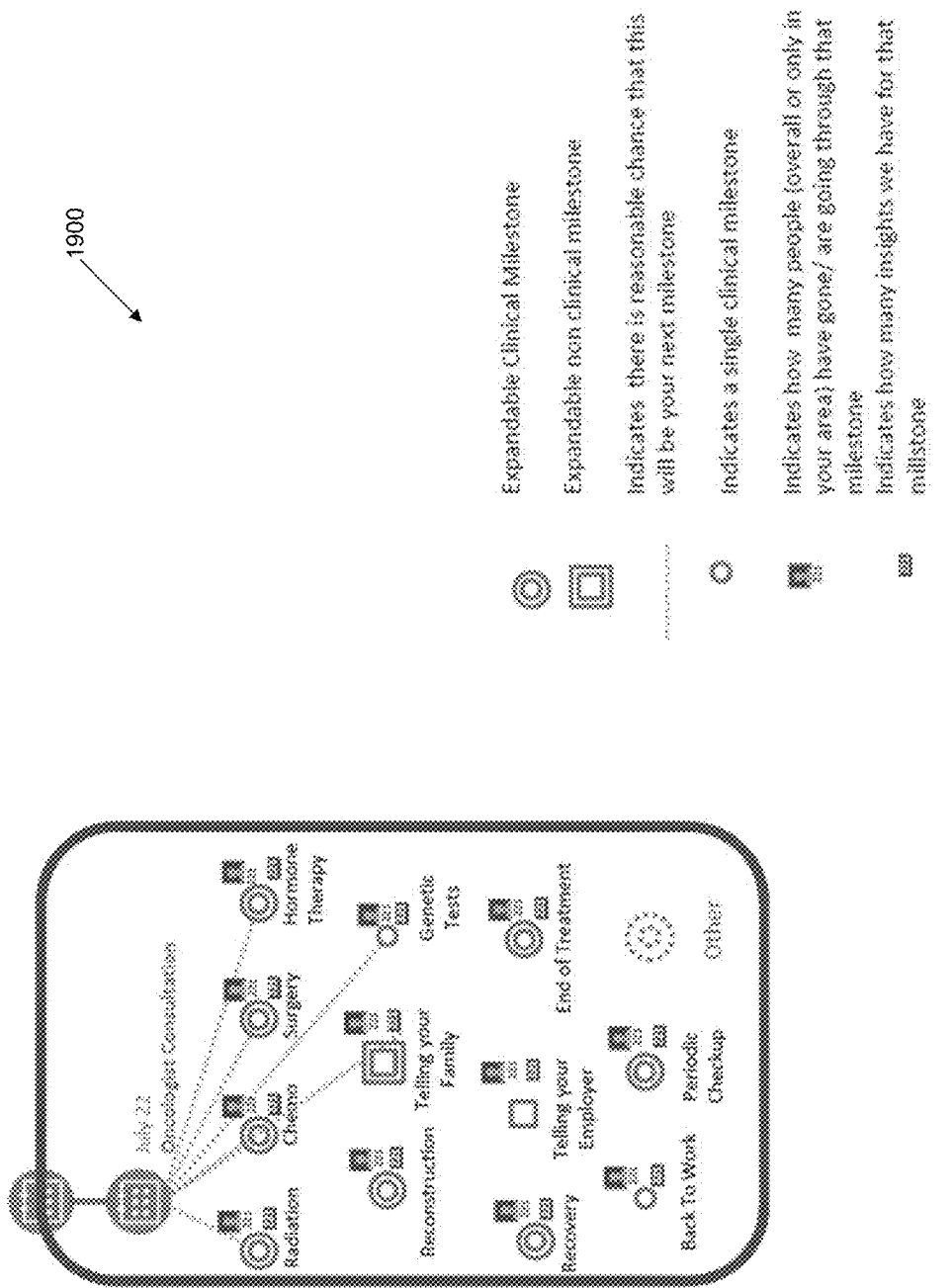
FIG. 19 illustrates an exemplary milestones window, in accordance with some embodiments.

In some embodiments, the probability of the user facing each milestone, and a predicted time at which the user would face each milestone, may be determined. The probabilities and predicted time may be determined by comparing the user to other similar users who have previously gone through those milestones, and using statistics/information about those other users. In some embodiments, the milestones that the user is likely going to face in the near future (i.e., higher probability of the user facing those milestones) may be provided nearer to the oncologist consultancy milestone than other milestones, and may be connected by dotted lines to the oncologist consultancy milestone. For example, as shown in FIG. 19, the user may likely face the milestones (radiation, chemo, telling his family, surgery, genetic tests, and hormone therapy) in the near future. Accordingly, those milestones may be connected by dotted lines to the oncologist consultancy milestone. Since the milestones (reconstruction, recovery, telling the user's employer, end of treatment, back to work, and periodic checkup) are less immediate, those milestones may be depicted as freely-floating in space without being connected by any dotted lines. In some instances, the user may select the "Other" button to see additional milestones that have not been displayed in window 1900.

As shown in FIG. 19, the milestones (radiation, chemo, telling his family, surgery, genetic tests, and hormone therapy) may be connected by dotted lines to the oncologist consultation milestone. A user may select any of the milestones to explore and observe how the journey and following milestones change. For example, referring to FIG. 20, when the user selects the chemo milestone, the chemo milestone may be directly connected to the oncologist consultation milestone by a solid line. The radiation, hormone therapy, and recovery milestones may be connected by dotted lines to the chemo milestone. Accordingly, the user can explore and see the next possible milestones upon selecting a particular milestone. In some embodiments, the feeds (insights) that are provided to the user may be influenced/customized depending on the milestones that the user selects. For example, if a user selects the chemotherapy milestone, feeds regarding chemotherapy may be provided to the user, as shown in FIG. 23. Conversely, if a user selects the kids/family milestone, feeds regarding how to interact with one's children during the SLT may be provided to the user, as shown in FIG. 26.

Figure 21:
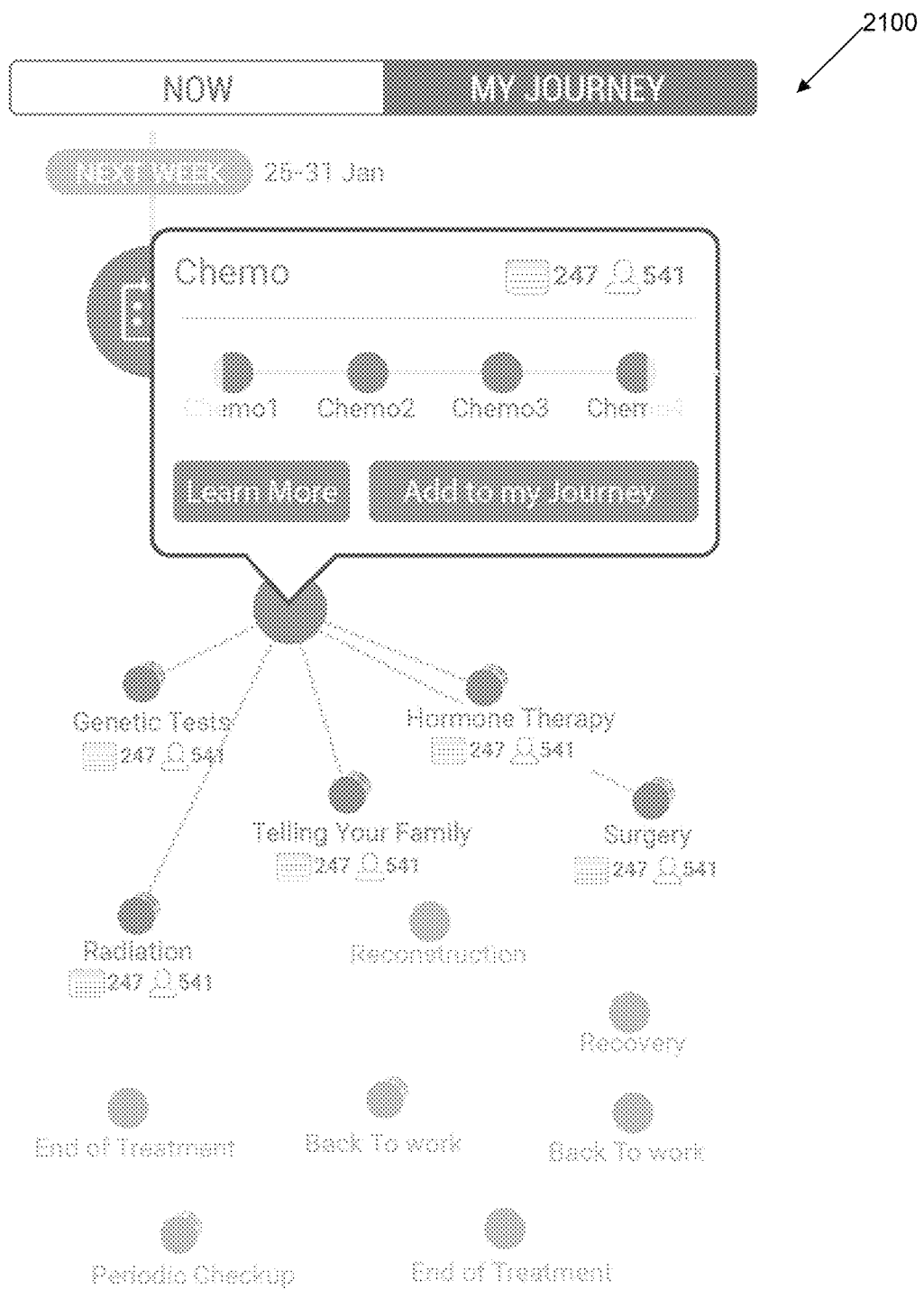
FIG. 21 illustrates another exemplary timeline window, in accordance with some embodiments.

FIG. 21 illustrates another exemplary timeline window 2100 in accordance with some embodiments. Referring back to FIG. 17, in some instances, the user may not have any milestone defined beyond the oncologist consultancy milestone on July 18. In those instances, when the user tries to scroll down window 1700 below the oncologist consultancy milestone, window 2100 of FIG. 21 may be generated. Window 2100 is similar to window 1900, and illustrates the other milestones that the user is likely going to face. In some embodiments, the other milestones may be depicted as floating in space. The milestones may include radiation, chemo, surgery, hormone therapy, reconstruction, telling the user's family, genetic tests, recovery, telling the user's employer, end of treatment, back to work, and/or periodic checkup. The milestones may include clinical milestones and non-clinical milestones. Each milestone may include a first indicator and a second indicator. The first indicator may indicate the number of people who have gone through or are going through the corresponding milestone. The second indicator may indicate the number of insights for the corresponding milestone.

The user can select the different milestones to find out what each milestone entails, where the milestones are located on the user's SLT journey, and the insights from other contributors for each milestone. For example, as shown in FIG. 21, the chemo milestone may have 247 insights, and 541 users/contributors may have the chemo milestone in their SLT journey. A user can read through the insights, and potentially connect with the other users/contributors. This can help the user to identify and plan her needs, thus allowing her to navigate through the SLT journey in an optimized manner.

In some embodiments, the milestones that the user is more likely going to face in the near future may be provided nearer to the oncologist consultancy milestone than other milestones, and may be connected by dotted lines to the oncologist consultancy milestone. For example, as shown in FIG. 21, the user may most likely going face the milestones (genetic tests, radiation, chemo, telling his family, hormone therapy, and surgery) in the near future. Accordingly, those milestones may be connected by dotted lines to the oncologist consultancy milestone. Since the milestones (reconstruction, recovery, telling the user's employer, end of treatment, back to work, and periodic checkup) are less immediate, those other milestones may be depicted as freely-floating in space without being connected any dotted lines.

Figure 22:
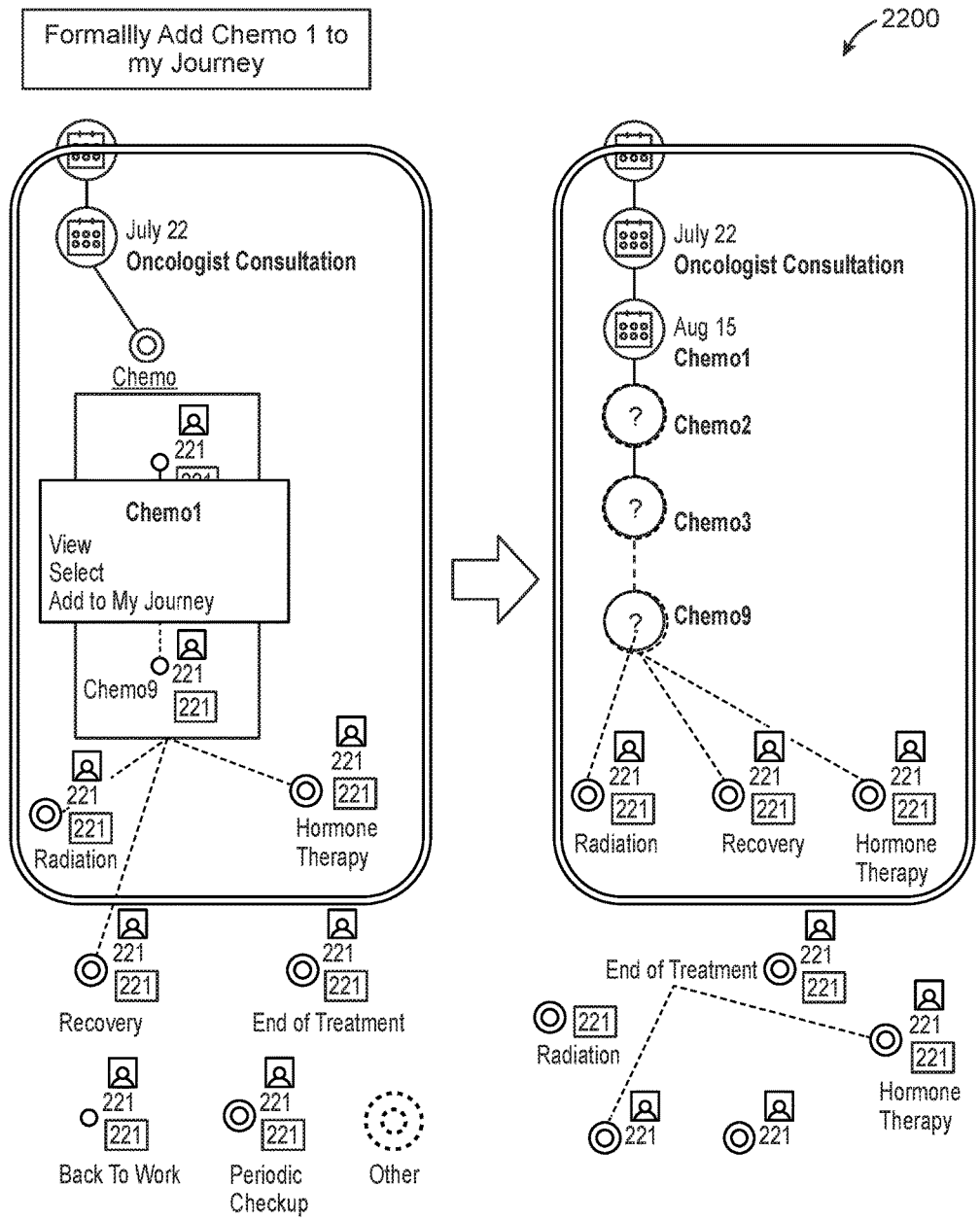
FIG. 22 illustrates the addition of milestones to a user's timeline, in accordance with some embodiments.

In some embodiments, when the user selects the chemo milestone, a sub-window comprising the milestones chemo 1, chemo 2, chemo 3, and chemo 4 may appear. The user may have the option to add one or more of the milestones chemo 1, chemo 2, chemo 3, and chemo 4 to her journey. For example, as shown in FIG. 22, the user may add the milestone chemo 1 to her journey. Accordingly, the milestone chemo 1 may be added to the user's timeline as a milestone on August 15. The other milestones chemo 2, chemo 3, and so forth may be denoted by a question mark, because those milestones and dates may have to be determined depending on the user's body response after the chemo 1 milestone.

Figure 20:
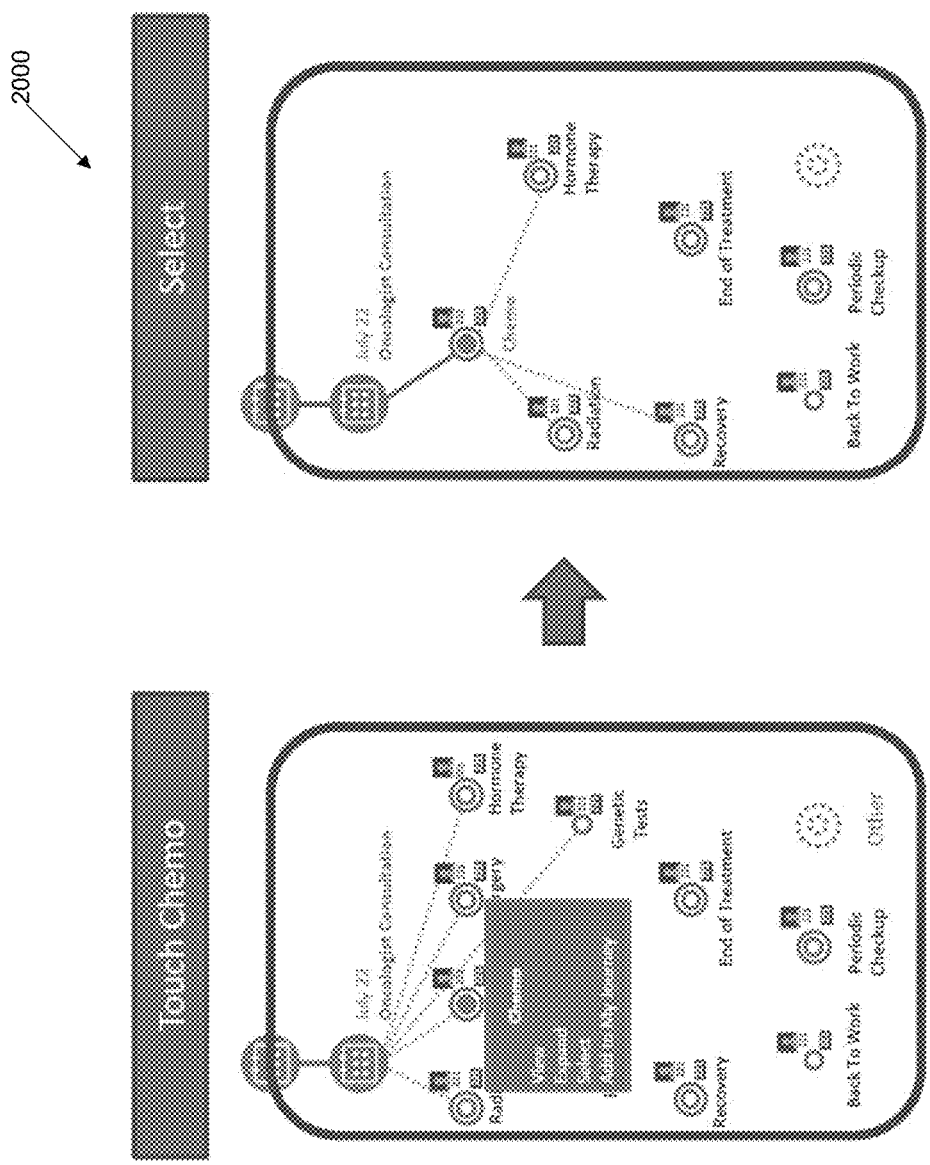
FIG. 20 illustrates the exploration of milestones, in accordance with some embodiments.

In the examples of FIGS. 19, 20, and 21, one or more paths (dotted lines) may be displayed to a user. For example, one or more paths may be displayed when the user selects two or more milestones. In some cases, a plurality of different paths may be displayed to the user, to show interconnections between different milestones. The paths may be generated using a model. The model can be trained on multiple user's journey and/or data of user navigation through the site for multiple users. The model may be based on machine learning methods such as probabilistic graphical models (e.g., Markov models), temporal sequence analysis, sequential pattern mining (e.g., variations of a priori algorithm), and methods incorporating network analysis and graph theory (e.g., shortest paths, centrality measures, etc.). In some embodiments, the paths can be generated using convex optimization methods which are extensions of convex functions such as biconvex, pseudo-convex, or quasi-convex functions.

Referring back to FIG. 21, the user may have the option to learn more about chemotherapy by selecting the Learn More button. When the user selects the Learn More button in window 2100, window 2300 of FIG. 23 may be generated. Window 2300 may include an explanation of what chemotherapy entails. Window 2300 may also include a list of people in the user's surrounding area, who may gone through or are going through the chemo milestone. These people may be at various stages of the chemo milestone (e.g., chemo 1, chemo 2, etc.). By connecting with others through window 2300, the user can utilize their collective wisdom, and in some instances can also receive emotional encouragement/support as the user navigates her own SLT journey.

In some embodiments, a user may be able to view other users' journeys in the windows. In some cases, the journeys for a plurality of different users may be overlay onto a single timeline. A user can also interact with one or more other users. For example, the user may be able to receive suggestions and/or recommendations from other users relating to different milestones and SLTs. In some embodiments, the event navigation system may be configured to detect similarities (and/or differences) between a user's journey and the journeys of other users. The similarities/differences may be detected using clustering methods or sequence alignment algorithms that are executed by the event navigation system.

A clustering method may be an unsupervised machine learning method. Cluster analysis may include the assignment of a set of observations into subsets (called clusters) such that observations within the same cluster are similar according to some predesignated criterion or criteria, while observations drawn from different clusters are dissimilar.

Different clustering techniques can be used to make different assumptions on the structure of the data, often defined by some similarity metric and evaluated for example by internal compactness (similarity between members of the same cluster) and separation between different clusters. Some other methods may be based on estimated density and graph connectivity.

Computational approaches to sequence alignment may fall into two categories: global alignments and local alignments. Calculating a global alignment is a form of global optimization that "forces" the alignment to span the entire length of all query sequences. By contrast, local alignments identify regions of similarity within long sequences that are often widely divergent overall. Local alignments are often preferable, but can be more difficult to calculate because of the additional challenge of identifying the regions of similarity. A variety of computational algorithms have been applied to the sequence alignment problem. These may include slow but formally correct methods like dynamic programming. These may also include efficient, heuristic algorithms or probabilistic methods designed for large-scale database searches.

In some embodiments, an insight can be multi-layered comprising a global insight and a geo-local insight. The global insight may be indicative of the general topic to which the insight relates. The geo-local insight may be the insight as applied to a specific locality and/or timeframe. For example, an insight may relate to the application of a disabled parking permit for a cancer patient. The global insight for the above insight may include general advice on where to obtain the disabled parking permit. The geo-local insight for the above insight may include specific advice on the exact procedure by state and county. For example, different states and counties may have different procedures and criteria for obtaining the permit.

The recommendation engine can be configured to generate a global insight of an insight based on its geo-local insight, or in the alternative, generate a geo-local insight based on its global insight. For example, the recommendation engine may be configured to: (1) automatically identify which part of an insight is its global insight and which part is its geo-local insight; (2) identify the localities where the geo-local insights for those localities are missing; (3) contact community members with the appropriate credentials from those localities, and request the missing geo-local insights for those localities; and (4) curate and verify the accuracy of those geo-local insights through other members of the same locality, or by comparing several versions of the geo-local insights for the same locality.

Window 2300 may further include a pie chart showing the relative distribution of the various insights: (1) financial and insurance, (2) preparations, (3) emotional, (4) symptoms and treatment, (5) work, and (6) support services. As shown in the pie chart, insights relating to financial and insurance, emotional, and symptoms and treatment constitute a large percentage of the total number of insights.

Window 2300 may also include a video testimonial of the founder of Breastcancer.org (Marisa Weiss) speaking about treatment options. Window 2300 may also include a card containing an emotional insight posted by a user/contributor named Brenda_k. The card may be titled "It's okay to discourage false cheerfulness and to share how you're feeling."

Figure 24:
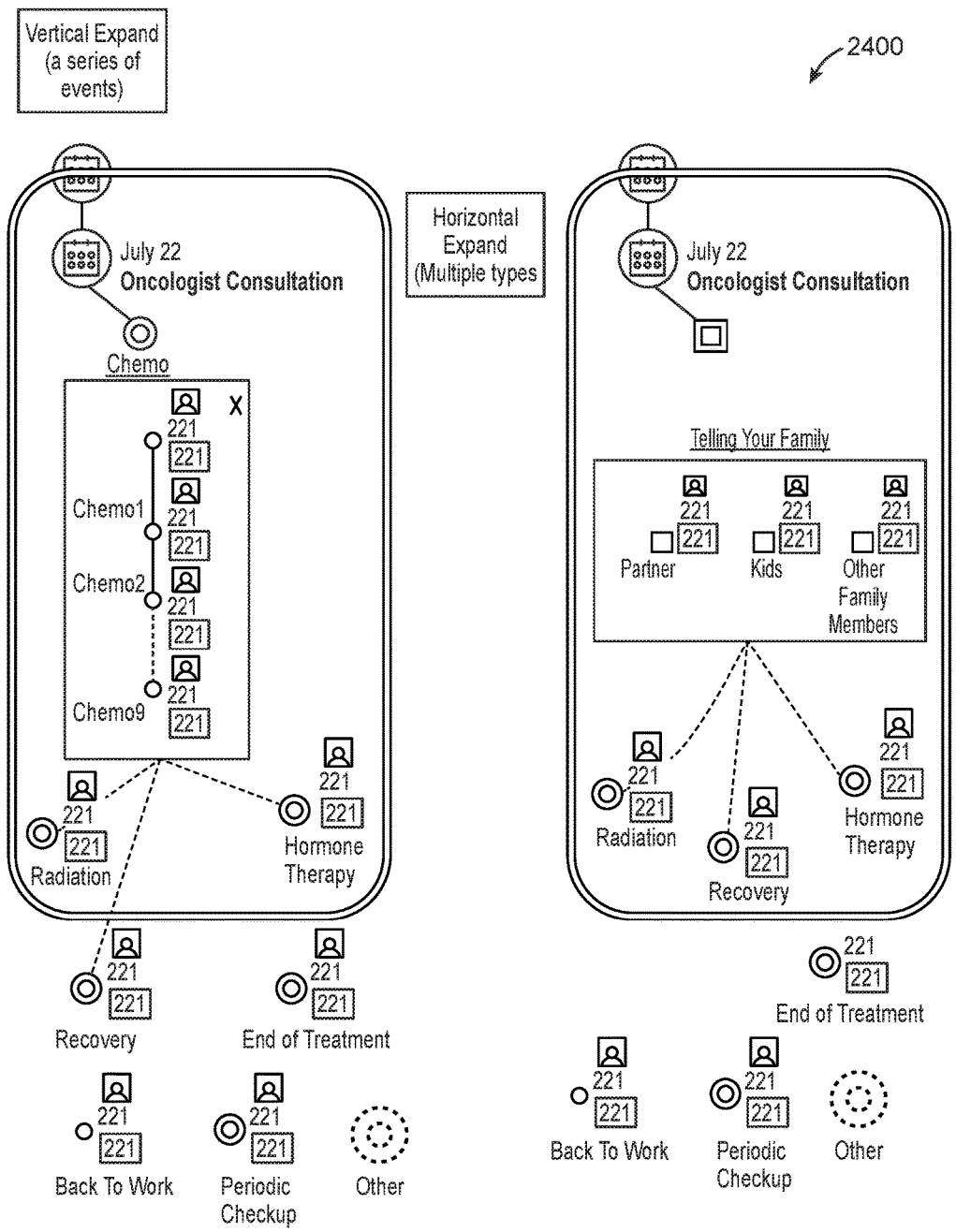
FIG. 24 illustrates different exemplary configurations for clinical milestones and non-clinical milestones, in accordance with some embodiments.

FIG. 24 illustrates different exemplary display configurations for clinical milestones and non-clinical milestones in accordance with some embodiments. In the example of FIG. 24, the chemo milestone may be an expandable clinical milestone, and the "telling your family" milestone may be an expandable non-clinical milestone. The chemo milestone may be expanded into a plurality of vertical milestones, and the "telling your family" milestone may be expanded into a plurality of horizontal milestones. When a user selects the chemo milestone, the chemo milestone may expand into a vertical series of milestones chemo 1, chemo 2, through chemo 9. Similarly, when the user selects the "telling your family" milestone, the "telling your family" milestone may expand into a horizontal series of milestones relating to the user's partner, user's children, and other family members. It is noted that the invention is not limited to the display configuration illustrated in the preceding figures. Any arrangement/layout of the milestones relative to the other milestones may be contemplated.

Figure 25:
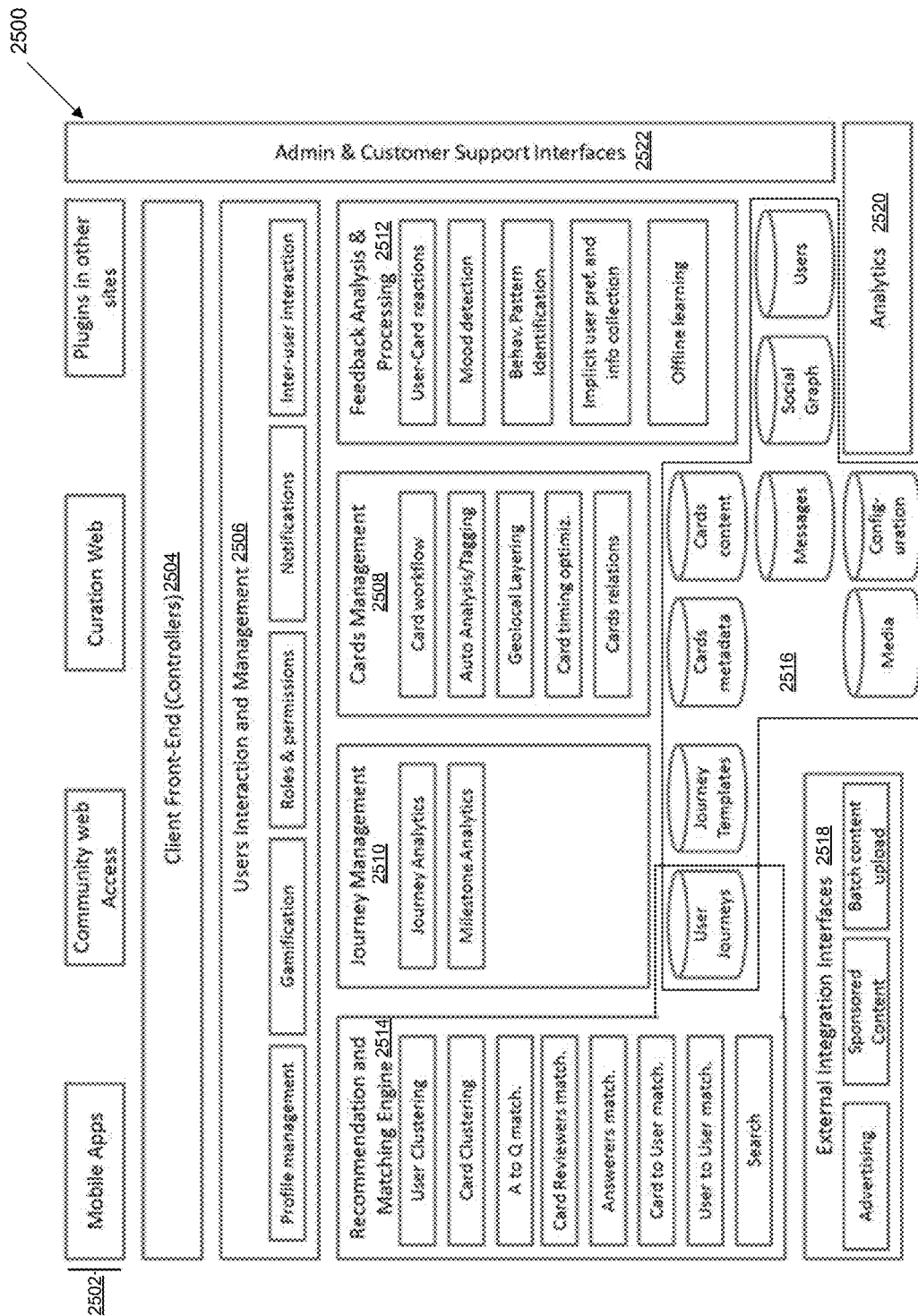
FIG. 25 illustrates components in an exemplary event navigation architecture system, in accordance with some embodiments.

FIG. 25 illustrates exemplary components in an event navigation architecture system 2500, in accordance with some other embodiments. Referring to FIG. 25, the architecture system may include user interfaces 2502, client front-end 2504, users interaction and management 2506, cards management 2508, journey management 2510, feedback analysis and processing 2512, recommendation and matching engine 2514, databases 2516, external integration interfaces 2518, data analytics 2520, and administration and customer support interfaces 2522. Each of the above components will be described in further detail as follows.

User interfaces 2502 may be clients and may comprise mobile applications 2502a, community web access 2502b, curation web 2502c, and plugins 2502d.

Mobile applications 2502a can provide functionality of and access to the event navigation system for users on the go (i.e., users using wireless devices). Examples of mobile applications 2502a may include Android™ and iOS™-based mobile applications for smartphones and tablets.

Community web access 2502b may be a web interface for users. The web interface can allow users to view cards, search for cards using tags and keywords, contribute new cards, and comment and interact (e.g., 'like' a card) with existing cards. As previously mentioned, cards may include relevant insights by contributors or articles from any source. In some embodiments, some features of the web access may be available to the general public, while other features of the web access may be available only to users who are registered users of the event navigation system.

Curation web 2502c may be a web interface for use by the curators/editors. In some instances, the curators/editors may comprise a small percentage of the community. For example, the curators/editors may comprise the top 1% of users in the community who have positive ratings and reviews by other users. The curators may be responsible for curating the incoming cards by the contributors. In some embodiments, the curation web may include the community web access functionality with additional management tools. The additional management tools may, for example, only allow curators to access, curate, and edit the incoming cards.

Plugins 2502d may include web plugins to other third party websites. The plugins may be provided in various forums, blogs and groups dealing with different SLTs. This can increase the user base of the system and provide the insights/cards to a larger user base. By increasing the user base, community wisdom can be extracted with a higher degree of accuracy/relevancy. The plugins can allow users to view cards, interact with cards, and create new cards from within the third party websites.

Client front-end 2504 may include a layer of controllers configured to provide user interfaces 2502 (clients) with services and data required to interact with the users. Client front-end 2504 may serve as an orchestration layer on top of other server components, and may be configured to provide abstract interfaces to the clients.

Users interaction and management 2506 may be a layer for providing services related to users management. Users interaction and management 2506 may include profile management 2506a, gamification 2506b, roles and permissions 2506c, notifications 2506d, and inter-user communication 2506e.

Profile management 2506a may be configured to retrieve and update user information for use of the other components. Profile management 2506a may be configured to manage subscription information (e.g., signup/login/password management etc.).

Gamification 2506b may be configured to collect and manage users' badges and points as part of the user rankings. Users can receive badges and points based on a plurality of factors (e.g., number of insights they provided, number of insights of insights they commented on, number of 'likes' or approval ratings by other users, time spent using the system, etc.). The badges and points can provide incentivize users to add insights, comment on insights, and/or spend more time using the system. When users are motivated to use the system, the user base may increase. Accordingly, the accuracy and/or relevancy of the milestones and insights can be improved.

Roles and permissions 2506c may be configured to manage user permissions since different users may have different roles and permissions in the system.

Notifications 2506d may be configured to manage the pending notifications per user. Notifications to a user may be generated under a variety of circumstances (e.g., when new insights are received, a reminder that a next milestone is upcoming, when messages are received from other users, etc.). Notifications 2506d may further include software/hardware interaction with different push notifications mechanisms (e.g. on mobile devices, tablets, etc.).

Inter-user communication 2506e can allow users to interact with one another. Users may interact by sending messages, sending 'hugs', or becoming 'friends' with one another. Inter-user communication 2506e may be configured to facilitate any of the above interactions.

Cards management 2508 may be configured to create cards, send cards, modify cards, etc. A card may be a structured piece of information containing content, a title, multimedia, as well as tags and metadata. A card can be created in many ways. For example, a card may be added by a curator, received from a content partner using an application programming interface (API), or contributed by users through the web interfaces or plugins. Once a card is added to the system, the system may send the card through a workflow. The workflow may begin with curator review (or moderator review). The curator review may include sending the card to a plurality of curators to review. The card is then sent to a number of users to be included in the users' journeys. The card may be continuously updated, revised, and/or improved while the card is still in the users' journeys. The updating, revision, or improvement of a card may include a combination of manual/automatic processes. For example, the system can be configured to automatically update a card based on new information and insights. Cards management 2508 may include card workflow 2508a, auto analysis/tagging 2508b, geolocal layering 2508c, card context optimization 2508d, and cards relations 2508e.

Card workflow 2508a may be configured to manage a life cycle of the card, by tracking the card's path in the process and moving the card between the stages of the workflow.

Auto analysis/tagging 2508b may be part of the card processing, and may include analyzing the content (e.g. text) of the card using natural language processing (NLP) and/or other appropriate techniques. This is done to extract the essence of the text, and to provide the system and the curators with some indication about the concepts, topics and sentiment conveyed in the card.

Geolocal layering 2508c may be configured to tag and manage cards based on their geographical locations. For example, some cards may be relevant only to specific geography (e.g., recommending relevant services in the vicinity where a user lives). Conversely, some cards may contain similar content, apart for their geographical locations. Geolocal layering 2508c can be configured to manage the above.

Card context optimization 2508d may be configured to collect relevant data, and to optimize the context and timing of the cards based on the relevant data. The relevant data may include the milestones and needs of the user, as determined by the system. Card context optimization 2508d may be configured to display the cards to a user at a specific timing and within a specific context. The type of cards, timing, and context may be influenced determined by a vote of the community. They may also be influenced by the actual responses of the users to the cards.

Cards relations 2508e may be configured to manage the relations between cards. For example, two cards may be related in many different ways (e.g., describing the same thing in different words, a card may provide additional information to another card, a card may be always viewed by users after another card, etc.). It is noted that the relations between the cards can change over time as the cards become updated or revised.

Journey management 2510 may be configured to collect community wisdom, and to build and maintain optimal journeys (also called journey templates) based on the collected wisdom. In life, different people may go through different journeys. As previously mentioned, the system can show a user the next possible events and milestones he may encounter at any stage. These next steps are based on the collection and aggregation of the journeys other users (similar to a particular user) have gone through. Journey management 2510 may include journey analytics 2510a and milestone analytics 2510b.

Journey analytics 2510a may be configured to collect users' journeys and to continuously updating their journeys based on the journey templates. Milestone analytics 2510b may be configured to collect information about the milestones (including personal milestones) that people add to their journeys. Milestone analytics 2510b may be further configured to suggest new milestones to be added to the system by analyzing the users' responses.

Feedback analysis and processing 2512 may be configured to receive a stream of events from the clients and to process the events online to enhance what the system already knows about the user. The events may include any activity of the user that is being recorded by the clients and reported to the server. In addition, any interaction (or lack of interaction) of the user with a specific card or the system may indicate a characteristic about the user, the user's current status, and/or about the card. The above information may be used later for offline learning to enhance the system's knowledge about cards and users, in order to improve internal algorithms for managing cards and card content. Feedback analysis and processing 2512 may be a main input to a social graph. For example, feedback analysis and processing 2512 may contain the user-content and preferences (e.g., 'likes') and user-user relations (e.g., 'friends', 'hugged', etc.). Feedback analysis and processing 2512 may include user-card interactions 2512a, mood detection 2512b, behavioral pattern identification 2512c, implicit user preferences and information collection 2512d, and offline learning 2512e.

User-card interactions 2512a may be configured to detect the user interactions with cards and to maintain the user-card relationship in the social graph (e.g. it can detect that the card was opened by a user for 2 seconds, or deleted without reading etc.).

Mood detection 2512b can detect and store a user's current mood for use by the recommendation engine, so that the appropriate cards can be provided to the user. The user's current mood can be detected based on the user interaction with the system (e.g., by analyzing the user's usage pattern, the user's text, etc.).

Behavioral pattern identification 2512c may be configured to collect and analyze the user interactions in order to categorize how a user copes with an event. This is because different people may cope with similar situations differently, and there may be several patterns of coping that can be identified. This can enable more relevant insights to be provided. In some instances, similar insights may be provided but with different tone or sentiment.

Implicit user preferences and information collection 2512d may be configured to analyze user interactions with the system to obtain information provided by users. The information may include deducing the user's geographical location based on places that the user frequents. In addition, areas of interests of a user can be deduced based on the time spent (or the time that is not spent) on cards of specific topics.

Offline learning 2512e may be configured to use the information collected in the social graph to improve parameters for the learning algorithms, provide insights on different aspects of services, how users use the services, and about the cards.

Recommendation and matching engine 2514 may include a set of components and algorithms configured to provide optimized content where required. Recommendation and matching engine 2514 may include user clustering 2514a, card clustering 2514b, answer-to-question matching 2514c, card reviewers matching 2514d, answers matching 2514e, card-to-user matching 2514f, user-to-user matching 2514h, search 2514h, and user future journey 2514i.

User clustering 2514a may be configured to identify user clusters, so as to predict possible behaviors of users based on other users.

Card clustering 2514b may be configured to identify card clusters, so as to determine which cards are have similar insights, which cards are directed to similar topics, and which cards may be used together.

Answer-to-question matching 2514c may be configured to provide optimized card matches based on a question and the user's history and current status. When a user asks a question, the system may attempt to match insights that the system predicts may be answering the question.

Card reviewers matching 2514d may be configured to select which appropriate users to send a card to, based on the users' history. In some instances, new cards may be sent to some selected users to review before the cards are released to the rest of the community. For example, a chemotherapy-related insight may be sent to a user for review, whereby the user may have gone through chemotherapy and may have a similar profile to another user who created the insight.

Answers matching 2514e may be configured to select which appropriate users to send a question to, based on the users' history. For example, when a user asks a question, the question may be sent to other selected users for answering, whereby the users may be selected based on their common history and similarity.

Card-to-user matching 2514e may be configured to select the most relevant cards to a user at a given time, based on the user's information, current moods and feelings, user preferences, and timeline in a journey etc.

User-to-user matching 2514f may provide a suggestion for a user to communicate with another user (e.g., if the other user has gone through the same milestone the user is facing).

Search 2514g allows a user to search by keywords or tags. The results may be based on the keywords, as well as information that the system has obtained about the user, in order to provide cards that are most likely to be relevant to the user.

User future journey 2514h may be configured to determine the next milestones for each user at any given time based on the user's profile, history and status. At every step of the journey, a user may be shown the next possible milestones in his journey, based on the paths of similar people who have gone through the journey before him.

Databases 2516 may include a list of entities that are stored and managed in different data storages of the system. Databases 2516 may include physical data storages or a service encapsulating physical data storages. Databases 2516 may include users 2516a, social graph 2516b, card metadata 2516c, card content 2516d, media (storage and service) 2516e, messages 2516f, user journeys 2516g, journey templates 2516h, and configuration 2516i.

Users 2516a may include the user profile and other structured information. Social graph 2516b may include the relations between users (e.g., "friends," "hugged," messaged, etc.) and between user and content (e.g., "liked," "read," "deleted," etc.). Card metadata 2516c may include metadata such as tags, features, lifecycle status etc. Card content 2516d may refer to textual content in the cards content. Media (storage and service) 2516e may be configured to store media elements (e.g., pictures, videos, audio recordings, etc.) and to provide the media elements to the clients (e.g., using a content delivery network (CDN)). Messages 2516f may be configured to store user-to-user messages. User journeys 2516g may be configured to store information relating to the users' journeys. Journey templates 2516h may contain a plurality of possible journeys for users, to be used for predicting and proposing the next milestones to users. Configuration 2516i may be any other system data that is not content related (e.g., administration data, system configuration etc.)

In some embodiments, a user may receive suggestions to interact with other users not only based on similar journeys, but also based on other similar properties such as navigation patters, interests or demographic properties. Such suggestions may be based on social network analysis methods such as link prediction, as well as recommendation system methods such as collaborative filtering. Some common network analysis applications may include data aggregation and mining, network propagation modeling, network modeling and sampling, user attribute and behavior analysis, community-maintained resource support, location-based interaction analysis, social sharing and filtering, recommender systems development, and link prediction and entity resolution.

The recommendation engine described elsewhere herein can be configured to produce a list of recommendations in various ways, for example through (1) a collaborative and content-based filtering approach or (2) a personality-based approach. A collaborative filtering approach can be used to build a model from a user's past behavior (milestones previously experienced) as well as similar decisions made by other users. This model is then used to predict recommendations that the user may have an interest in, or that may be relevant to the user. A content-based filtering approach can utilize a series of discrete characteristics of a milestone or a SLT in order to recommend certain actions for the users. The above approaches can be combined to form a hybrid recommendation engine. The personality-based approach can be used to provide recommendations to a user based on the user's personality.

External integration interfaces 2518 may include a collection of external interfaces that are configured to receive content from external sources. The content may include either advertisements, sponsored content, and/or uploaded content from content partners from the external sources.

Analytics 2520 can provide valuable insights in different areas, based on tracking and collecting information relating to the user's interaction with the system and the content. The insights can enable the system to learn about the following: (1) usage patterns, in order to improve applications and services, (2) content patterns, in order to improve the internal algorithms and/or learn about possible new features which can be added to improve the service; (3) the content (e.g. what insights are more beneficial than others); and (4) the journeys—are there more optimized journeys than others? (e.g., by analyzing how long users continue to use the application, how their moods are changing, etc.).

Administration and customer support interfaces 2522 may include a collection of interfaces for administration, maintenance and monitoring of the system by an operations teams. Administration and customer support interfaces 2522 may further include interfaces for the user of customer support to be able to access user specific data, for addressing complaints or support questions.

In some embodiments, since the system may store and maintain personal information and store medical information of its users, the system may be secured for compliance with regulations such as Health Insurance Portability Accountability Act (HIPAA) and ISO27001.

As previously described, different cards/feeds can relate to different topics (e.g., emotional, family, work, etc.). FIG. 26 illustrates an exemplary card window 2600 advising when a user should inform her children about her cancer diagnosis, in accordance with some embodiments. The insight in the card is related to kids, and applies to the milestone "Oncologist Consultancy." As shown in FIG. 26, the card may be posted by a contributor/user named Noa, and may have 175 votes and 1722 views. The card may further include links to external websites for more information on how to communicate news of the cancer to one's children.

Figure 27:
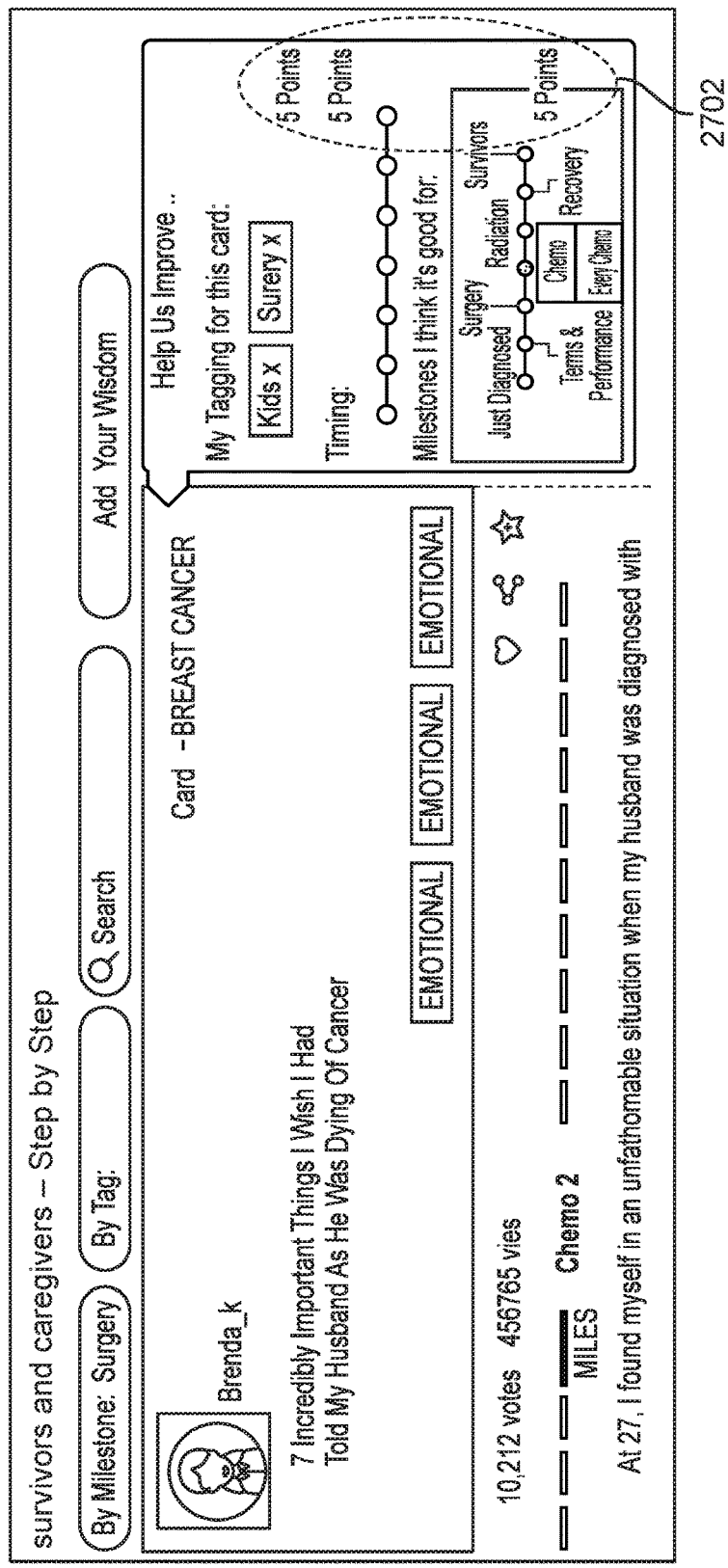
FIG. 27 illustrates an exemplary window incorporating gamification aspects, in accordance with some embodiments.

FIG. 27 illustrates an exemplary window 2700 incorporating gamification aspects, in accordance with some embodiments. Referring to window 2700, points 2702 may be awarded to a user based on various factors. For example, factors may include number of insights contributed by the user, number of 'likes' for an insight contributed by the user, time that the user spent navigating her journey on the system, number of cards the user opened/read, number of comments that were received for the user's insight, approval ratings for the user's insights, which milestone(s) the user has completed, etc. Points may be an incentive that is provided by the system to reward the user and to engage the user's interest. Points may be provided in a virtual form, for example, a virtual coin, a gamified item, etc. In some embodiments, the points may be exchanged for free samples/good/items, discounts, coupons, etc. In some embodiments, the points may be associated with user levels. For example, a first user level (e.g., junior) may be awarded to a user upon the user reaching a first number of points, a second user level (e.g., master) may be awarded to a user upon the user reaching a second number of points, whereby the second number of points may be higher than the first number of points.

In some embodiments, as users build their own journeys for different SLTs, the system describe herein can also employ machine learning to learn about the SLTs relate to one another, and the steps or phases where a SLT is more likely to occur. For example, in vitro fertilization (IVF) failure (a SLT) may lead to parenthood by adoption (another SLT). Similarly, caregiving of a loved one (a SLT) may be followed by coping with loss of the loved one (another SLT). The system can point users to one or more relevant SLTs that are likely to occur in the future, so that users can prepare for those SLTs beforehand prior to their occurrences.

Figure 28:
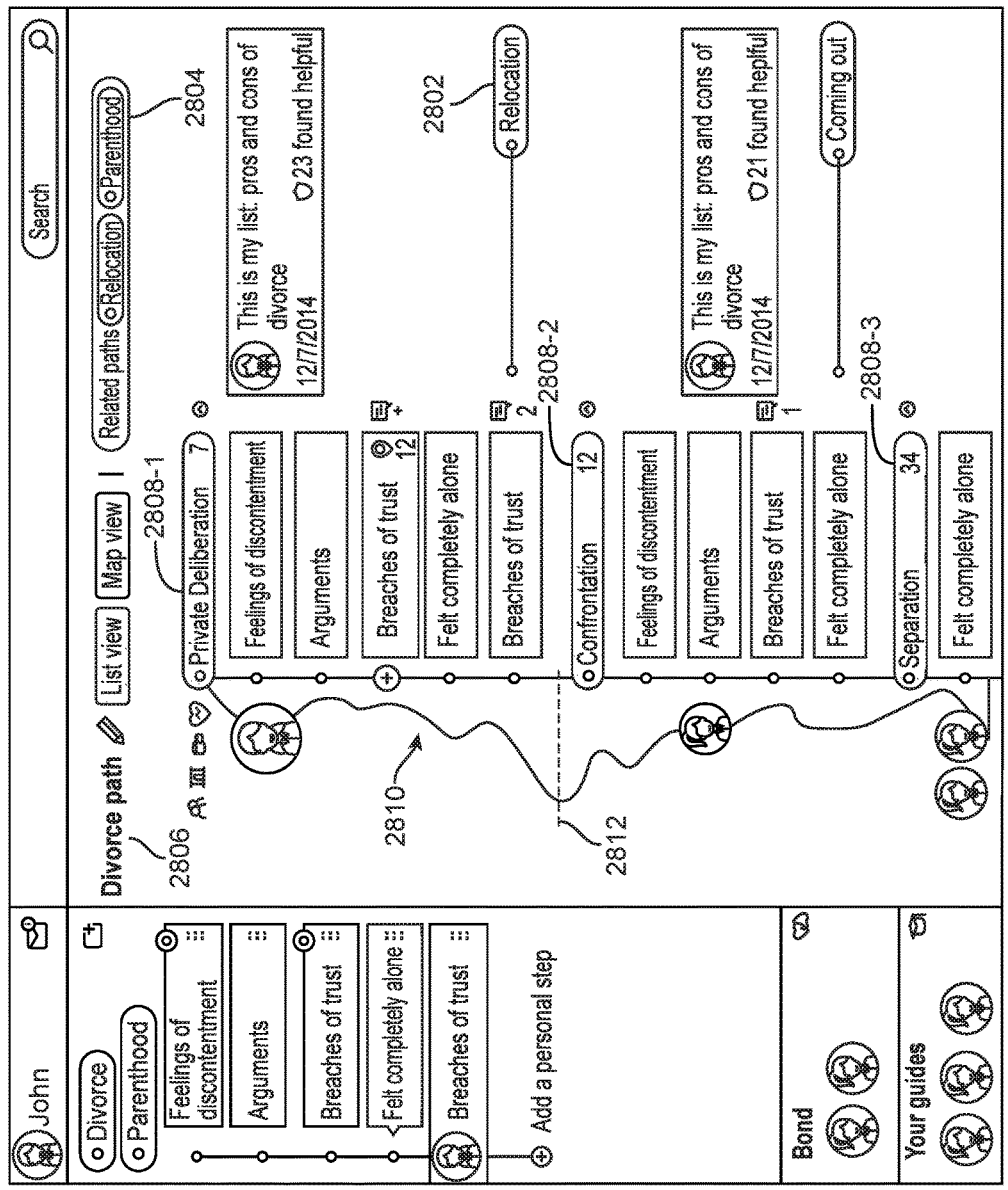
FIG. 28 illustrates an exemplary window comprising related SLTs and a heat map, in accordance with some embodiments.

FIG. 28 illustrates an exemplary window 2800 containing related SLTs, in accordance with some embodiments. In FIG. 28, one or more other SLTs (such as relocation 2802 and parenthood 2804) may be related to a divorce SLT 2806. The divorce may comprise a plurality of steps 2808. For example, the steps may start with private deliberation 2808-1, followed by confrontation 2808-2, and then separation 2808-3. Each milestone may be associated with one or more events or emotional feelings, such as feelings of discontentment, arguments, breaches of trust, feeling of loneliness, etc. Different users may be able to identify which milestones or events they are at.

In some embodiments, the system described herein can categorize the insights and dialog at each step of the various life challenges. The categorization can be performed using, for example, NLP, machine learning, user-based direct categorization, etc. An example of such categorization may be financial, physical, emotional, social, career-related, etc. The system can quantify the data and create a "heat map" that shows the relative impact of each category per step along the life challenge. Users can use the "heat map" to see which are the leading categories that dominate a specific step or life challenge. For example, users can determine whether the leading categories are emotional, financial, etc. The "heat map" can also allow users to understand the significance/impact of a particular step compared to the significance/impact that the users had experienced in previous steps. FIG. 28 illustrates a heat map 2810. An intensity of the heat map may be highest at the confrontation step 2808-2, as indicated by peak 2812.

Computer Control Systems

The present disclosure provides computer control systems that are programmed to implement methods of the disclosure. FIG. 29 shows a computer system 2901 that is programmed or otherwise configured to implement a method for assisting a user in navigating events happening in the user's life. As previously described, such events may be related to significant life transitions (SLTs), for example, going to college, getting married, having children, starting a business, getting divorced, retirement, relocation, or diagnosed with a terminal illness, among others. The computer system 2901 can store and/or execute software that performs an algorithm for processing user input, identifying an event from the user input, and determining relevant milestone(s) and need(s) associated with the event. The computer system 2901 can be an electronic device of a user or a computer system that is remotely located with respect to the electronic device. The electronic device can be a mobile electronic device.

The computer system 2901 includes a central processing unit (CPU, also "processor" and "computer processor" herein) 2905, which can be a single core or multi core processor, or a plurality of processors for parallel processing. The computer system 2901 also includes memory or memory location 2910 (e.g., random-access memory, read-only memory, flash memory), electronic storage unit 2915 (e.g., hard disk), communication interface 2920 (e.g., network adapter) for communicating with one or more other systems, and peripheral devices 2925, such as cache, other memory, data storage and/or electronic display adapters. The memory 2910, storage unit 2915, interface 2920 and peripheral devices 2925 are in communication with the CPU 2905 through a communication bus (solid lines), such as a motherboard. The storage unit 2915 can be a data storage unit (or data repository) for storing data. The computer system 2901 can be operatively coupled to a computer network ("network") 2930 with the aid of the communication interface 2920. The network 2930 can be the Internet, an internet and/or extranet, or an intranet and/or extranet that is in communication with the Internet. The network 2930 in some cases is a telecommunication and/or data network. The network 2930 can include one or more computer servers, which can enable distributed computing, such as cloud computing. The network 2930, in some cases with the aid of the computer system 2901, can implement a peer-to-peer network, which may enable devices coupled to the computer system 2901 to behave as a client or a server.

The CPU 2905 can execute a sequence of machine-readable instructions, which can be embodied in a program or software. The instructions may be stored in a memory location, such as the memory 2910. The instructions can be directed to the CPU 2905, which can subsequently program or otherwise configure the CPU 2905 to implement methods of the present disclosure. Examples of operations performed by the CPU 2905 can include fetch, decode, execute, and writeback.

The CPU 2905 can be part of a circuit, such as an integrated circuit. One or more other components of the system 2901 can be included in the circuit. In some cases, the circuit is an application specific integrated circuit (ASIC).

The storage unit 2915 can store files, such as drivers, libraries and saved programs. The storage unit 2915 can store user data, e.g., user preferences and user programs. The computer system 2901 in some cases can include one or more additional data storage units that are external to the computer system 2901, such as located on a remote server that is in communication with the computer system 2901 through an intranet or the Internet.

The computer system 2901 can communicate with one or more remote computer systems through the network 2930. For instance, the computer system 2901 can communicate with a remote computer system of a user (e.g., an end user, a contributor, a curator, an entity, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2901 via the network 2930.

Methods as described herein can be implemented by way of machine (e.g., computer processor) executable code stored on an electronic storage location of the computer system 2901, such as, for example, on the memory 2910 or electronic storage unit 2915. The machine executable or machine readable code can be provided in the form of software. During use, the code can be executed by the processor 2905. In some cases, the code can be retrieved from the storage unit 2915 and stored on the memory 2910 for ready access by the processor 2905. In some situations, the electronic storage unit 2915 can be precluded, and machine-executable instructions are stored on memory 2910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2901 can include or be in communication with an electronic display 2935 that comprises a user interface (UI) 2940 for providing, for example, a user portal for event navigation. A user can view timelines, journeys, milestones, events, steps, topics, insights, forums, etc. via the portal (e.g., the windows shown in FIGS. 17-22). The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2905. For example, the algorithm may be configured to process user input, identify an event from the user input, and determine relevant milestone(s) and need(s) associated with the event. The algorithm may also be configured to define and classify a plurality of topics relating to those milestone(s) and need(s). The algorithm may also be configured to search and extract questions stored in one or more database(s) relating to those topics/milestone(s). The algorithm may also be configured to search and extract insights and comments stored in one or more database(s) relating to those topics or milestone(s). The algorithm may also be configured to filter the questions and insights, and match the filtered questions/insights to the user's needs/milestones. The algorithm may also be configured to sort the matched insights/questions, and provide personalized recommendations to the user based on the user's milestones, timeline and needs. A variety of algorithms may be performed for performing one or more event navigation techniques.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented system for assisting a plurality of users in navigating one or more life events, the system comprising:
   (1) a matching engine configured to, with aid of one or more processors:
       receive input data from a plurality of computing devices associated with a plurality of users, wherein the input data comprises queries and insights from different users relating to the one or more life events;
       identify the type of life event(s) and a plurality of milestones that one or more users are currently experiencing, have experienced, or are likely to experience, by using a natural language processing (NLP) algorithm for multiclass and multilabel categorization to extract features and derive meaning from the users' queries and insights associated with the life event(s); and
       match the insights with the queries to the plurality of milestones located along a plurality of timelines for the one or more users; and
   (2) a recommendation engine configured to, with aid of one or more processors:
       predict needs of the one or more users at the plurality of milestones along the plurality of timelines, by analyzing the matched insights and queries to predict the users' needs; and
       generate personalized recommendations to the one or more users based on the users' predicted needs at the plurality of milestones as the users undergo the life event(s),
   wherein the timelines, milestones, queries, insights, and/or personalized recommendations are configured to be displayed as a set of visual objects on graphical displays of the computing devices associated with the one or more users.

2. The system of claim 1, wherein the one or more life events are selected from the group consisting of (i) diagnosis with a terminal illness, (ii) death, (iii) marriage, (iv) divorce and (v) retirement.

3. The system of claim 1, wherein the matching engine is configured to (1) categorize the queries for different subjects, (2) tag the queries, (3) find similar queries or existing answers to those queries, and/or (4) match queries to one or more users who are able to answer those queries, for each of the one or more life events.

4. The system of claim 1, wherein the matching engine is configured to aggregate and categorize the insights into a plurality of classes comprised of the plurality of milestones or life events using the natural language processing (NLP) algorithm.

5. The system of claim 4, wherein the plurality of milestones comprises clinical milestones and non-clinical milestones associated with the one or more life events, and wherein the matching engine is configured to establish relationships between the clinical milestones and non-clinical milestones by analyzing the users' queries and insights using the natural language processing (NLP) algorithm.

6. The system of claim 1, wherein the matching engine is configured to generate vector representations of categorized or labeled insights, and reduce a dimension of the vector representations using one or more feature selection methods.

7. The system of claim 1, wherein the matching engine comprises statistical models that are configured to determine probabilistic decisions based on attaching of real-valued weights to each of the one or more life events or milestones, and wherein the probabilistic decisions are usable to aid the one or more users in navigating the life events and milestones.

8. The system of claim 1, wherein the predicted needs and personalized recommendations to the one or more users are mapped onto the plurality of timelines and milestones in a chronological order.

9. The system of claim 1, wherein the matching engine is configured to (1) analyze a user's previous query in addition to a present query to establish a probability that the user is undergoing an identified life event, and (2) extrapolate information from the user's previous and present queries to determine present milestones and generate future milestones on the user's timelines for the identified life event.

10. The system of claim 1, wherein the recommendation engine comprises a predictive model that is configured to predict one or more future milestones for the one or more users for one or more life events, wherein the predictive model is trained using input data that is collected as a plurality of users undergo the same or similar life event or different life events, and wherein the predictive model is built on machine learning including probabilistic graphical models, temporal sequence analysis, and/or methods incorporating network analysis and graph theory.

11. The system of claim 1, further comprising:
a curation engine configured to:
   receive the matched insights and queries from the matching engine;
   determine a frequency at which the matched queries and insights appear or are accessed by the one or more users at each of the plurality of milestones along the plurality of timelines;
   filter the matched queries and insights based on the determined frequency at each of the plurality of milestones; and
   provide the filtered queries and insights to a plurality of curators for editing, curation and scoring.

12. The system of claim 11, wherein the curation engine is further configured to filter the scored queries and insights from the plurality of curators, by comparing their scores to one or more predetermined thresholds and ranking the queries and insights based said comparison of the scores.

13. The system of claim 1, wherein the recommendation engine is further configured to predict the needs of the one or more users based on one or more of the following: (1) profiles of the one or more users, (2) information obtained directly or indirectly from the one or more users via social media or a social networking website, (3) action or inaction of the one or more users pertaining to the milestones and/or life events, and/or (4) online interaction between two or more users.

14. The system of claim 1, wherein the recommendation engine is configured to generate new personalized recommendations to the one or more users when the matching engine receives new queries or insights from the one or more users, or when new milestones have been added to the plurality of timelines.

15. A computer-implemented method for assisting a plurality of users in navigating one or more life events, the method comprising:
   receiving input data from a plurality of computing devices associated with a plurality of users, wherein the input data comprises queries and insights from different users relating to the one or more life events;
   identifying the type of life event(s) and a plurality of milestones that one or more users are currently experiencing, have experienced, or are likely to experience, by using a natural language processing (NLP) algorithm for multiclass and multilabel categorization to extract features and derive meaning from the users' queries and insights associated with the life event(s);
   matching the insights with the queries to the plurality of milestones located along a plurality of timelines for the one or more users;
   predicting needs of the one or more users at the plurality of milestones along the plurality of timelines, by analyzing the matched insights and queries to predict the users' needs; and
   generating personalized recommendations to the one or more users based on the users' predicted needs at the plurality of milestones as the users undergo the life event(s),
   wherein the timelines, milestones, queries, insights, and/or personalized recommendations are configured to be displayed as a set of visual objects on graphical displays of the computing devices associated with the one or more users.

16. The method of claim 15, wherein the one or more life events are selected from the group consisting of (i) diagnosis with a terminal illness, (ii) death, (iii) marriage, (iv) divorce and (v) retirement.

17. The method of claim 15, further comprising, for each of the one or more life events: (1) categorizing the queries for different subjects, (2) tagging the queries, (3) finding similar queries or existing answers to those queries, and/or (4) matching queries to one or more users who are able to answer those queries.

18. The method of claim 15, further comprising: aggregating and categorizing the insights into a plurality of classes comprised of the plurality of milestones or life events using the natural language processing (NLP) algorithm.

19. The method of claim 18, wherein the plurality of milestones comprises clinical milestones and non-clinical milestones associated with the one or more life events, the method further comprising:
   establishing relationships between the clinical milestones and non-clinical milestones by analyzing the users' queries and insights using the natural language processing (NLP) algorithm.

20. The method of claim 15, further comprising:
   generating vector representations of categorized or labeled insights; and
   reducing a dimension of the vector representations using one or more feature selection methods.

21. The method of claim 15, comprising: using statistical models to determine probabilistic decisions based on attaching of real-valued weights to each of the one or more life events or milestones, wherein the probabilistic decisions are usable to aid the one or more users in navigating the life events and milestones.

22. The method of claim 15, comprising: mapping the predicted needs and personalized recommendations to the one or more users onto the plurality of timelines and milestones in a chronological order.

23. The method of claim 15, comprising:
   analyzing a user's previous query in addition to a present query to establish a probability that the user is undergoing an identified life event; and
   extrapolating information from the user's previous and present queries to determine present milestones and generate future milestones on the user's timelines for the identified life event.

24. The method of claim 15, comprising: using a predictive model to predict one or more future milestones for the one or more users for one or more life events, wherein the predictive model is trained using input data that is collected as a plurality of users undergo the same or similar life event or different life events, and wherein the predictive model is built on machine learning including probabilistic graphical models, temporal sequence analysis, and/or methods incorporating network analysis and graph theory.

25. The method of claim 15, further comprising:
determining a frequency at which the matched queries and insights appear or are accessed by the one or more users at each of the plurality of milestones along the plurality of timelines;
filtering the matched queries and insights based on the determined frequency at each of the plurality of milestones; and
providing the filtered queries and insights to a plurality of curators for editing, curation and scoring.

26. The method of claim 25, further comprising:
filtering the scored queries and insights from the plurality of curators, by comparing their scores to one or more predetermined thresholds and ranking the queries and insights based on said comparison of the scores.

27. The method of claim 15, comprising: further predicting the needs of the one or more users based on one or more of the following: (1) profiles of the one or more users, (2) information obtained directly or indirectly from the one or more users via social media or a social networking website, (3) action or inaction of the one or more users pertaining to the milestones and/or life events, and/or (4) online interaction between two or more users.

28. The method of claim 15, further comprising: generating new personalized recommendations to the one or more users when the matching engine receives new queries or insights from the one or more users, or when new milestones have been added to the plurality of timelines.

29. A tangible computer readable medium storing instructions that, when executed by one or more servers, causes the one or more servers to perform a computer-implemented method for assisting a plurality of users in navigating one or more life events selected from a group consisting of (i) diagnosis with a terminal illness, (ii) death, (iii) marriage, (iv) divorce and (v) retirement, the method comprising:
with aid of a matching engine:
receiving input data from a plurality of computing devices associated with a plurality of users, wherein the input data comprises queries and insights from different users relating to the one or more life events;
identifying the type of life event(s) and a plurality of milestones that one or more users are currently experiencing, have experienced, or are likely to experience, by using a natural language processing (NLP) algorithm for multiclass and multilabel categorization to extract features and derive meaning from the users' queries and insights associated with the life event(s); and
matching the insights with the queries to a plurality of milestones located along a plurality of timelines for one or more users; and
with aid of a recommendation engine:
predicting needs of the one or more users at the plurality of milestones along the plurality of timelines, by analyzing the matched insights and queries to predict the users' needs; and
generating personalized recommendations to the one or more users based on the users' predicted needs at the plurality of milestones as the users undergo the life event(s).

30. The computer readable medium of claim 29, wherein the stored instructions further comprise computer code for displaying the timelines, milestones, queries, insights, and/or personalized recommendations as a set of visual objects on graphical displays of the computing devices associated with the one or more users.

* * * * *